United States Patent
Yamakawa et al.

(10) Patent No.: US 9,668,705 B2
(45) Date of Patent: Jun. 6, 2017

(54) X-RAY TOMOGRAM IMAGING DEVICE

(75) Inventors: Tsutomu Yamakawa, Osaka (JP); Masahiro Tsujita, Osaka (JP); Akitoshi Katsumata, Ichinomiya (JP); Koichi Ogawa, Tokyo (JP); Hisatoshi Aoki, Osaka (JP)

(73) Assignee: TAKARA TELESYSTEMS CORP., Osaka-Shi, Osaka (JP)

( * ) Notice: Subject to any disclaimer, the term of this patent is extended or adjusted under 35 U.S.C. 154(b) by 1016 days.

(21) Appl. No.: 13/809,693

(22) PCT Filed: Jul. 13, 2011

(86) PCT No.: PCT/JP2011/065987
§ 371 (c)(1),
(2), (4) Date: Jun. 5, 2013

(87) PCT Pub. No.: WO2012/008492
PCT Pub. Date: Jan. 19, 2012

(65) Prior Publication Data
US 2015/0305696 A1    Oct. 29, 2015

(30) Foreign Application Priority Data
Jul. 13, 2010    (JP) .................................. 2010-158542

(51) Int. Cl.
*A61B 6/14* (2006.01)
*A61B 6/03* (2006.01)
(Continued)

(52) U.S. Cl.
CPC ................ *A61B 6/14* (2013.01); *A61B 6/025* (2013.01); *A61B 6/035* (2013.01); *A61B 6/466* (2013.01);
(Continued)

(58) Field of Classification Search
CPC .......... A61B 6/035; A61B 6/14; A61B 6/466; A61B 6/547; A61B 6/583; A61B 6/032;
(Continued)

(56) References Cited

U.S. PATENT DOCUMENTS

| 6,018,563 A | 1/2000 | Arai et al. |
| 2001/0036246 A1 | 11/2001 | Graumann |

(Continued)

FOREIGN PATENT DOCUMENTS

| JP | 57(1982)-203430 A | 12/1982 |
| JP | 3023633 U | 4/1996 |

(Continued)

OTHER PUBLICATIONS

International Search Report for PCT/JP2011/060731, ISA/JP, mailed Jun. 14, 2011.
(Continued)

*Primary Examiner* — Glen Kao
(74) *Attorney, Agent, or Firm* — Harness, Dickey & Pierce, P.L.C.

(57) ABSTRACT

An X-ray tomographic imaging apparatus includes an X-ray and a direct conversion type of detector. The X-ray tube and the detector are supported by the support means so as to be rotatable along curved orbits mutually independently. Under instructions from a computer, scans and image reconstruction are performed. The X-ray tube and the detector are moved along the orbits mutually independently so that X-ray beams are always transmitted through a desired tomographic plane of an object at desired angles. Acquired frame data are used to produce a panoramic image of the plane, while the frame data and the panoramic image are used to produce a tomographic image in which structural components of the object are optically focused and distortions caused due to differences in X-ray paths are suppressed. The apparatus can (Continued)

be used as devices for dental, medical diagnosis and non-destructive inspection, and can have a CT imaging function.

23 Claims, 62 Drawing Sheets

(51) Int. Cl.
*A61B 6/02* (2006.01)
*A61B 6/00* (2006.01)
*G06T 11/00* (2006.01)

(52) U.S. Cl.
CPC ............ *A61B 6/583* (2013.01); *G06T 11/006* (2013.01); *A61B 6/547* (2013.01); *G06T 2207/10081* (2013.01); *G06T 2207/30036* (2013.01); *G06T 2207/30196* (2013.01); *G06T 2211/436* (2013.01)

(58) Field of Classification Search
CPC ....... A61B 6/469; A61B 6/4441; A61B 6/588; A61B 6/145; A61B 6/4028; A61B 6/501; A61B 6/037; A61B 6/04; A61B 6/08; A61B 6/5223; A61B 6/0421; A61B 6/0478; A61B 6/06; A61B 6/025; G06T 11/006; G06T 2207/10081; G06T 2207/30036; G06T 2207/30196; G06T 2211/436
USPC ..................................... 378/38, 62
See application file for complete search history.

(56) References Cited

U.S. PATENT DOCUMENTS

| | | |
|---|---|---|
| 2004/0252811 A1 | 12/2004 | Morita et al. |
| 2005/0117693 A1 | 6/2005 | Miyano |
| 2006/0203959 A1 | 9/2006 | Spartiotis et al. |
| 2009/0123892 A1 | 5/2009 | Sogo et al. |
| 2009/0310845 A1 | 12/2009 | Ogawa et al. |

FOREIGN PATENT DOCUMENTS

| | | |
|---|---|---|
| JP | 3023663 U | 4/1996 |
| JP | 2007-7358 A | 1/2007 |
| JP | 2007-136163 A | 6/2007 |
| JP | 2007-524438 A | 8/2007 |
| JP | 2010-42119 A | 2/2010 |
| WO | 2004/086972 A2 | 10/2004 |
| WO | 2011-142343 A1 | 11/2011 |

OTHER PUBLICATIONS

International Preliminary Report on Patentability for PCT/JP2011/060731, IB, Geneva, issued Dec. 10, 2012, incorporating the English Translation of the Written Opinion of the ISA, ISA/JP, mailed Jun. 14, 2011.
International Search Report for PCT/JP2011/065987, ISA/JP, mailed Nov. 1, 2011.
International Preliminary Report on Patentability for PCT/JP2011/065987, IB, Geneva, issued Feb. 12, 2013, incorporating the English Translation of the Written Opinion of the ISA, ISA/JP, mailed Nov. 1, 2011.

(INITIAL POSITIONS)

(FOR REFERENTIAL-PLANE POSITION)

(FOR OUTER-PLANE POSITION)

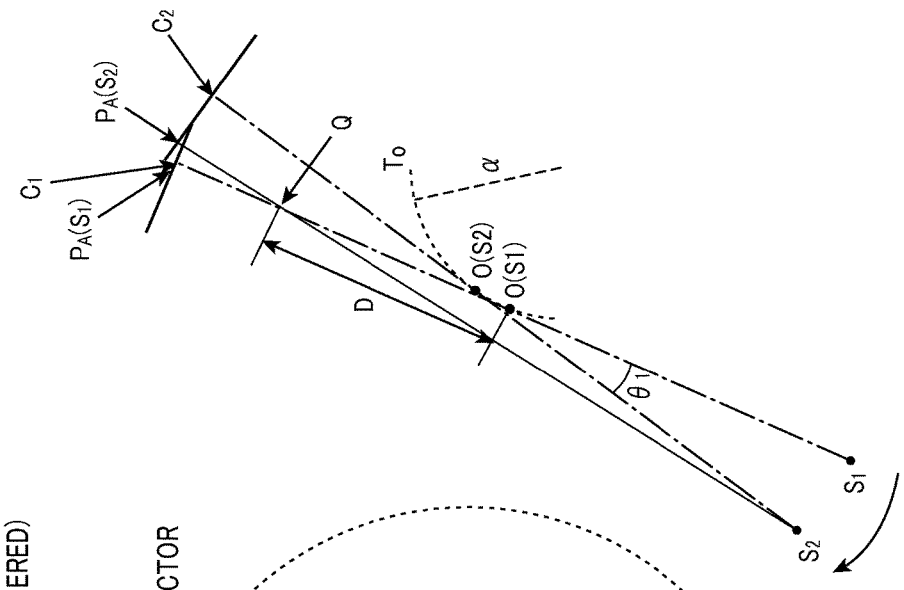
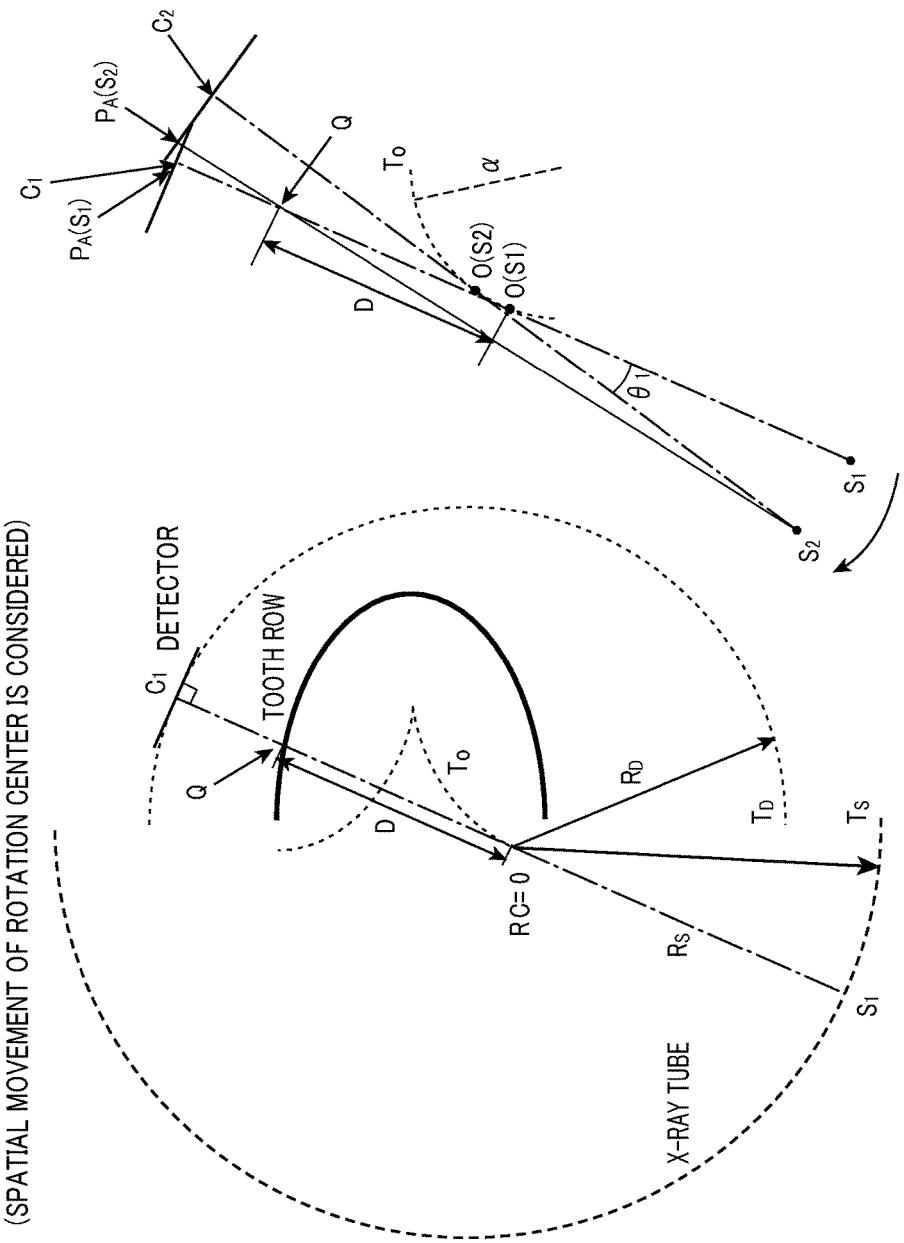

FIG.24(A)
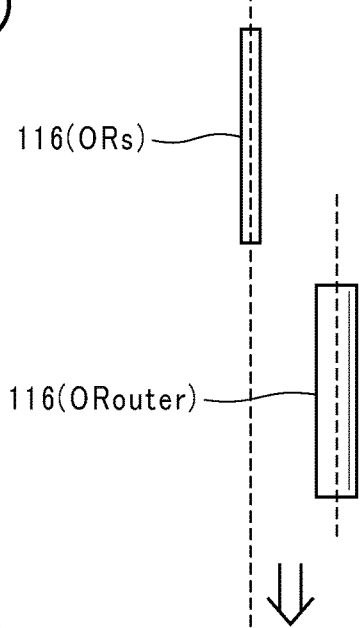
116(ORs)
116(ORouter)
⇓
FIG.24(B)
116(ORs)
← DISPLACED AMOUNT Pshift ON IMAGE
116(ORouter)
FIG.24(C)
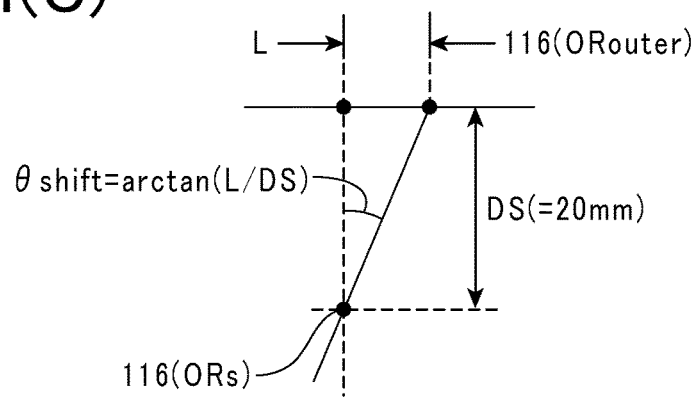
L ← → ← 116(ORouter)
θshift=arctan(L/DS)
DS(=20mm)
116(ORs)

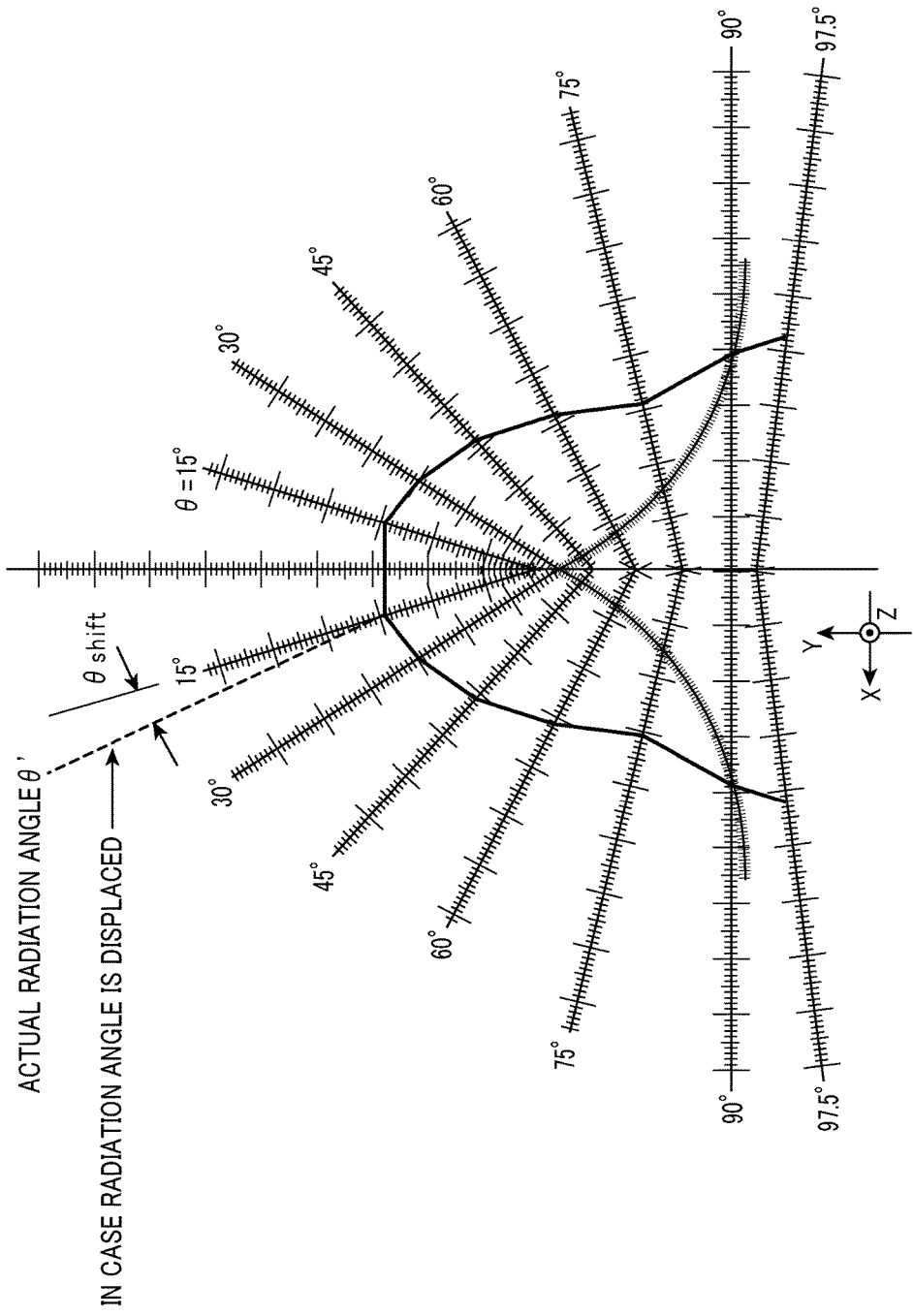

k1,k2,K3,···,Kn : DIFFERENT

⇓ ×1/K1,1/K2,1/K3,···,1/Kn

EQUAL ENLARGEMENT FACTORS OF TEETH

FIG.40(A)
(A)
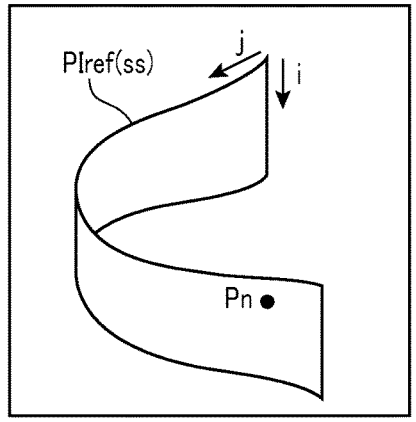
(B)
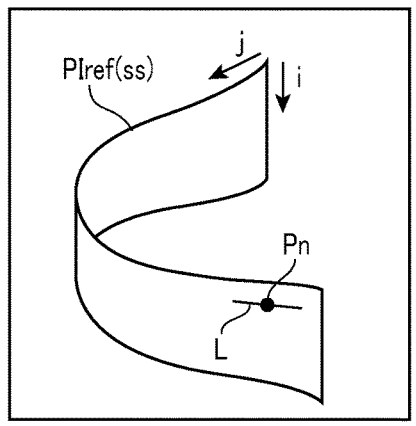
(C)
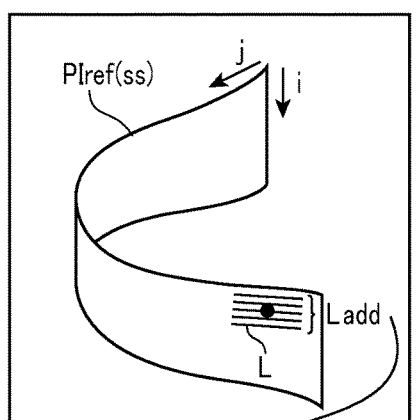
(D)
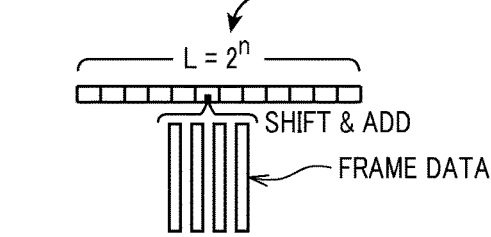

ENLARGEMENT FACTOR: SMALL

ENLARGEMENT FACTOR: LARGE

ENLARGEMENT FACTOR: SMALL

ENLARGEMENT FACTOR: LARGE (WHEN TOOTH IS PRESENT ALONG REFERENTIAL TOMOGRAPHIC PLANE)

$\theta_1, \theta_1'$ ; ENLARGEMENT FACTOR: SMALL $\theta_2, \theta_2'$ ; ENLARGEMENT FACTOR: LARGE

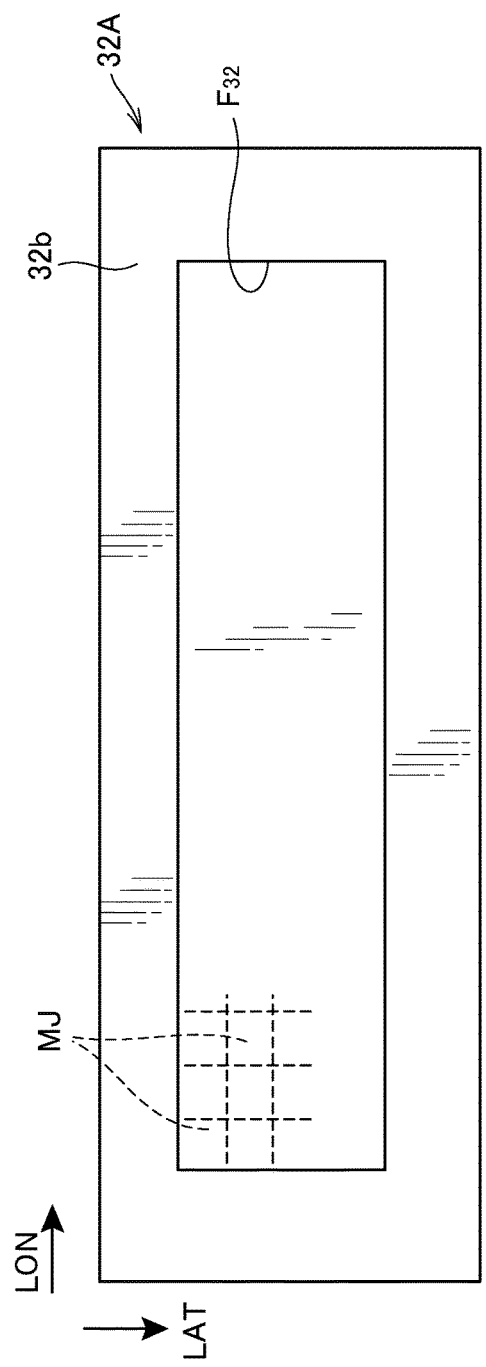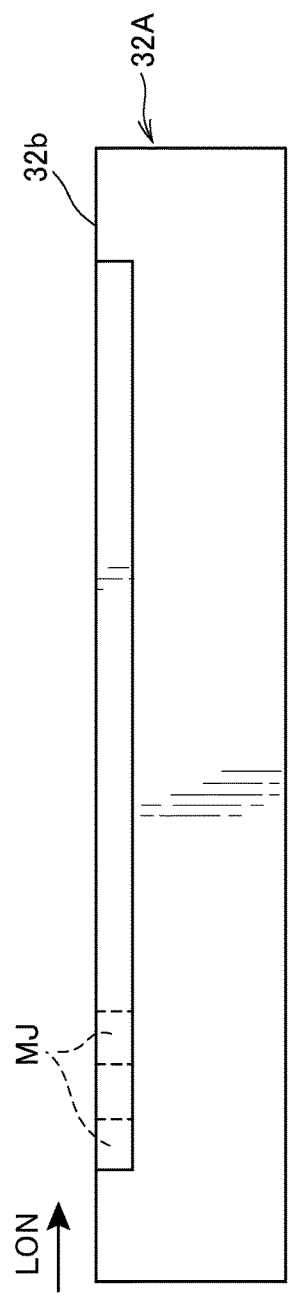

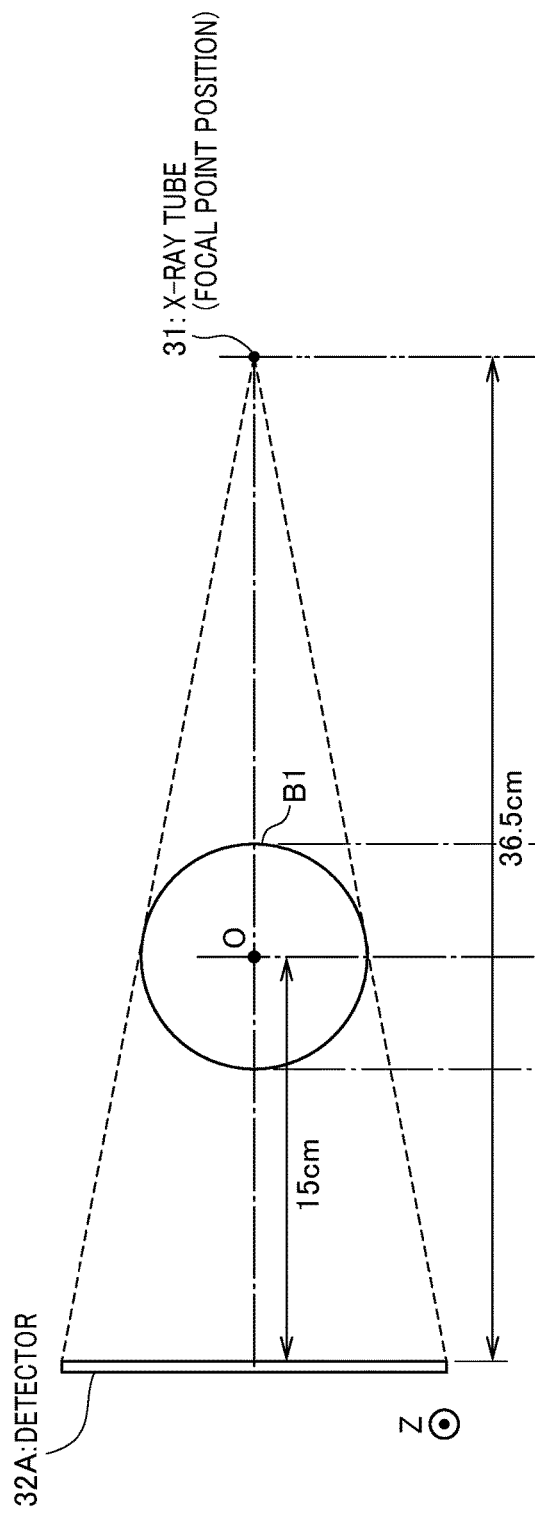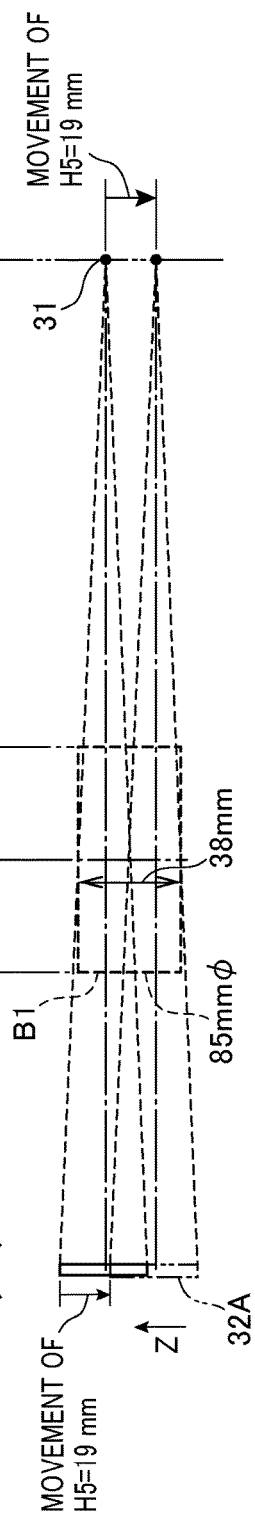
FIG.67(A)
FIG.67(B)

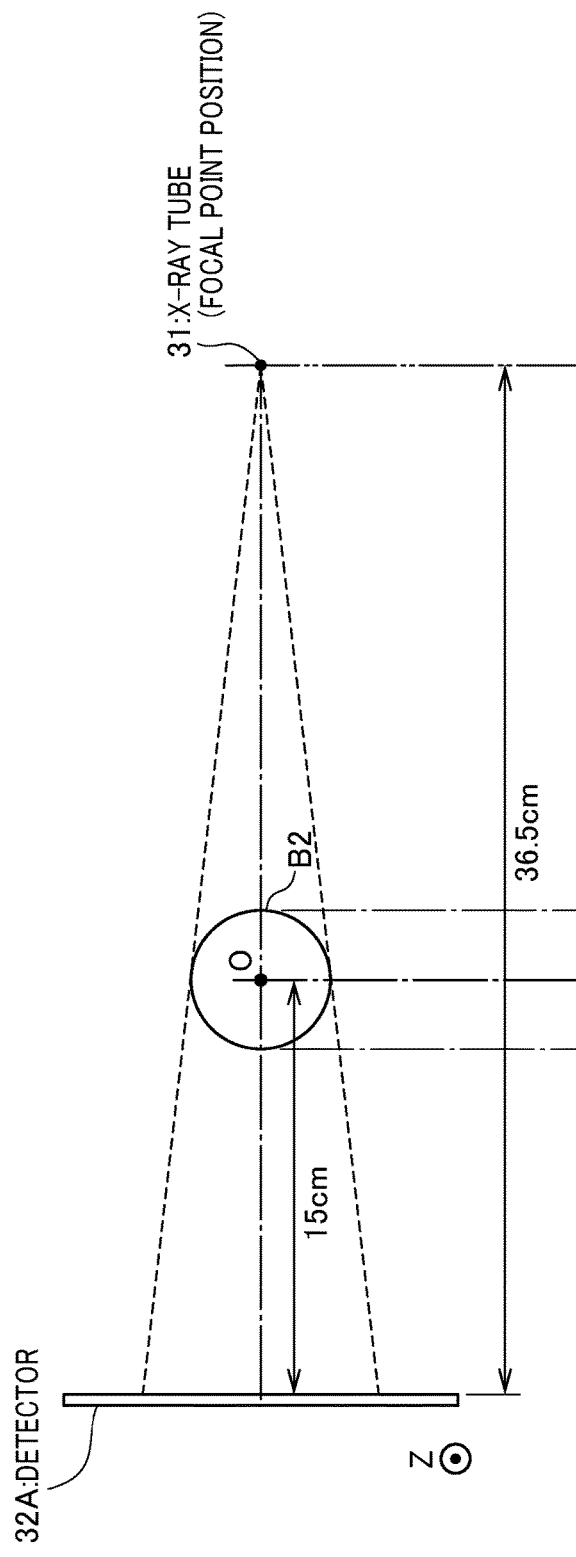
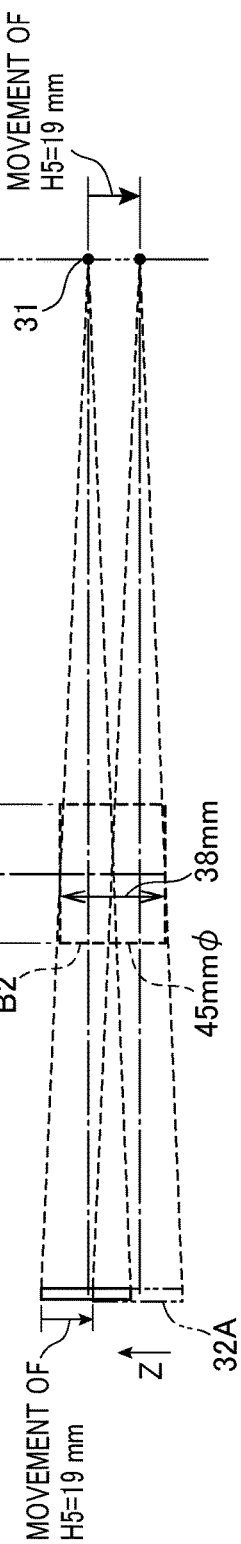
FIG. 68(A)
FIG. 68(B)

X-RAY TOMOGRAM IMAGING DEVICE

CROSS-REFERENCE TO RELATED APPLICATIONS

This application is a 371 U.S. National Stage of International Application No. PCT/JP2011/065987, filed Jul. 13, 2011. This application claims the benefit of Japanese Patent Application No. 2010-158542, filed Jul. 13, 2010. The disclosures of the above applications are incorporated herein by reference.

FIELD OF THE INVENTION

The present invention relates to an X-ray tomographic imaging apparatus that uses X-ray beams to image tomographic to images of an object being imaged, and in particular, to the X-ray tomographic imaging apparatus that images three-dimensional tomographic images of an object based on a tomosynthesis technique.

BACKGROUND ART

In recent years, tomographic imaging using a tomosynthesis technique has been used actively. The theory of this tomosynthesis technique has been known long before (for example, refer to patent literature 1), and recently, tomographic imaging that enjoys ease of image reconstruction performed using the tomosynthesis technique has been proposed (for example, refer to patent literatures 2 and 3). Especially, many such cases can be found in dental and mammographic fields (for example, refer to patent literatures 4, 5, 6, and 7).

Conventionally, as one of radiation imaging apparatuses that employ the tomosynthesis technique by choice, there is a dental panoramic imaging apparatus. In this panoramic imaging apparatus, since an X-ray detector (hereinafter, referred to as a detector) has a limitation in its movement, the apparatus is designed to focus on a tomographic plane (which is referred to as a referential tomographic plane) according to a trajectory which is set mechanically in an imaging space. The imaging space refers to a space in which there is an X-ray path connecting the X-ray tube and the detector which are rotated around the jaw of a patient.

Therefore, only when the tooth row exists at and along the referential tomographic plane in the imaging space, the focuses of produced images are optimized best. However, if the tooth row is out of alignment from the referential tomographic plane, images are produced with poor focusing, so that the images blur. From this point of view, when it is desired to observe blurred portions of produced images at higher resolution, positioning of the patient is performed again to focus the blurred portions more clearly and data are acquired again, or, the blurred portions are subjected to intraoral imaging to obtain clearer images.

Meanwhile, in recent years, an X-ray panoramic imaging apparatus described in a patent reference 8 has been developed, in which a detector capable of acquiring X-ray detection data at a faster speed (for example, 300 FPS) is used and all the detection data are taken into a computer to apply the tomosynthesis technique to the detection data. In this apparatus, the detection data are processed based on the tomosynthesis technique to produce panoramic images of tomographic planes. In this apparatus, the position of a tomographic plane can be changed in the front-back direction of the plane and a panoramic image of the changed tomographic plane can be produced. For this image production, information indicative of distances of plural tomographic planes which are spatially parallel to the detection section of the detection (such information is called shift & add quantities or gains) is obtained by using a phantom or by theoretical calculation. For imaging, a pair of the X-ray tube and the detector is rotated around the patient's jaw, during which data are acquired. The central position of this rotation approaches to the tooth row and departs from it during the imaging. The acquired data are then subjected to software processing based on the tomosynthesis technique that uses the foregoing distance information, which provides images with less blur.

In addition, as shown by a patent reference 9, there has been known an apparatus which is composed of a single apparatus body, but is capable of selectively performing panoramic imaging and CT imaging

PRIOR ART REFERENCE

Patent Reference

[Patent Reference 1] JP-A-S57-203430
[Patent Reference 2] JP-A-H06-88790
[Patent Reference 3] JP-A-H10-295680
[Patent Reference 4] JP-A-H4-144548
[Patent Reference 5] U.S. Pat. No. 5,428,660 B
[Patent Reference 6] JP-A-2008-110098
[Patent Reference 7] US 2006/0203959 A1
[Patent Reference 8] JP-A-2007-136163
[Patent Reference 9] JP-A-H11-318816

DISCLOSURE OF THE INVENTION

Issues to be Solved by the Invention

However, the panoramic imaging apparatus, which is provided as the foregoing radiation imaging apparatuses, is still confronted with a difficulty which is due to an issue concerning with an amount of X-ray exposure. In general, when being compared with X-ray intraoral imaging apparatuses and dental CT scanners, the panoramic imaging apparatus can perform imaging with less X-ray exposure amounts. However, the panoramic imaging apparatus cannot be used as an alternative to the X-ray intraoral imaging apparatus, due to its lower resolution. For these reasons, it is still the case that careful examination of tooth rows is mainly carried out by the X-ray intraoral imaging apparatus and/or CT scanner. By the way, the conventional panoramic imaging apparatus gives a dose equivalent of radiation which is higher than "1.3 mSv per 3 months." It is therefore needed to install the panoramic imaging apparatus within a radiation controlled area in the same way as the X-ray intraoral imaging apparatus and the CT scanner.

Hence, performing a panoramic imaging requires a patient to move from the doctor's office, where the patient is seated on a treatment chair, to an imaging room which is a radiation controlled area. For example, when a reamer is used to detect the distal edge of the root of a tooth, it is therefore necessary that a patient with the reamer inserted in the patient mouth move from the doctor's room to the imaging room for panoramic, intraoral or CT imaging. This movement is a bother for the patient as well as the dentist. It is currently impossible to positionally confirm, from an X-ray image, the distal edge of the root of a patient's tooth with the use of a reamer in a state where the patient is still seated (lying down) on the treatment chair. For this reason, it has been pointed out that, though being admitted as being a useful modality, the dental panoramic imaging apparatus is insufficient in usability.

Additionally, an X-ray imaging room has to be prepared as a special room. This makes a facility larger in its size, thereby failing to meet a demand that X-ray imaging desired to be performed easily with less space.

As stated above, conventional various types of panoramic imaging apparatuses have now been improved in X-ray exposure. However the reality is that such apparatuses are suffering from images with less resolution, and it is therefore difficult to use the apparatuses as an alternative to the X-ray intraoral imaging apparatus.

The present invention is has been made in view of the foregoing situations, and it is an object to provide an X-ray tomographic imaging apparatus having the capability to provide tomographic images with higher resolution, with good usability such that the radiation controlled area is remained narrower and reconstructed tomographic images can be observed during dental work.

Means for Solving the Issues

In order to achieve the object, the present invention provides, as its main mode, an X-ray tomographic imaging apparatus, characterized in that the apparatus comprises: a data acquiring device comprising: an X-ray tube radiating X-rays whose intensities are dependent on an amount of current to be supplied thereto; a detector provided with a detection section in which a plurality of pixels are arranged two-dimensionally, the pixels detecting the incoming X-rays and outputting, frame by frame, digital electric data; support means having the capability to provide a curved orbit and support the X-ray tube and the detector such that the X-ray tube and the detector are movable along the orbit independently of each other, moving means having the capability to move the X-ray tube and the detector along the orbit independently of each other such that the X-rays are transmitted through an object being imaged, at desired angles and at respective positions in a scanning direction of a desired tomographic plane of the object, wherein the object is located inside the orbit provided by the data acquiring device; panoramic image procuring means having the capability to apply a tomosynthesis technique to the data acquired by the data acquiring device to produce a panoramic image of the tomographic plane based on the data; and tomographic image producing means having the capability to produce a tomographic image based on the data acquired by the data acquiring device and the panoramic image produced by the panoramic image producing means, structural components existing in the object being optimally focused in the tomographic image and distortions due to differences in angles of paths of the X-rays being suppressed in the tomographic image.

As a preferred embodiment, the X-ray tomographic imaging apparatus includes CT (Computed Tomography) image reconstructing means for reconstructing tomographic images, based on a CT reconstruction method, from the frame data acquired by the detector, the movement means is configured to move, along the orbits, the X-ray tube and the detector which are directly opposed to each other, and switching means for switching an attitude of the detector when CT imaging is desired to be performed instead of the tomosynthesis method.

Effects of the Invention

In the X-ray tomographic imaging apparatus according to the present invention, it is possible to provide tomographic images of higher resolution, while the apparatus can present high usability such that a radiation controlled area can be smaller and reconstructed tomographic images can be observed under treatment work of a dentist.

Particularly, applying this X-ray tomographic imaging apparatus to a dental X-ray extraoral imaging apparatus provides various advantages, including that a larger X-ray imaging room, i.e., the radiation controlled area is not necessary, dental panoramic images can be captured under treatment work with the patient seated (or lying down) on the treatment chair, which provides excellent usability. It is also possible to provide higher-resolution panoramic images which can be used as an alternative to image from the X-ray intraoral imaging apparatus. Additionally, panoramic imaging and CT imaging can be performed selectively, providing dual imaging functions by a single apparatus, leading to higher versatility.

BRIEF DESCRIPTION OF THE DRAWINGS

In the accompanying drawings:

FIG. 21(A) and 21(B) are views explaining the principle of reconstruction of a panoramic image according to the present invention;

FIG. 24(A)-24(C), are illustrations explaining steps for measuring a displacement of the radiation (projection) angle of an X-ray beam;

FIG. 25 shows an illustration explaining a displacement in the radiation angle of the X-ray;

FIG. 40(A) is a view explaining, in the order of (A) to (D), the process to identify optimally-focused tomographic planes for each of positions on the 3D reference image;

FIG. 60(A), (B) are a plan view and a side view of the detector used in the second embodiment;

FIG. 67(A), (B) are views explaining imaging regions and movements of the X-ray tube and the detector in the body axis direction when the whole tooth rows are subjected to CT imaging; and FIG. 68(A), (B) are views explaining imaging regions and movements of the X-ray tube and the detector in the body axis direction when part of tooth rows is subjected to CT imaging.

DETAILED DESCRIPTION OF PREFERRED EMBODIMENTS

With reference to the accompanying drawings, embodiments of the present invention will now be described.

[First Embodiment]

Figure 1:
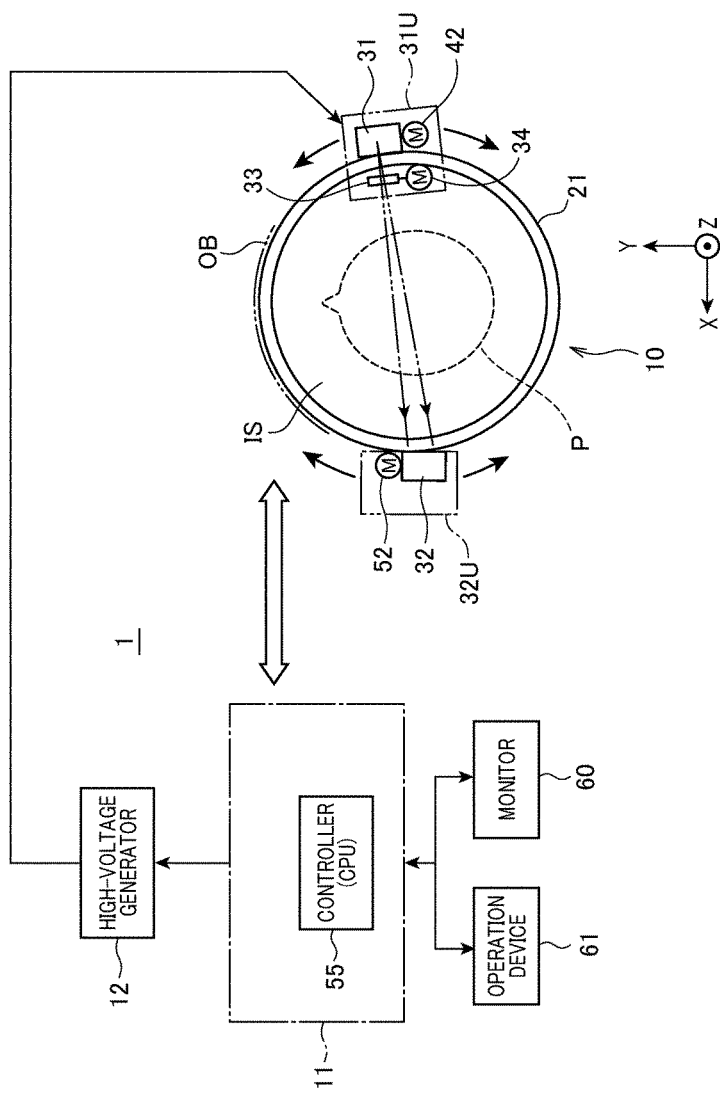
FIG. 1 is a view outlining the whole configuration of an X-ray extraoral imaging apparatus employed as a radiation tomographic imaging apparatus according to a first embodiment of the present invention.
Figure 54:
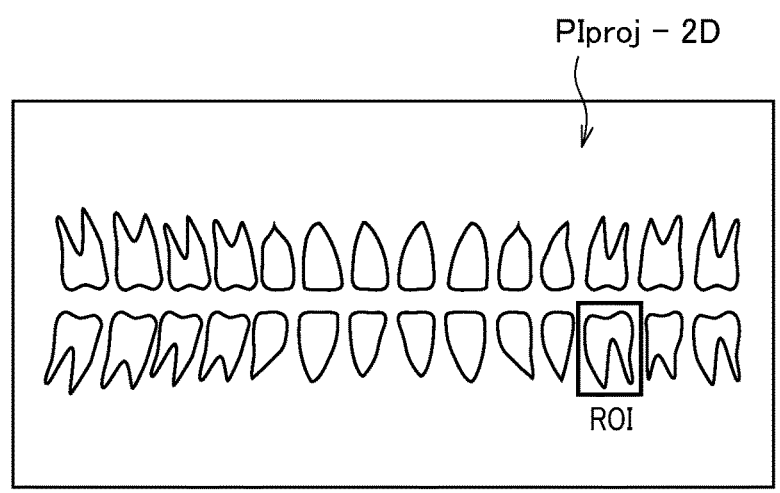
FIG. 54 is a view pictorially explaining a 2D reference image and a ROI which is placed thereon.

With reference to FIGS. 1-54, a first embodiment of a dental X-ray extraoral imaging apparatus, which is provided as an X-ray tomographic imaging apparatus according to the present invention, will now be described.

The present extraoral imaging apparatus is a modality capable of scanning an object (such as a tooth row) of the jaw of a patient P from outside the jaw with X-ray beams, processing data, acquired by scanning, with a tomosynthesis technique such that tomographic images of the object are produced. The X-ray extraoral imaging apparatus according to the present embodiment can provide images higher-resolution images which have not been provided by the conventional panoramic imaging apparatus, while the apparatus is still kept smaller in size and light in weight, in addition to performing the function of panoramic imaging apparatuses which are currently used for dental treatment. Further, employing this apparatus will improve an inconvenient workflow resulting from use of an imaging room provided as the radiation controlled area. All of these matters will lead to achieving the object of the present invention.

<Basic Configuration>

In the present embodiment, the basic configuration of the X-ray extraoral imaging apparatus of the embodiment will firstly be described. Various practical examples showing installation of this X-ray extraoral imaging apparatus will now be described as modifications.

FIG. 1 shows the basic configuration of an X-ray extraoral imaging apparatus 1 according to the embodiment. This X-ray extraoral imaging apparatus 1 is a medical modality which provides panoramic images showing an internal structure of the jaw with the tooth row of an object P from the outside of the oral portion of the object P (patient) and also provides a three-dimensional (3D) tomographic image based on the panoramic images.

The X-ray extraoral imaging apparatus 1 includes, as its basic components, a scan device 10 to acquire X-ray transmission data by scanning the jaw portion with the X-ray beams, a computer 11 to control scan operations of the scan device 10 and reconstruct images using the X-ray transmission data acquired by the scan device 10, and a high-voltage generator 12 to supply high voltage power to the scan device 10. The term "scan" referred in this embodiment is an action which radiates X-rays (X-ray beam XB) to a portion to be imaged of the object P along respective preset plural paths and acquire a set of X-ray transmission data necessary for image reconstruction.

Figure 3:
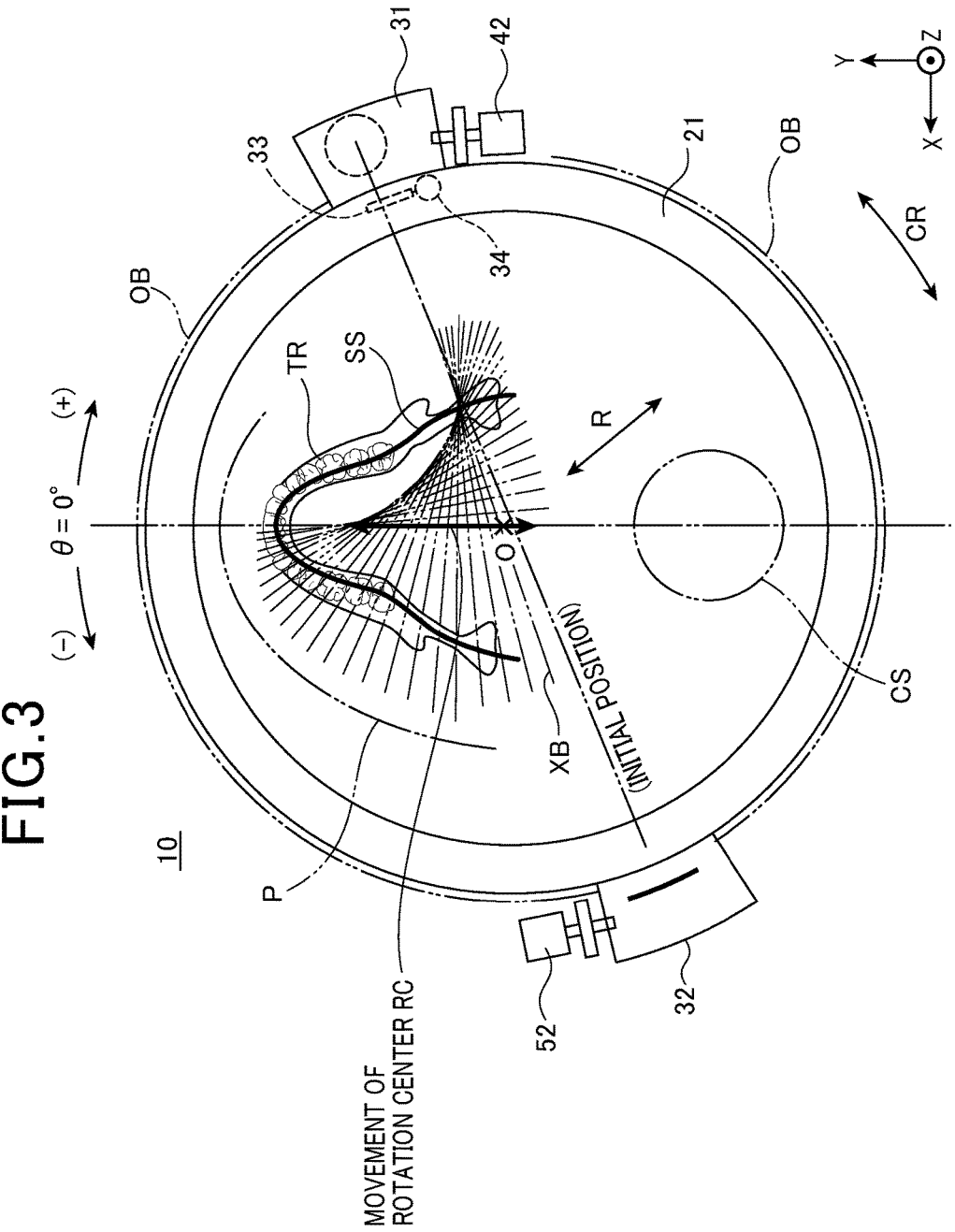
FIG. 3 is a view explaining the principle of an orthogonal imaging technique employed in the X-ray extraoral imaging apparatus.

The scan device 10 is installed in various modes as will be explained later by modifications, where the scan device is located closer to the jaw (portion to be imaged) of the object P so as to surround the jaw. Practically, as shown in FIGS. 1 and 3, the scan device 10 includes a circular ring member 21 to provide a circular orbit (path, or trajectory) OB. The orbit OB is circular and imaginarily created along the outer circumferential surface of the ring member 21.

In scanning, this ring member 21 is located around the jaw of the object P. The location is achieved in various manners. For example, as explained in a later-described modification, the ring member 21 may be fixedly or detachably attached to the headrest of a dental treatment chair. The ring member 21 may be supported by a C-shaped arm prepared separately from the treatment chair. Furthermore, the ring member 21 may be supported by a holder which can be mounted on the shoulders and/or the head of a patient P. In short, the ring member 21 is located around the jaw portion of a patient P when scanning is performed, and it is desired to use the ring member 21 of which diameter is reduced as smaller as possible to be compact in size, in terms of reducing an X-ray amount necessary for scanning.

Incidentally, as shown in FIG. 1, an orthogonal coordinate system of X-, Y- and Z-axes is set to the ring member 21, where the ring member 21 presents the orbit OB and a two-dimensional plane along the orbit gives an XY plane to the coordinate system. As need arises, these coordinate axes are used for explanations.

The ring member 21 has, as described, the imaginary circular orbit OB along its outer circumferential surface. Additionally, the ring member 21 is used for scanning, so that the ring member is equipped with an X-ray tube unit 31U which contains an X-ray tube 31 and a detector unit 32U which contains a detector 32. Both units are supported movably along the orbit OB. On the outer circumferential surface of the ring member 21, there is formed, for example, a bearing (not shown) in its circumferential direction.

The X-ray tube unit 31U contains, in addition to the X-ray tube 31, a movement mechanism 41, such as worm gear, to move the unit 31U along the orbit OB and an electric motor 42 to drive the movement mechanism 41. Moreover, in this embodiment, the X-ray tube unit 31U is additionally equipped with a collimator 33 and a drive member 34, such as ultrasonic motor and screw members, to relatively move the collimator 33 to the X-ray tube 31.

The X-ray tube 31 and the detector 32 are rotated during which X-ray scanning is performed. Hence, there is formed an imaging space IS in an inner space surrounded by the circular orbit OB presented by the ring member 21.

The X-ray tube 31 is for example a rotating anode type of X-ray tube or a pulse drive type of X-ray tube that uses a field-emission-type carbon nanotube cathode, where X-rays are radially emitted from its target (anode) toward the detector 22. The focal point on the target (that is, the focal point of the X-ray tube), onto which electron beams impinge, is 0.25 mm or less, which is small enough so that the X-ray tube 21 acts as a spot-like X-ray source.

At a given position in front of the X-ray tube 21, the collimator 33 is positioned which has a slit-shaped aperture. The X-rays radiated from the X-ray tube 21 pass through the aperture of this collimator 33. Hence, the X-rays entering the detector 32 can be collimated in conformity with its detection section (i.e., its actual acquiring window (for example, a window whose width is 5.0 mm)). The collimator 33 is driven to move its position and its attitude or its position alone. The collimator 33 and the drive member 34 are both installed inside the X-ray tube unit 31U so as to move together with the X-ray tube 31.

Similarly to the X-ray tube unit 31U, the detector unit 32U contains a drive member 51 and an electric motor 52 in addition to the detector 32 to detect X-rays. The drive member 51, which employs a worm gear and other components, is used to move the unit 32U along the orbit OB and the motor 52 is used to move the drive member 51.

Meanwhile the detector 32 is a device acting as radiation detecting means, where there is provided a digital type of X-ray detector which has a detection section formed by mapping X-ray detecting elements two-dimensionally (for example, in a matrix of 64×1500). This detector 32 detects incoming X-ray beams into its detection section. By way of example, the detector 32 has a long detection section (e.g. 6.4 mm in width and 150 mm in length), which is made of CdTe. Since the embodiment uses a tomosynthesis technique as an image reconstruction method, it is necessary that the detector 32 have plural X-ray detecting elements in its lateral (width) direction as well as its length direction.

The detector 32 is arranged such that its longitudinal direction agrees with the Z-axis direction. The detector 32 has an effective width in its lateral direction (a direction along the XY plane), which is effective in the X-ray detection, is set to approx. 5.0 mm by the foregoing collimator 33, though this value is just an example. This detector 32 has the capability to directly convert incoming to X-ray beams to digital electric signals depending on amounts of the X-ray beams, at a fast frame rate of 300 fps for example (where one frame consists of 64×1500 pixels for example). Such digital electric signals can be acquired frame by frame as image data. Hereinafter this acquired data is called "frame data."

The electric motors 42 and 52 and the drive member 34 are drivable independently of each other in response to drive signals from transmitted from the collimator 11. Hence, the X-ray tube and detector units 31U and 32U are movable independently of each other along the orbit OB. Further, in the X-ray tube unit 31U, the collimator 33 is configured to be movable relatively to the X-ray tube 31, but in an independent manner. As an alternative, if necessary, the collimator 33 can be omitted from the above construction. The drive signals from the computer 11 to the electric motors 42, 52 and the drive member 34 may be transmitted via wires or without wires.

Incidentally the X-ray tomographic imaging apparatus according to the present invention is not always limited to the dental X-ray extraoral imaging apparatus, but the apparatus can be applied to any apparatuses which use the tomosynthesis technique to three-dimensionally observe the actual shapes (positions) of objects. For example, for medical use, the present invention can be applied to the following apparatuses.

(1) Scan imaging apparatus for bones such as arms and legs:

There is provided an apparatus capable of imaging an arm or leg inserted into a rotation member. The apparatus is provided with a photon-counting type of X-ray detector and components to radiate two kinds of energies of X-rays, so that imaging and bone mineral analysis can be performed in parallel. In the system, the ring member is configured as a circular dome member which is movable in its longitudinal direction, changing volumes to be scanned.

(2) Lung cancer screening apparatus:

The apparatus adopts, as the ring member, a circular dome member into which a patient's chest region is inserted. A detector covering the chest portion is employed for scanning, being able to reconstruct images of multiple tomographic planes by one shot.

(3) Mammography scanner:

This scanner uses, as the ring member, a circular dome member in which a patient's breast portion is positionally set, so that images of multiple tomographic planes are reconstructed by one shot of scanning.

(4) Scanner for checking geometry of skull bone:

This scanner also employs, as the ring member, a circular dome member into which a patient's head is positioned, to three-dimensionally model of the surface layer of the skull bone.

(5) Cephalometic scanner:

This scanner uses, as the ring member, a circular dome member in which a patient's head is positioned. An image reconstruction is performed along a tomographic plane for examining cephalometry. This scanner provides images with less distortion due to differences in enlargement factors. This scanner can be used for diagnosis in orthopedic surgery and cosmetic surgery.

(6) Apparatus for examining dead body:

This apparatus is structured with less weight and being portable, which enables imaging of the tooth rows of a dead body. Hence, it can be used to identify the dead body. Therefore, the tooth row structure can be analyzed three-dimensionally and finely, so that highly accurate dead-body identification can be expected.

(7) X-ray apparatus for examining animals (pet animals):

This apparatus is provided as a dome-shaped apparatus for X-ray examining animals. Since the imaging region can be selected freely, most examinations can be done with this apparatus.

As an alternative, the apparatus explained in the foregoing items (1) and (3) and the X-ray extraoral imaging explained in the present embodiment can be home use by making the apparatus into a lightweight and portable one. If the apparatus is mounted on vehicles, it can be used in local areas in which there no dental care facilities.

On the other hand, for nondestructive test, the present invention can be applied to the following apparatuses.

(8) Apparatus for inspecting inner structures:

This apparatus can be used for inspecting inner structures of objects such as small packages, metals, foods, flexible printed circuit boards, and IC. This apparatus adopts an inspection dome in which an object is placed, so that any three-dimensional section can be subjected to reconstructing images. Hence, the three-dimensional structure of objects can be seen depending on object characters. It is also identify types of subjects by employing a photon-counting type of detector or utilizing two types of energies of X-ray beams.

(9) Baggage screening apparatus at airports:

This apparatus employs an inspection dome into which pieces of baggage is fed into the inspection dome piece by piece for scanning therein. This provides a system capable of screening baggage at lower levels of X-ray amount and in a speedy manner, compared to the CT scanner.

(10) Inspection apparatus for assembled object:

This apparatus is used to three-dimensionally inspect the structure of an object assembled and arranged in three dimensions. Designating a reconstruction plane freely makes it possible to inspect an inner structure of a designated portion of the object.

(11) X-ray inspection apparatus for paintings:

This apparatus is intended to inspect inner portions of paintings with odd-shaped surfaces. This apparatus uses a dome which is larger to some extent.

In this way, though it can be developed into various applications, the present embodiment exemplifies the X-ray extraoral imaging apparatus.

Figure 2:
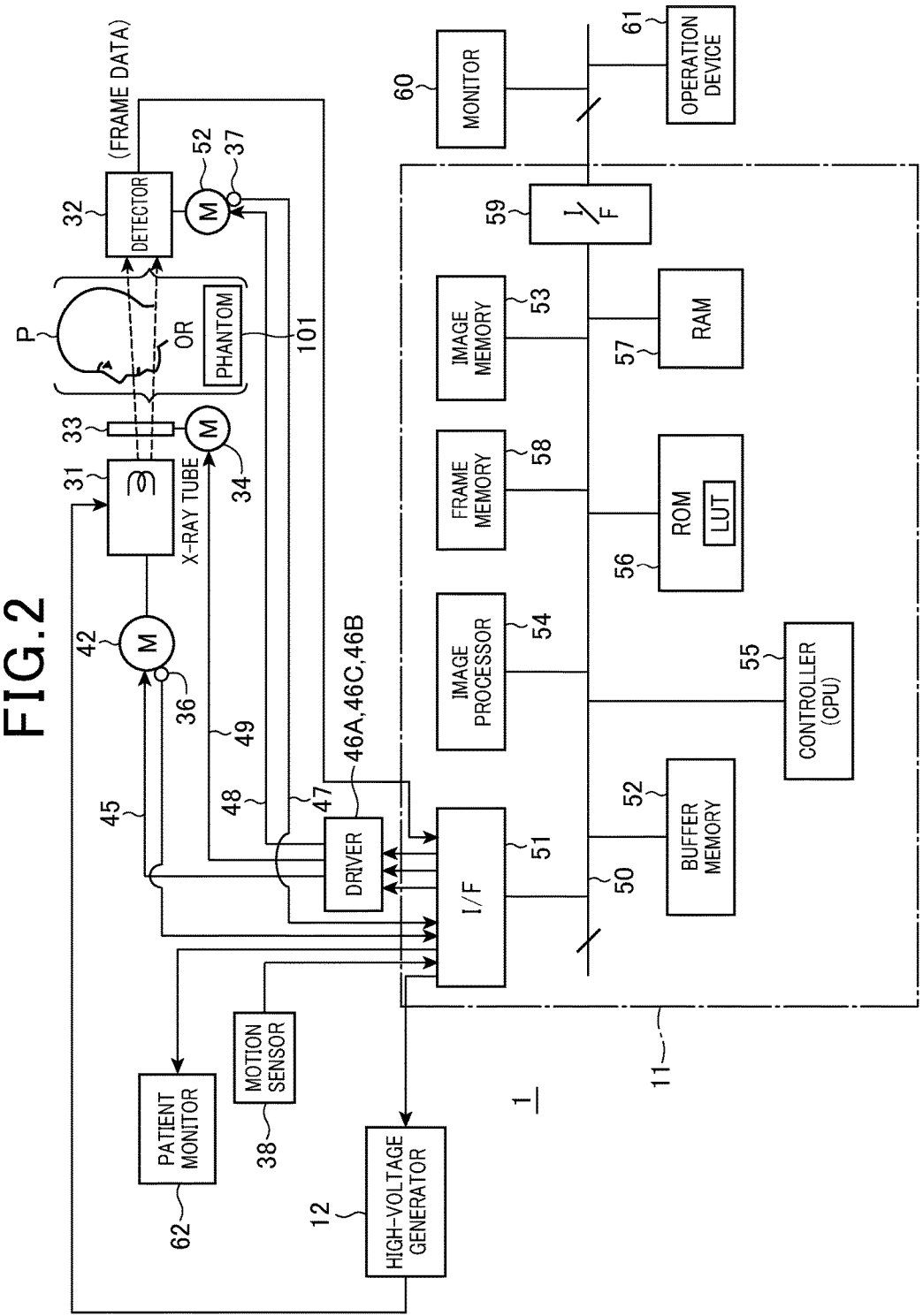
FIG. 2 is a block diagram showing an outlined electric configuration of the X-ray extraoral imaging apparatus according to the embodiment.

Now with reference to FIG. 2, where there is shown an electric block diagram showing control and processing for the X-ray extraoral imaging apparatus 1.

As shown, the X-ray tube is electrically connected to the high-voltage generator 12 to receive high-voltage power for X-ray radiation. The electric motor 42 to move the X-ray tube 31 is electrically connected to a driver 46A via a control line 45, and the driver 46A is connected to the computer 11. The detector 32 is connected to the computer 11 via an acquisition line 47. The electric motor 52 to move the detector 32 is electrically connected to a driver 46B via a control line 48, and the driver 46B is connected to the computer 11. Moreover, the drive member 34 to move the collimator 33 is also electrically connected to a driver 46C via a control line 49, and this driver 46C is connected to the computer 11. The high-voltage generator 12 reacts to signals supplied from the computer 11 to control operations of the X-ray tube 31 depending on X-ray radiation conditions, such as tube current and tube voltage, and a timing sequence instructing X-ray radiation.

The computer 11 is composed of for example a personal computer which has the capability to store therein a large amount of image data, as it is required to handle large amounts of image data including acquired frame data. Practically the computer 11 includes, as its main components, an interface 51, a buffer memory 52, an image memory 53, an image processor 54, a controller (CPU) 55, a ROM 56, a RAM 57, and a frame memory 58, which are communicably connected to each other via an inner bus 50. Additionally the computer 11 also includes another interface 59, which is used to communicably connect a monitor 60 and an operation device 61 to the computer. Additionally, the interface 51 is connected to a patient monitor with which not only panoramic images but also images explained by a doctor can be provided to a patient.

The buffer memory 52 temporarily memorizes digital frame data coming from the detector 32 via the interface 51.

The image processor 54, which is under control of the controller 55, performs production of a panoramic image along a later-described 3D referential tomographic plane SS and processing for post use of the panoramic image in an interactive manner with an operator. Programs for realizing such functions are previously stored in the ROM 56. Hence, the ROM 56 functions as a recording medium for storage of such programs. In the ROM 56, there is formed a LUT (look-up table), in which correction characteristics for tube current I and a reference function used to calculate rotation angles θ of the X-ray tube 31 and the detector 32, which will be described later, are previously stored. These programs may be stored in the ROM 56 beforehand, but depending on situations, may be installed from an external system to a work area of the controller 55 via the RAM 57 by using a communication line or a potable memory.

The frame data and image data, which are to be processed or which are being processed by the image processor 54, are stored in the image memory 53 in a readable and writable manner. As the image memory 53, a recording medium having a large capacity (nonvolatile and readable/writable), such as a hard disk, is used. The frame memory 58 is used for display of reconstructed panoramic image data, panoramic image data to be post-processed, and others. Image data stored in the frame memory 58 is displayed at intervals on the screen of the monitor 60.

The controller (CPU 55) is in charge of controlling operations of the components of the apparatus according to control and processing programs stored in the ROM 56 in advance. Such programs are designed to interactively receive from an operator operative information concerning with each control item. Thus the controller 55 has the capability to perform acquisition (scanning) of frame data and other actions, as explained later.

As shown in FIG. 1, the jaw of a patient P is located inside the scan unit 10, i.e., in the imaging space IS and ordered to be stationary there. In this located state, the scanning is started, and the X-ray tube 31 and collimator 33, and the detector 32 are started to rotate along the ring member 21, that is, along the orbit OB.

During the rotation, under control of the controller 55, the high-voltage generator 12 supplies to the X-ray tube 31 high-voltage power for radiation (specified tube voltage and current) at intervals in a pulsed mode, whereby the X-ray tube 31 is driven in the pulsed mode. The X-ray tube 31 thus radiates pulsed X-rays at intervals. For this pulse drive, a drive signal subjected to half-wave rectification may be used or a drive signal produced by a DC drive technique which uses an inverter may be used. The X-ray beams pass through the patient's jaw (tooth row portion) located at the imaging position and enters the detector 32. The detector 32 detects incoming X-ray beams to sequentially output two-dimensional, digital and electric frame data (e.g. 64×1500 pixels) corresponding to the incoming X-rays, at a faster frame rate (e.g. 300 fps). The frame data are then sent to the computer 11 via the communication line 47, where the frame data are temporarily stored in the buffer memory 52 via the interface 51. The frame data temporarily stored are then transferred to the image memory 53 for storage therein. The frame data are used to reconstruct two-dimensional panoramic images which have now been used for medical care and pseudo-3D panoramic images (transmission images) produced along the shape of the jaw, by using the tomosynthesis technique.

<Features of Breakthrough Configuration, Scan Control and Image Processing>

During imaging, the jaw of a patient Pi is located in the imaging space IS inside the ring member 21. X-rays radiated by the X-ray tube 31 are collimated by the collimator 33 to produce X-ray beams XB radiated toward the patient P. The X-ray beams XB pass through the jaw of the patient P to impinge into the detection section of the detector 32, where the X-rays are converted directly to digital electric signals by X-ray detecting elements arranged in the detection section. As a result, as described before, the frame data are outputted from the detector 32 at a higher frame rate.

The frame data are acquired intermittently at intervals (e.g. 300 pfs) during which the X-ray tube 31 (and collimator 33) and the detector 32 are moved along the circular orbit OB.

During this intermittent acquisition, the X-ray tube 31 and the detector 32 are rotated around the patient's jaw, while the attitudes thereof are controlled to be mutually obliquely or directly opposed with the jaw of the patient P kept to be located therebetween. This is one of the features of this imaging. "The X-ray tube 31 and the detector 32 are directly opposed to each other" is defined as a state where the path of the X-ray beam XB (i.e., the path of a beam spread when the X-ray beam is projected to the XY plane) radiated from the X-ray tube 31 is perpendicular to the detection section of the detector 32. Further, "the X-ray tube 31 and the detector 32 are obliquely opposed to each other" is defined as a state where the foregoing paths of the X-ray beam crosses with the detection section of the detector 32 at angles other than 90 degrees (0 degrees<degree<90 degrees).

Breakthrough configurations of the X-ray extraoral imaging apparatus according to the present embodiment, which have not been seen in the conventional apparatus, will now be described.

<Circular Orbit>

Like other medical modalities, it is requested that the dental panoramic imaging apparatus provide higher-resolution images, consume less power, and be compact in size and light in weight.

In order to achieve the compact size and light weight, the X-ray extraoral imaging apparatus is equipped with a scan member, that is, the scan device 10, which employs a circular orbit along which the X-ray tube 31 and the detector 32 are moved. Additionally, the ring member 11 has a diameter which is set to a smaller value as much as possible. A portion to be imaged is the jaw, or more precisely, the tooth row, so that it is sufficient that the ring member 11 has a size which is able to cover a patient' head. Accordingly, the ring member 11 is produced, for example, have an inner diameter of approx. 240 mm and an outer diameter of approx. 270 mm. This means that, just as an example, the diameter of the orbit OB is approx. 270 mm. Providing the orbit OB with a smaller diameter this way makes it possible that the X-ray tube 31 and the detector 32 which are moved, or rotated, along the orbit OB are positionally very closer to each other, compared with that of the scan member of the conventional panoramic imaging apparatus. Hence, the scan device 10 can be compacted in size and reduced in weight in comparison with the conventional.

In addition, since the X-ray tube 31 and the detector rotate on the same circular orbit OB, a distance between the center of the orbit OB, i.e., the rotation center O, and the X-ray tube 31 and a distance between the rotation center O and the detector 32 are equal to each other. However, the orbit according to the present invention is not necessarily confined to this geometry, the distance between the rotation center O and the X-ray tube and the distance between the rotation center O and the detector may be different from each other. In other words, the X-ray tube and the detector can be designed to rotate, respectively, along two different circular orbits whose diameters differ from each other. In this geometry, it is preferred that the two circular orbits be coaxial, due to easiness in design.

Furthermore, the distance between the X-ray tube 31 and the detector 32 becomes smaller. Hence, if it is assumed that a specified amount of X-rays is required for imaging, the X-rays radiated from the X-ray tube 31 can be reduced in its intensity. Practically, the X-ray intensity attenuates in proportion to the square of a distance. For a detector having the same width and pixel size, the attenuation corresponds to the cube of the distance. This means that a small amount of reduction in the distance will lead to a reduction in the X-ray intensity to be required.

As described, the distance between the X-ray tube 31 and the detector 32 is designed to be smaller than that of the conventional panoramic imaging apparatus, thereby reducing the current I of the X-ray tube 31 down to approx. 750 µA or thereabouts. This amount of current I is nearly 1/10 or less than the conventional. Because of this, a separate room (a radiation imaging room) functioning as the radiation controlled area, which is required for the conventional panoramic imaging apparatus, is not required in the embodiment. That is, the radiation controlled area is limited to the imaging space IS in which the X-ray tube 31 and the detector 32 rotate.

Practically, when the scan device 10 can be loaded to a patient P under treatment, tomographic images of the patient's tooth row can be acquired during the treatment (with the patient P still seated on the treatment chair, without making the patient move to a separate room). Of course, since the X-ray tube current I is reduced, an amount of X-ray exposure is also reduced depending on a reduction in the current. It is therefore possible to use various imaging modes with less operator's experience. For example, it is possible that a pre-scan is first made for rough whole imaging of a patient's jaw, and the angle of the jaw is adjusted by controlling the headrest, and a desired treatment portion is scanned accurately for the next imaging.

<Tube Focal Point, Detector>

On the other hand, only reducing the X-ray tube current I will result in images of poorer resolution, with no production of finer tomographic images proper for actual use. In consideration of this fact, the present embodiment employs the X-ray tube whose focal point is designed to be 0.25 mm or less and the direct-conversion type of digital detector as the detector 32 so that the frame data are acquired at a faster rate.

<Orthogonal Imaging and Independent Drive>

In the present X-ray extraoral imaging apparatus 1, images of tomographic planes along the horseshoe-shaped tooth row of a patient's jaw are reconstructed using the tomosynthesis technique. As shown in FIG. 3, the tooth row TR is not positioned at the geometrical center O on the XY plane of the scan device 10, and biased toward the front of the jaw. Additionally, there exists a cervical spine CS behind the tooth row TR, where the cervical spine becomes an obstacle to scanning. Even viewing the tooth row TR, there exist overlaps between teeth. Hence, the paths of X-ray beams XB are selected at every X-ray radiation angle θ with a view that the overlaps cannot be imaged and the cervical spine CS is avoided from the paths to secure that the paths pass across only the tooth row, as much as possible. This path selection gives each radiation angle θ a path passing across the tooth row TR in an orthogonal state or an approximately orthogonal state.

Incidentally, "orthogonal" intends to mean that an X-ray beam desired to pass between teeth, and does not intend to mean 90 degrees. Scanning performed along this kind of paths is referred to orthogonal imaging. With this regard, the paths of the X-ray beam XB are set as shown in FIG. 3, for instance.

FIG. 3 shows the X-ray tube 31, the detector 32, the tooth row TR of the jaw of a patient P, and positional relationships between the 3D (three-dimensional) referential tomographic plane SS along the tooth row TR and the paths of the X-ray beam XB at each of the X-ray radiation angle (scanning angle) θ, where all the elements are shown by being projected onto the XY plane. The 3D referential tomographic plane SS is defined as being 3D from a pseudo-3D view point, because the plane SS, which is a referential tomographic plane, is not a simple flat plane, but curbed and spread three-dimensionally. In addition, the "X-ray beam" is a beam of X-rays radiated by the X-ray tube 31 and collimated by the collimator 33. The (path) direction of the X-ray beam (i.e., the X-ray radiation angle) is referred to as the direction of a line connecting the focal point of the X-ray tube 31 and the center position of X-ray beams entering the detection section of the detector 31 (i.e., the center position projected to the XY plane in FIG. 3). The position and direction of each X-ray beam path are designed to be different from each other at respective positions along the tooth row TR.

When the tooth row TR is projected to the XY plane, its contour (shape) depends on individuals. For this, the present embodiment employs a statistically standard contour. This statistically standard contour is nearly horseshoe shaped and also known from, for example, a paper "R. Molteni, "A universal test phantom for dental panoramic radiography" MedicaMudi, vol. 36, no. 3, 1991." The 3D referential tomographic plane SS is set along this contour. This plane SS is a section (imaginary plane) which extends from the shown line in the Z-axis direction so that the section has a pseud three-dimensional spread. In the present embodiment, this plane SS is prepared beforehand, but, for imaging, may be selected from a plurality of tomographic planes previously prepared in the apparatus. That is, the plane SS is a fixed section, but such a selection allows the plane SS to positionally movable within a specified range in the depth (front-back) direction of the tooth row.

This statistically standard tooth row TR is employed, and, as shown in FIG. 3, at any position along the tooth row TR, the path of the X-ray beam XB is set to be perpendicular or thereabouts as much as possible to the contour and to avoid passing through the cervical spine. In consideration of these factors, the path direction at each X-ray radiation angle θ is decided. In the present embodiment, in setting the paths of the X-ray beams XB, a high priority is put on preventing influences from teeth overlaps and noise from the cervical spine. To the X-ray tube unit 31U and the detector unit 32U, the X-ray radiation angle θ corresponds to the rotation angle. Hence, the angle θ means the X-ray radiation angle, the rotation angle, and the san angle, and is thus selectively used depending on explanations.

Incidentally, the foregoing technique for setting the paths of the X-ray beams XB, which gives greater importance to the orthogonal imaging shown in FIG. 3, is exemplified as a representative technique to set desired path positions. This does not always mean that the paths of the X-ray beam XB are precisely perpendicular to the tooth row at respective positions along the tooth row. Additionally, this does not always mean to exclude path setting methods other than the foregoing one for the orthogonal imaging.

In the paths of the X-ray beams XB which are set for the orthogonal imaging, the X-ray tube 31 (with the collimator 33) and the detector 32 are directly opposed to each other at the central position in the anterior teeth among the tooth row TR, as shown in FIG. 3. Concretely, the path of the X-ray beam XB passes through the geometrical center O of the ring member 12. As the X-ray beam path moves toward a right or left molar area from the central position of the anterior teeth, the path is gradually displaced from the geometrical center O. As the path moves more deeply in the molar area, the path comes closer to the center O. In this embodiment, the path again passes through the center O. An extent until which the X-ray beam path moves depends on a scan range φ (for example, φ=190 to 210°=±85° to ±105°).

In this way, in the present embodiment, the paths of the X-ray beams XB are set according to the shape of the tooth row TR (object being imaged) in preference to the geometrical center O, so that the "orthogonal imaging" can be performed. To obtain this feature, the X-ray tube 31 (and collimator 33) and the detector 32 are rotatable along the circular orbit OB independently of each other and the collimator 33 is movable relatively to the X-ray tube 11.

<Measures for Preventing Irregularities in Density>

However, the foregoing is not always sufficient in the sight of irregularities in density of an image. In the foregoing configurations, the X-ray intensity reduces, resulting in a reduction in the number of photons entering the detector 32 per unit time. Due to lower image densities, image reconstruction on the existent tomosynthesis technique will cause noise to be larger and irregularities in density larger.

Unique Image Reconstruction

Therefore, the present embodiment adopts an image reconstruction method capable of providing three-dimensionally spread images (three-dimensionally observable images) of higher noise resistance in which actual sizes and shapes of structural objects are reflected, even if a radiated X-ray intensity is reduced. A process for this image reconstruction will be described later.

Measures Against Changes in Enlargement Factor

Figure 4:
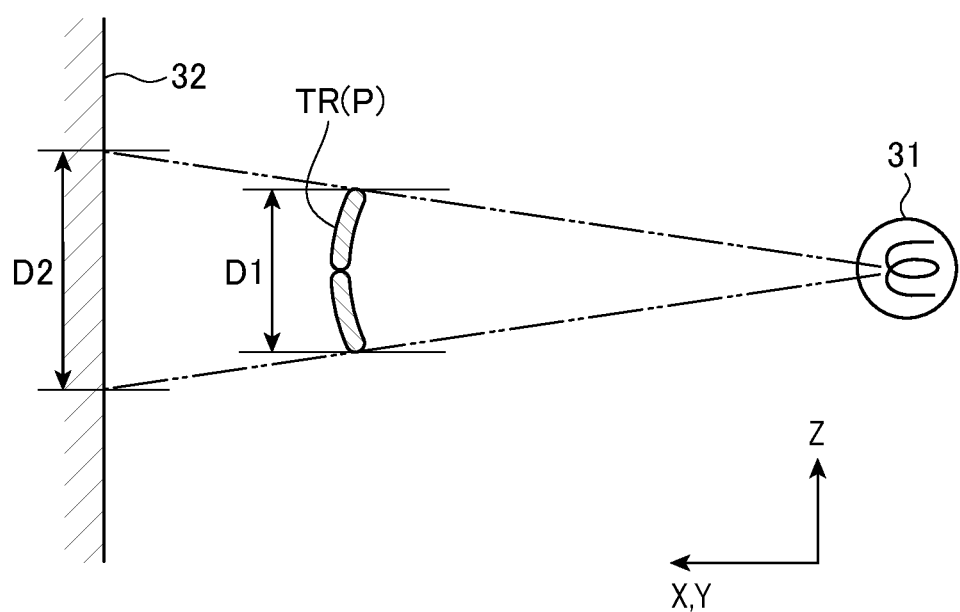
FIG. 4 is a view explaining an enlargement factor.

The distance between the tooth row TR and the X-ray tube 31 changes largely among the respective X-ray radiation angle θ, due to the fact that the tooth row TR is not located at the geometrical center O and the X-ray tube 31 and the detector 32 are rotated along the circular orbit OB during which the orthogonal imaging is performed preferentially. In other words, during scanning the tooth row, an enlargement factor changes among the respective X-ray radiation angles θ. The enlargement factor is defined as a ratio between the actual size of a tooth and the size of a projected image of the tooth whose shade is projected on the detection section of the detector 32. This is pictorially shown in FIG. 4. The foregoing image reconstruction technique includes a process to remove or reduce influence due to this enlargement factor, which will be explained in the whole process for the image reconstruction.

Adjustment of Tube Current

Moreover, in the X-ray extraoral imaging apparatus of the embodiment, the X-ray tube 31 and the detector 32 rotate (move) along the circular orbit OB having the geometrical center O (fixed) in a mutually independent manner. However, the orthogonal imaging is performed preferentially as stated before, the paths of the X-ray beams XB do not always pass through the geometrical center O at the respective rotation angles θ. In other words, instead of understanding that the paths of the X-ray beams XB do not pass through the center O, it should be understood the paths are set independently of the geometrical center O in order to giving priority to the orthogonal imaging. During one scan, there are only three points where the path passes through the geometrical center O, which three points consist of the center of the anterior teeth and two points in two regions respectively covering the right and left molar teeth (refer to FIG. 3).

Figure 5:
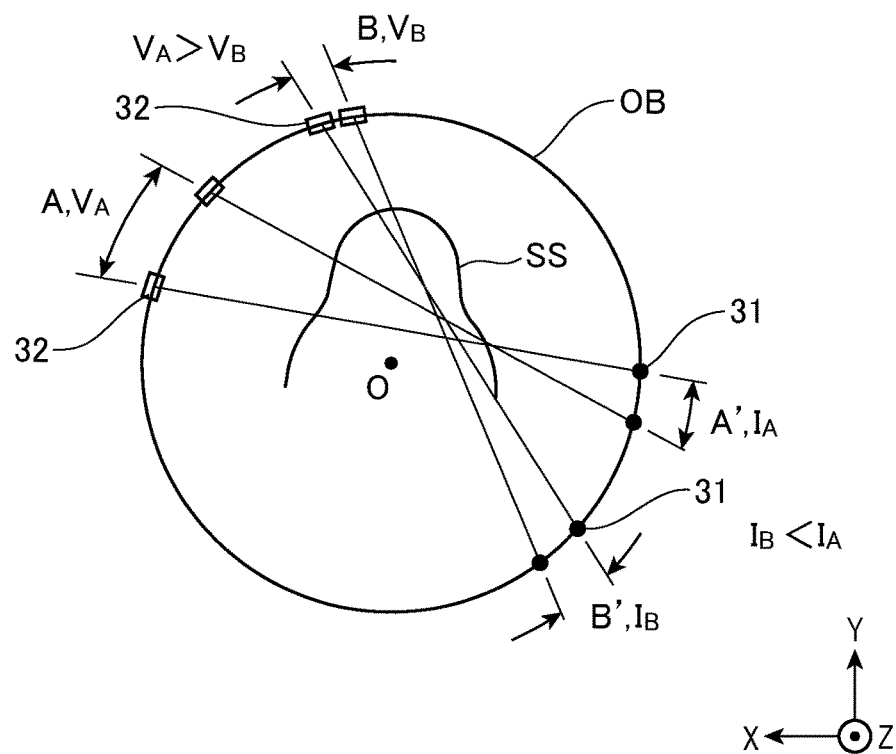
FIG. 5 is a view explaining rotation speeds of an X-ray tube and an detector and control of tube current, which are employed by the orthogonal imaging technique in the embodiment.
Figure 6:
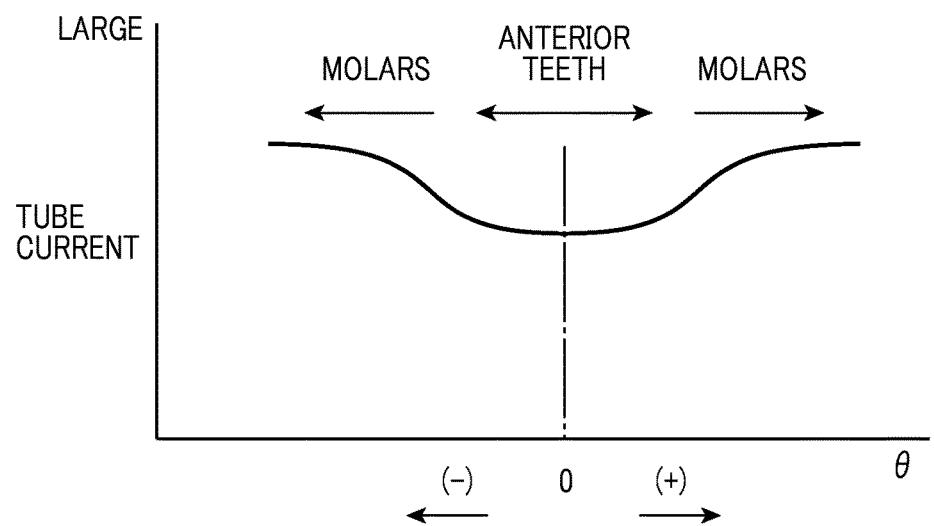
FIG. 6 is a graph exemplifying the control shown in FIG. 5.
Figure 8:
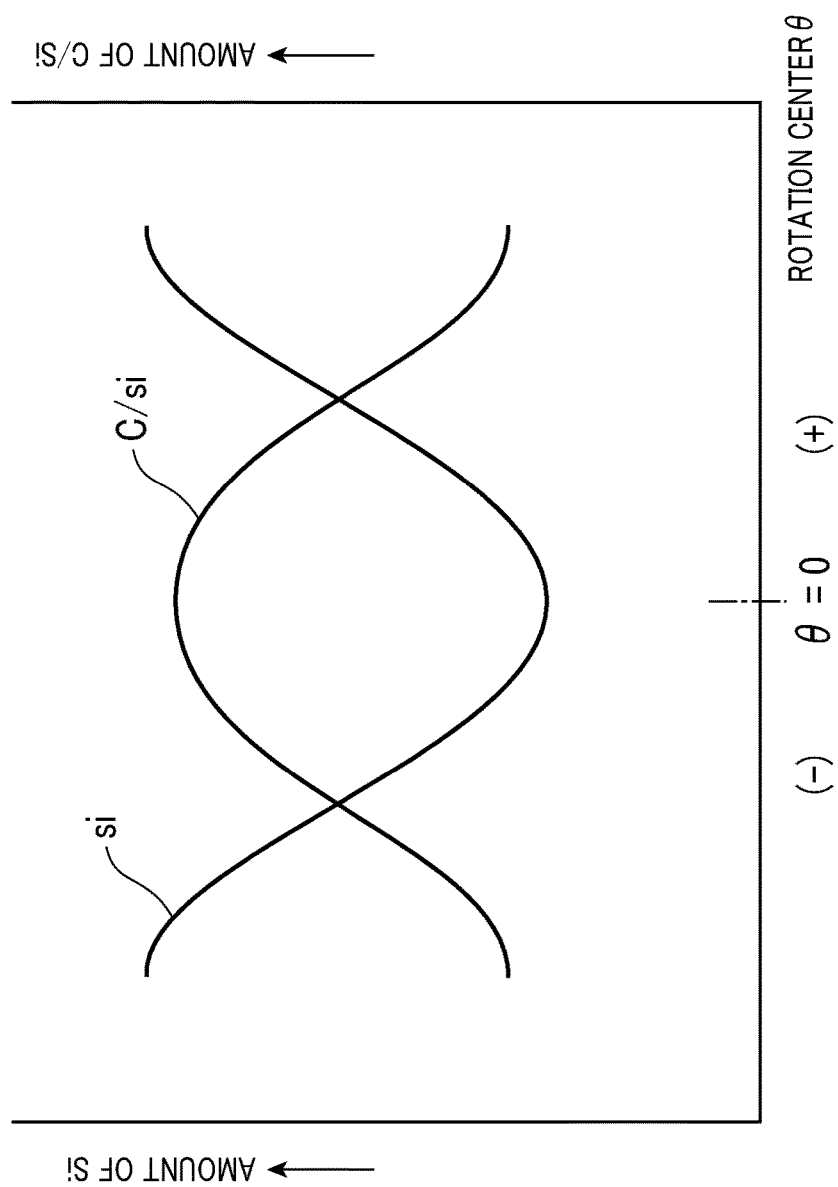
FIG. 8 is a graph exemplifying a relationship between rotation angles and a controlled variable, which is needed to generalize the control shown in FIG. 5.

For achieving such a scan, the angular speed Vθ of rotation of the detector 32 is controlled in accordance with positions on the orbit OB. Hence, it is designed such that, for example, as shown in FIG. 5, the angular speed $V\theta_A$ of rotation given when the detector 32 moves via a certain angle range A (part of the molar area) is larger than the angular speed $V\theta_B$ of rotation given when the detector 32 moves via another angle range B (part of the anterior teeth). During these movements of the detector 32, the X-ray beam XB receives at intervals. This means that the number of photons of X-rays received by the detector 32 depends on positions on the orbit OB. The changes in the number of photons will cause irregularities in pixel intensities of a panoramic image (i.e., density irregularities), thus deteriorating image quality. To remove or reduce the irregularities in the pixel intensities, the tube current I is adjusted depending on rotational positions of the detector 32 on the orbit OB, i.e., rotational positions of the X-ray tube 31 on the orbit OB, which is the other party to the detector. When referring to an example shown in FIG. 5, the tube current $I_A$ of the X-ray tube 31, which is given when the X-ray tube moves during an angle range A' corresponding to the angle range A on the orbit OB, is reduced more than the tube current $I_B$, which is given when the X-ray tube moves during an angle range B' corresponding to the other angle range B. Developing this over the entire rotation angles θ of the X-ray tube 21 provides a characteristic of the tube current I vs. the rotation angles θ, which is generally shown in FIG. 6. In other words, when scanning the right and left molar areas, the tube current I is increased more than that for scanning the anterior teeth. The maximum of the tube current I is set to a value which does not require installment of the foregoing separate room (i.e., the radiation imaging room). Data indicative of a correction characteristics for the tube current I, which is shown in FIG. 8, are previously stored in a later-described look-up table in the ROM. Thus this tube current I is also controlled at the respective X-ray radiation angles.

Incidentally, although, as shown in FIG. 3, the paths of the X-ray beams XB are set such that the cervical spine can be avoided from being scanned as much as possible and desired scan angles θ can be set, it is difficult to set complete paths that positionally avoid the cervical spine. It is inevitable to include some paths that pass through the cervical spine. With consideration this, when the X-ray beams are radiated along some paths passing through the cervical spine, the tube current I may be controlled to increase the X-ray intensity in a controlled manner.

Instead of using the technique of adjusting the tube current as stated above or together with such current control, the tube voltage applied to the X-ray tube 31 may be adjusted. Raising the tube voltage results in an increase in the number of photons, and vice versa. Accordingly, it is possible to provide similar control to adjustment of tube current.

Adjustment of Data Acquisition Time

Moreover, instead of controlling the tube current I or in addition to such current control, a time (duration) for acquiring X-ray transmission data may be controlled. This control concept will now be explained using FIGS. 7-10.

Figure 7:
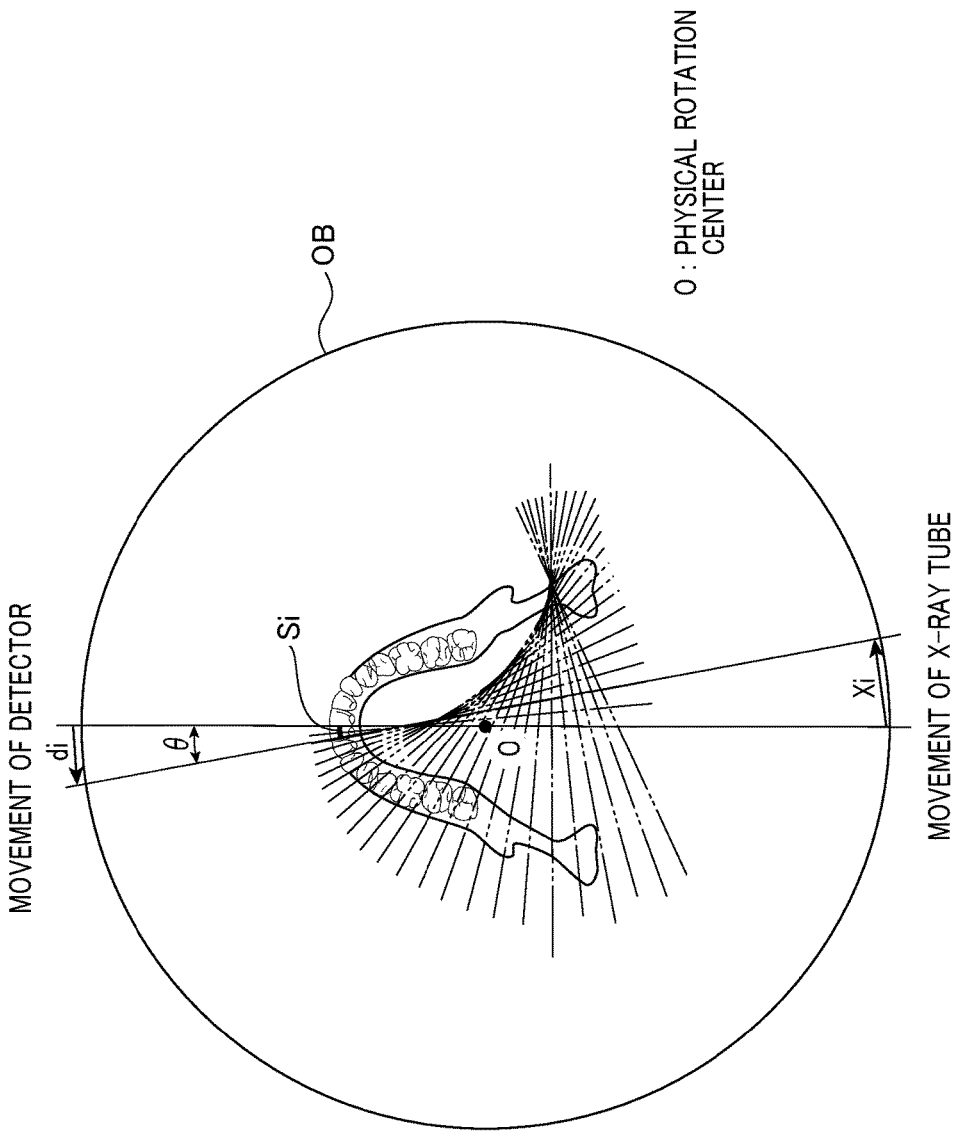
FIG. 7 is a view explaining rotation of the X-ray tube and the detector, which generalizes the control shown in FIG. 5.

In the present embodiment, as shown in FIG. 7, during an elapse of a predetermined period of time Ti which is assumed here, the X-ray tube 31 moves along the orbit OB by a distance xi and the detector 32 moves along the orbit OB by a distance di. Hence, it is desirable to set, as an adjustment technique for the data acquisition time, this predetermined period of time Ti such that the number of photons detected by the detector 32 is always the same.

If there are no obstacle shades such as cervical spine, the X-ray tube 31 and the detector 32 are simply moved along the tooth row TR at speeds which are reversely proportional to their moved distances Si. In this state, movements of the X-ray tube 31 and the detector 32 are controlled to meet a relationship of $\Sigma C/Si=\Sigma Ti$=whole acquisition time (where $C$ is a constant).

This speed control is conceptually shown in FIG. 8.

Figure 9:
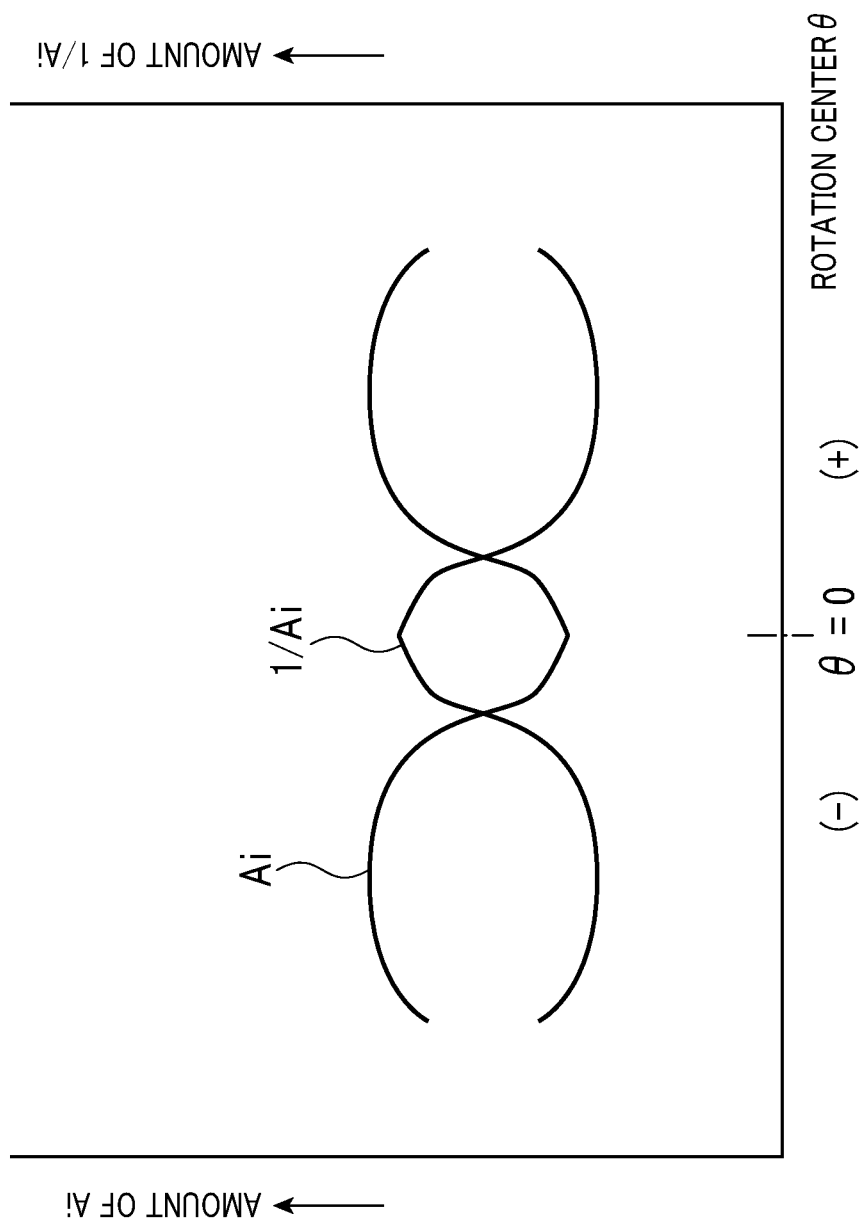
FIG. 9 is another graph exemplifying a relationship between rotation angles and a controlled variable, which is needed to generalize the control shown in FIG. 5.

However, in the actual situation, it is required to consider a factors Ai (constant≤1) indicative of X-ray absorption of cervical spine and jawbones, which factor is exampled in FIG. 9. From this point of view, it is desirable that movements (rotations) of the X-ray tube 31 and the detector 32 are controlled to meet a relationship of $\Sigma C/(Si \cdot Ai)=\Sigma Ti$=whole acquisition time.

Figure 10:
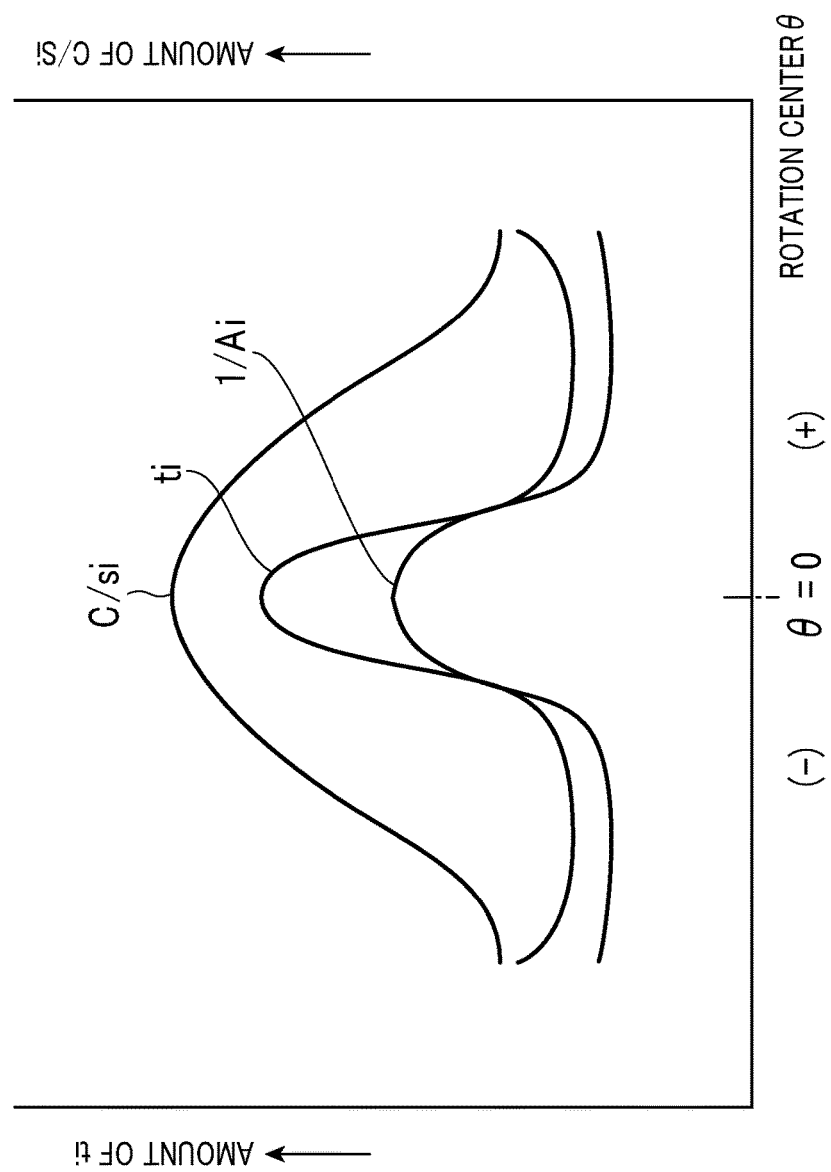
FIG. 10 is still another graph exemplifying a relationship between rotation angles and a controlled variable, which is needed to generalize the control shown in FIG. 5.

This control is exemplified in FIG. 10. This control will enable densities in the lateral direction (a direction along which the X-ray beam XB is scanned) of a panoramic image to become closer to each other. In addition to performing this density adjustment, it is desirable to correct enlargement factors in the longitudinal direction of the panoramic image.

As stated, there have been explained the three techniques for improving the irregularities in the image densities, i.e., controlling the tube current, the tube voltage, and the data acquisition time. These three techniques can be performed with an appropriate combination (e.g. combined three techniques or combined tow techniques) or any one technique can be used solely.

<Independent Control of Collimator>

In the present embodiment, another feature is that the collimators 33 are also controlled in its position and attitude, which is as follows.

Figure 11A:
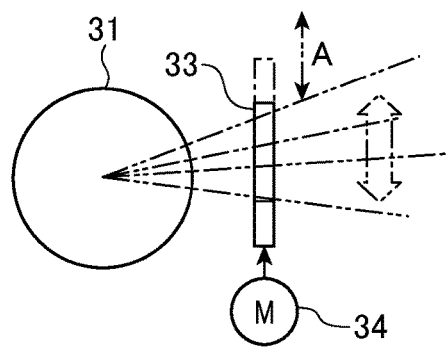
FIG. 11(A) and 11(B) are views explaining control of a collimator performed independently of the X-ray tube.
Figure 11B:
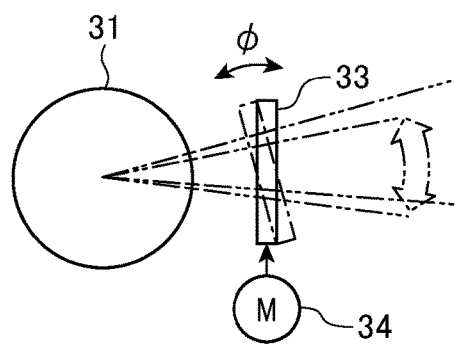

In this embodiment, the position and the attitude of the collimator 33 is also controlled depending on the foregoing lines each connecting the X-ray tube 31 and the detector 32, that is, the X-ray radiation directions. As pictorially shown in FIG. 11(A), the position of the collimator 33 is referred to as a collimator position which is in front of the X-ray tube 31, perpendicular to the direction of the X-ray beam XB, and along the XY plane. Further, as pictorially shown in FIG. 11(B), the attitude of the collimator 33 is referred to as a collimator attitude which is rotated relatively to the X-ray beam XB.

The necessity for controlling the position and attitude of the collimator 33 arises from the fact that the scanning for panoramic imaging in the present embodiment is performed using the circular orbit and due to this, the detector and X-ray tube are not always directly opposed to each other at the radiation angles. Furthermore, this results from the fact that the scanning is based on the orthogonal imaging. If the X-ray tube 31 and the detector 32 are always directly opposed to each other, the position and attitude of the collimator 33 can be fixed, i.e., no control is needed. However, as understood from FIG. 3, the detector 32 is oriented to be oblique to the X-ray tube 31 at most of the rotation angles θ, except for the center of the anterior teeth and the two points respectively belonging to the right and left molar areas. Concretely, the detector 32 moves away from the frontal direction P of the X-ray tube 31, whereby it is necessary to appropriately control the position and/or attitude of the collimator 33 in order to allow the X-ray beams XB to precisely enter the detection section of the detector 32.

An alternative to this collimator control is that only one of the position and attitude of the collimator 33 is controlled depending on the radiation angles θ from the X-ray tube 31, which is a simplified control.

<Others>

Additionally, the scan device 10 according to the embodiment includes rotation sensors 36 and 37 to detect rotational positions of the X-ray tube 31 and the detector 32, and a motion sensor 38 to sense motions of the jaw of a patient P during scanning. The rotation sensors 36 and 37 may be of sensors which calculate the number of pulses of pulse signals issued from the controller to drive the motors.

Figure 12A:
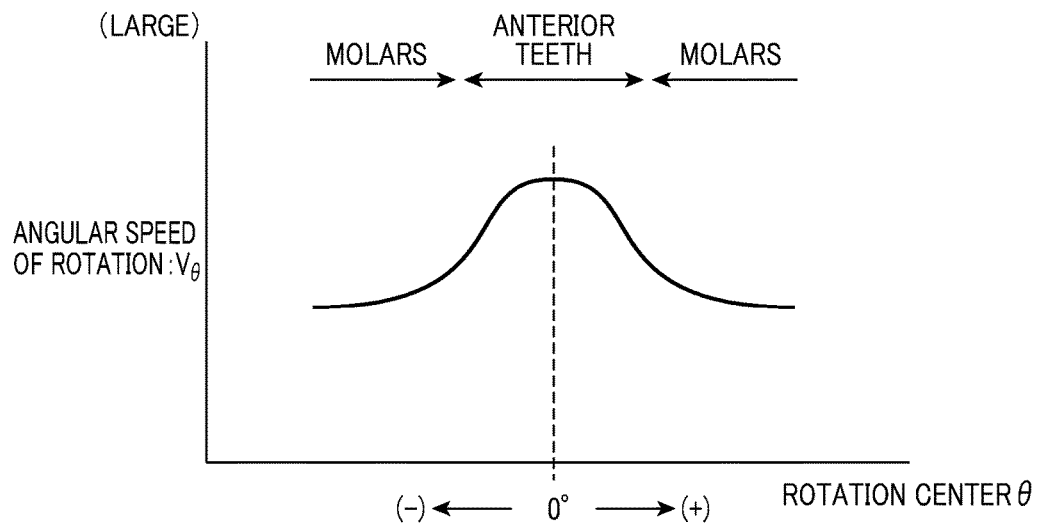
FIG. 12(A) and 12(B) show graphs which exemplify control of both the rotation angles and angular speeds of the X-ray tube and detector.

Further, in the LUT of the ROM 56, a rotation control pattern is previously stored as a reference function, where the rotation control pattern is defined by a horizontal axis to which the rotation angles θ is assigned and a vertical axis to which the angular speeds $V_θ$ of the rotation is assigned, as shown in FIGS. 12(A) and (B). This rotation control pattern defines the reference function regulating the positional relationships among the X-ray tube 31, the detector 32 and the tooth row TR of the jaw of a patient P at every rotation angle θ, which are necessary for the "orthogonal imaging" and for reducing irregularities in the densities in the lateral directions of a panoramic image. Hence, this reference function is preset based on not only the speed control factor necessary for the orthogonal imaging but also any one of the adjustment factor for the tube current and the adjustment factor for the data acquisition time, which are the foregoing measures for reducing irregularities in the image densities.

FIG. 12(A) defines the rotation of the X-ray tube 31, where the rotational angular speeds $V_θ$ are regulated at every rotation angle θ. According to this graph, the rotational angular speed $V_θ$ becomes high at the rotation angle θ=0 degrees, while the rotational angular speed $V_θ$ is reduced as the rotation angle θ increases from 0 degrees in both positive and negative directions. The rotation angle θ=0 degrees is a reference position as shown in FIG. 3. Concretely, in the present embodiment, the 3D referential tomographic plane SS (viewed along the Z-axis direction in FIG. 3) is set along the tooth row TR located in the circular orbit OB. An X-ray beam XB passing through the center of the anterior teeth of the tooth row TR along the 3D referential tomographic plane SS is set to pass through the geometrical center O of the circular orbit OB. This line passing through the center of the anterior teeth and the geometric center O is given the rotation angle θ=0 degrees.

Figure 12B:
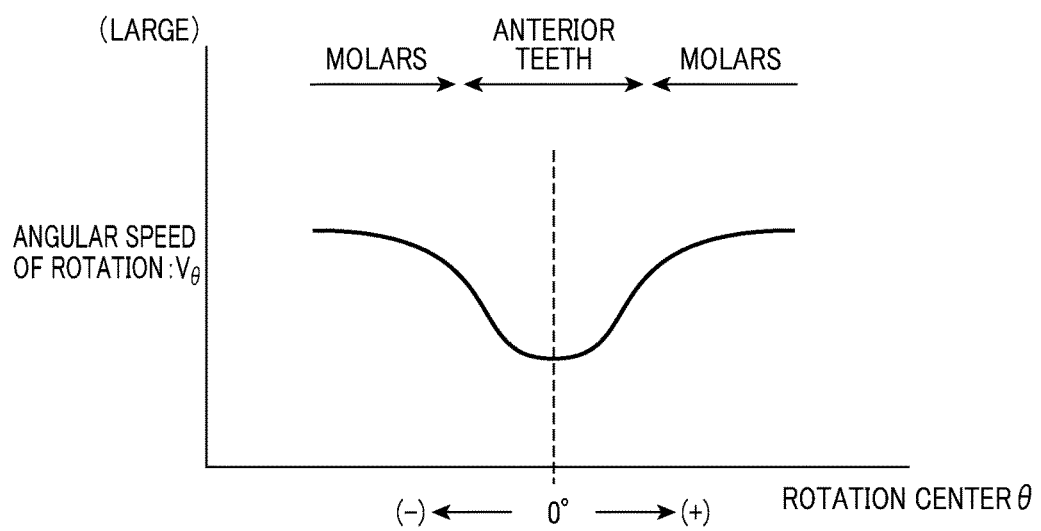

In contrast, FIG. 12(B) defines the rotation of the detector 32, where the rotational angular speeds $V_θ$ are regulated at every rotation angle θ. This graph shows an upside-down or approximately upside-down curve to that shown in FIG. 12(A) in terms of their angular speeds.

<Scan>

A pre-scan for checking an angle of the jaw and a main scan for acquiring data, which are performed by the X-ray extraoral imaging apparatus 1 according to the embodiment, will now be described.

Pre-scan

In this X-ray extraoral imaging apparatus 1, an amount of X-ray exposure to a patient per scan is reduced, so that a pre-scan can be performed before the main scan to acquire frame data for imaging for the purpose of an actual diagnosis. With this pre-scan performed, the amount of X-ray exposure is still kept low. The pre-scan is performed to intend to acquire data at a high speed in a state where each pixels size is made larger and the tube current is lowered.

Figure 13:
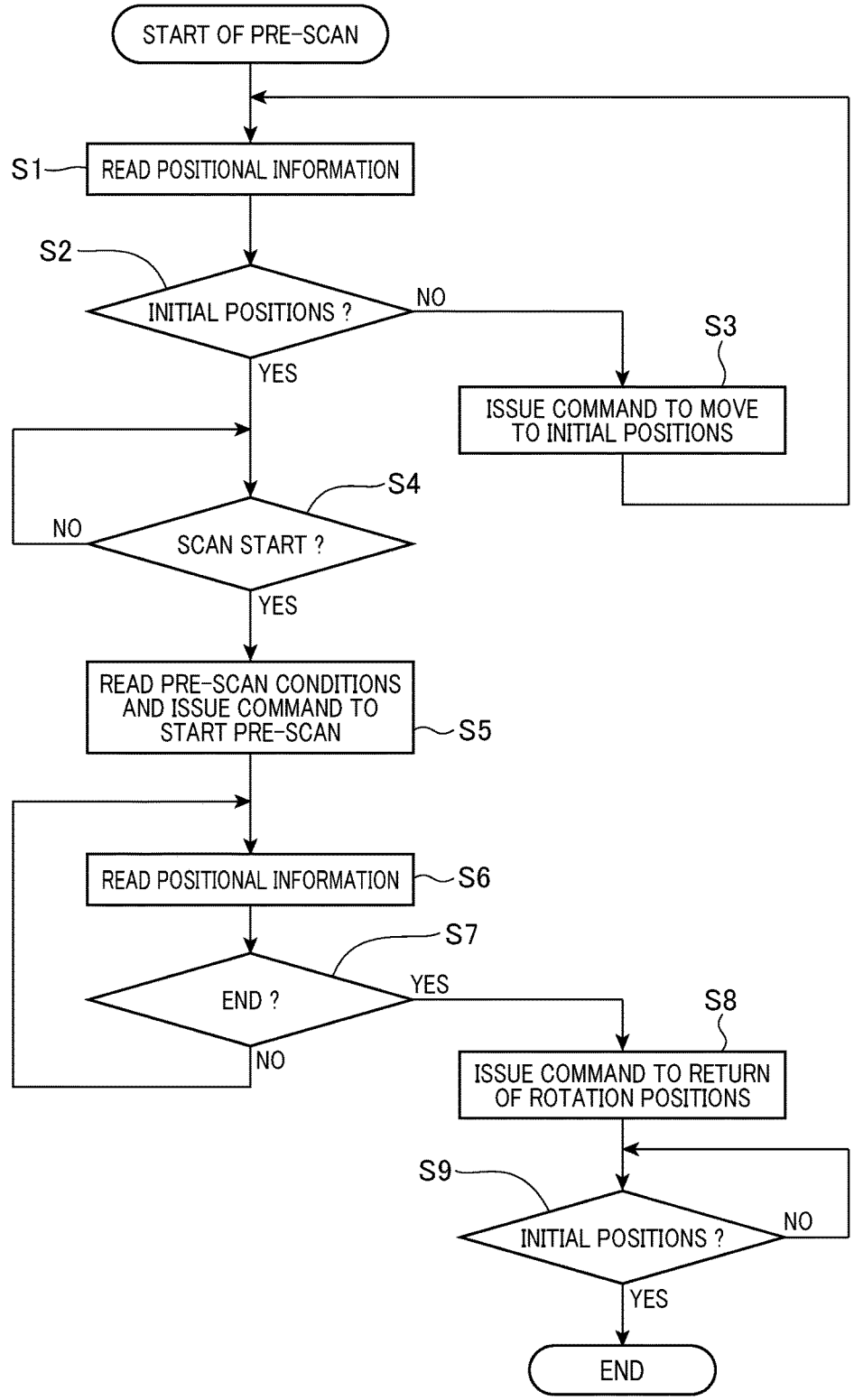
FIG. 13 is a flowchart outlining a pre-scan.

Steps for this pre-scan are shown in FIG. 13.

The scan device 10 is located around the face, i.e., the jaw of a patient, thereby locating the ring member 11 closely to and around the jaw. Then the controller 55 starts it control.

When the pre-scan starts, the controller first reads, at step S1, positional information from the rotation sensors 36, 37 to calculate the positions of the X-ray tube 31 and the detector 32 on the orbit OB. Then the controller 55 determines, at step S2, whether or not the calculated positions are preset initial positions, and if no initial positions, proceeds to step S3. At step S3, the motors 42, 52 are driven to return the X-ray tube 31 and the detector 32 to their preset initial positions on the orbit OB. In this case, the position and attitude of the collimator 33 to the X-ray tube 31 are controlled to their predetermined position and attitude.

In contrast, the determination at step S2 shows that the X-ray tube 31 and the detector 32 are already at their initial positions on the orbit, the controller 55 proceeds step S4 to monitor an operational signal from an operator via the operation devise 61 and determines if or not the pre-scan should be started, thereby waiting for the start of the pre-scan.

When the determination at step S4 is YES, i.e., the operator commands the start of the pre-scan, the controller 55 proceeds to step S5, where information of pre-scan conditions is read from the LUT of the ROM 56 and the performance of the pre-scan is started. The pre-scan conditions include radiation conditions (tube voltage and tube current), a scan speed (i.e., rotational speeds of the X-ray tube 31 and the detector 32), and the number of pixels to be combined in image processing. For instance, compared with the main scan later described, the pre-scan conditions are such that the tube current is ½, the scan speed is 2 times, and the number of combined pixels is 4.

In the pre-scan, from its intension, a two-dimensional panoramic image or a three-dimensional tomographic image (a three-dimensional panoramic image) is allowed even if the image is coarse in pixels, provided that such an image is interpreted by a doctor. Hence, in the present embodiment, the pre-scan conditions include conditions commanding a fast scan speed and a lowered tube current, and other conditions which are the same as those for the main scan later described. The other conditions include, as described later, the correction of the tube current, the attitude and position control of the collimator, setting the scan range (the range of the rotation angle θ) to 210 degrees for example, and the three-dimensional autofocusing image reconstruction with considering actual positions of components.

However, it is not always necessary that the pre-scan conditions agree with the main scan conditions. The pre-scan conditions may be according to that for the conventional various processes for panoramic images.

At step S6, the controller 55 again reads from information indicating rotational positions from the rotation sensors 36 and 37 to calculate the current rotational positions of the X-ray tube 31 and the detector 32 on the orbit OB. Then at step S7, the controller 55 uses the rotational positions to determine if or not the pre-scan has ended. Practically, it is determined whether or not the X-ray tube 31 and the detector 32 have moved along the orbit OB, during which X-ray scanning has been performed in the preset rotation angle range (e.g. 210 degrees), and determined whether or not the X-ray tube and the detector have arrived at the preset terminal rotational positions.

When the determination at step S7 is YES, that is, the terminal rotational positions are detected, the controller 55 returns the X-ray tube 31 and the detector 32 to their initial positions on the orbit OB through processing at steps S8 and S9, similarly to the foregoing, and the pre-scan control is ended.

In contrast, the determination NO at step S7, that is, the X-ray tube 31 and the detector 32 have not arrived at their terminal preset positions, makes the processing return to step S6.

The image processor 54 applies the tomosynthesis technique to the frame data acquired by the pre-scan, where this tomosynthesis technique is also used the main scan later described. Although will be described later, this application produces a three-dimensional (pseudo three-dimensional) panoramic image in which structural components are automatically optimally focused along the oblique directions always viewing from the focal point of the X-ray tube so that the spatial real positions of the structural are reflected in the image. This reconstructed three-dimensional panoramic image is subjected to combining mutually adjacent four pixels to one pixel at each position of the reconstructed image, whereby a new panoramic image is produced. The size of this new panoramic image is reduced, thus providing a coarse image quality, but being sufficient for checking structural components such as tooth row TR. Since the scan speed is 2 times and the tube current is ½, so that the total amount of X-rays reduces down to ¼, compared to the case with no such speed and current conditions. This reduces the amount of X-ray exposure.

An operator observes the produced three-dimensional panoramic image to check if the tooth row TR is imaged precisely and the angle of the jaw (neck) is proper. If necessary, positioning of the jaw is changed. Further, a cervical spine CS is also shaded in this panoramic image. Thus the angle of the jaw (neck) is also checked and changed if necessary so that the X-ray beams from the X-ray tube 31 pass between bones of the cervical spine CS as much as possible when the X-ray tube 31 moves in the rear of the neck. This angle adjustment contributes to strengthen improvement of image quality.

As an alternative, the angle of a chinrest can be controlled to change the position of the chin depending on observed results of the produced three-dimensional image and analysis of the jaw position which should be located at a desired three-dimensional position. Incidentally, if the panoramic image is produced by the conventional reconstruction technique, an operator still uses that image to check and change the jaw position.

Main Scan

Figure 14:
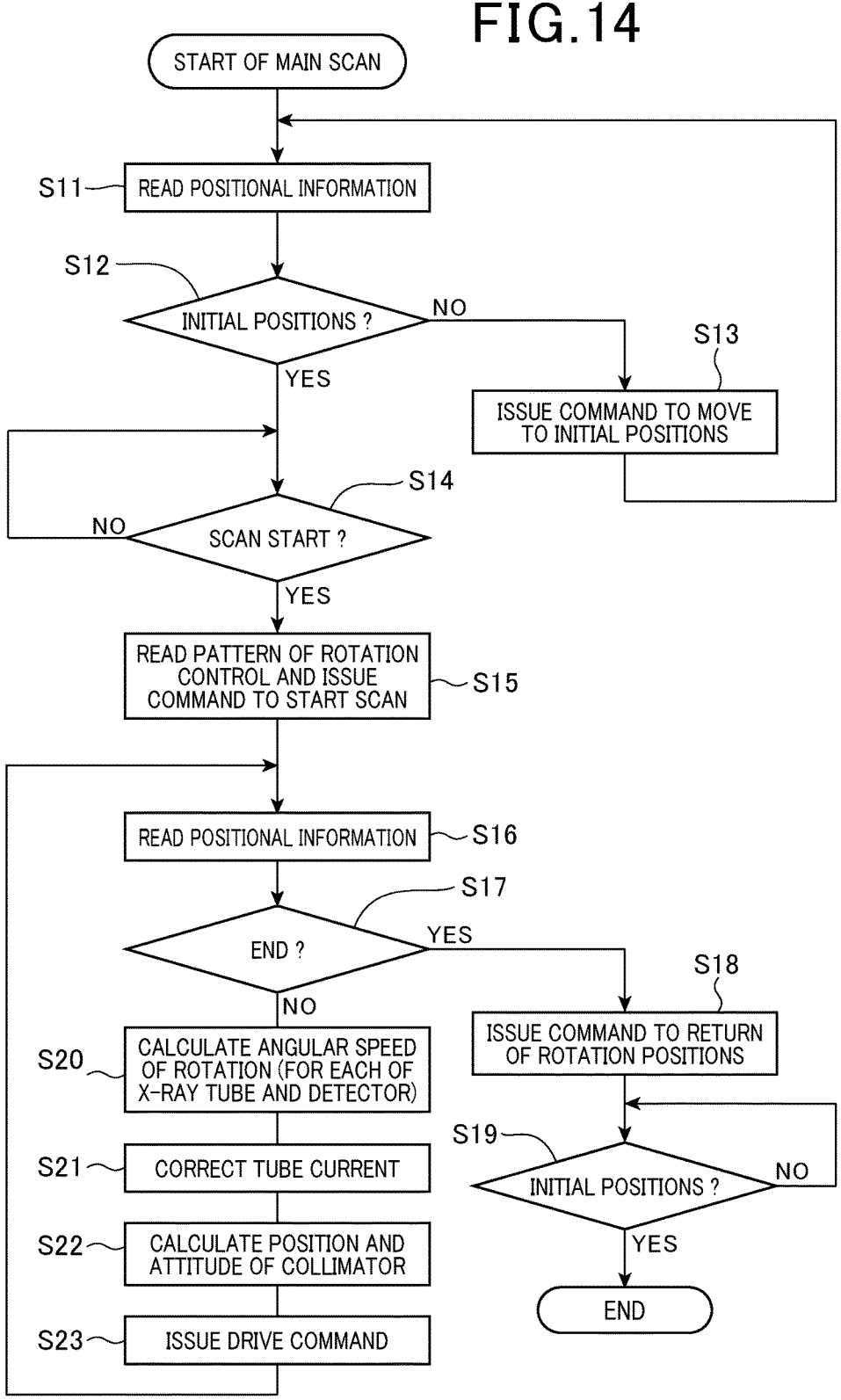
FIG. 14 is a flowchart outlining a main-scan.

With reference to FIG. 14, the control of the main scan performed under the control of the controller 55 will now be described.

The controller 55 reads a program for scan control from the ROM 56 into its work area, and performs steps of this program in sequence.

When this program starts, the controller 55 first, at step S11, reads positional information from the rotation sensors 36 and 37 to calculate the positions of the X-ray tube 31 and the detector 32 on the orbit OB. Then the controller 55 determines, at step S12, whether or not the calculated positions are preset initial positions, and if no initial positions, proceeds to step S13. At step S13, the motors 42, 52 are driven to return the X-ray tube 31 and the detector 32 to their preset initial positions on the orbit OB.

In contrast, the determination at step S12 shows that the X-ray tube 31 and the detector 32 are already at their initial positions on the orbit, the controller 55 proceeds step S14 to monitor an operational signal from an operator via the operation devise 61 and determines if or not the main scan should be started, thereby waiting for the start of the main scan.

When the determination at step S14 is YES, i.e., the operator commands the start of the main scan, the controller 55 proceeds to step S15, where information indicating the reference functions (rotation patterns) for the X-ray tube 31 and the detector 32 are read from the LUT of the ROM 56 and the performance of the main scan is started using the reference functions. The reference functions provide, as shown in FIGS. 12(A) and (B), the horizontal axis showing the rotational positions θ and the vertical axis showing the angular speed of rotation, $V_θ$.

At step S16, the controller 55 again reads from information indicating rotational positions from the rotation sensors 36 and 37 to calculate the current rotational positions of the X-ray tube 31 and the detector 32 on the orbit OB. Then at step S17, the controller 55 uses the rotational positions to determine if or not the main scan has ended. Practically, it is determined whether or not the X-ray tube 31 and the detector 32 have moved along the orbit OB, during which X-ray scanning has been performed in the preset rotation angle range (e.g. 210 degrees), and determined whether or not the X-ray tube and the detector have arrived at the preset terminal rotational positions.

When the determination at step S17 is YES, that is, the terminal rotational positions are detected, the controller 55 returns the X-ray tube 31 and the detector 32 to their initial positions on the orbit OB through processing at steps S18 and S19, similarly to the foregoing, and the main scan control is ended.

In contrast, when the determination at step S17 is NO, i.e., the X-ray tube 31 and the detector 32 have not arrived at their preset terminal positions, the controller 55 proceeds to step S20. By the process at step S20, the angular speeds $V_θ$ of rotation of the X-ray tube 31 and the detector 32 are calculated according to their current rotational positions θ detected at steps S16. Concretely the controller 55 refers to the LUT of the ROM 56 to apply the current rotational positions θ to the functions shown in FIGS. 12(A) and (B), whereby rotational angular speeds $V_θ$ now being commanded can be calculated.

The controller 55 then, at step S21, calculates an amount of current I to the X-ray tube 21 according to the current rotational position 8. This calculation is intended to correct differences in the number of photons of X-rays detected by the detector 22, as described. An alternative way is to skip this adjustment process of the tube current I if irregularities in image densities can be suppressed sufficiently by controlling the data acquisition time stated already.

The controller further proceeds to step S22, where the rotation angles θ of the X-ray tube 31 and the detector 32 obtained at step S20 are used to calculate a command(s) for controlling the position/attitude of the collimator 33. This command is calculated as a drive signal for the drive member 34 which drives the collimator 33.

Since the rotational speeds V of the X-ray tube 31 and the detector 32, the current I of the X-ray tube 31, and the position/attitude of the collimator 33 can be obtained, the controller 55 provides, as instructions, such values to the motors 42, 52 and 34 and the high-voltage generator 12. Responsively, the X-ray tube 31 receives a pulse drive signal from the high-voltage generator 12, which drive signal depends on a predetermined tube voltage V and the calculated tube current I, whereby the X-ray tube generates X-rays whose intensities and number of photons are instructed by the drive signal. Meanwhile, driving the motors 42, 52, which are now pulse-driven for instance, enable the X-ray tube 31 and the detector 32 to move (rotate) along the orbit OB at mutually independent rotational speeds. Moreover, at each of the rotational positions of the X-ray tube 31 and the detector 32, the X-rays radiated from the X-ray tube 31 are collimated so that the collimated X-ray beams are precisely directed toward the window of the detection section of the detector 32. As a result, the X-ray beams XB are always able to accurately enter the window of the detection section of the detector 32.

Then the controller 55 returns to step S16, and the foregoing steps S16-S23 are repeated until the scan end and the return to the initial positions.

Figure 15A:
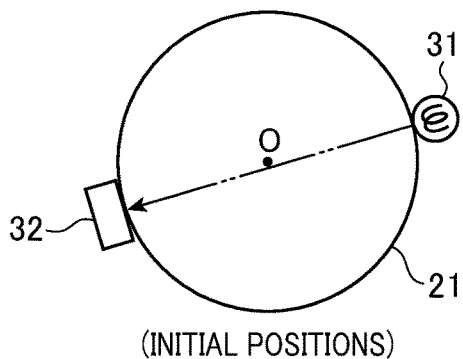
FIG. 15(A)-15(F) are views explaining rotation of the X-ray tube and the detector during the scans.
Figure 15B:
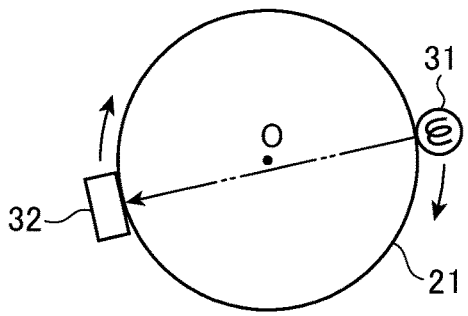
Figure 15C:
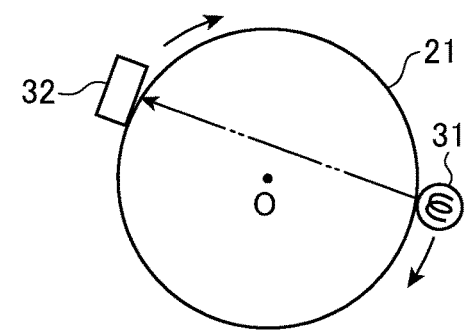
Figure 15D:
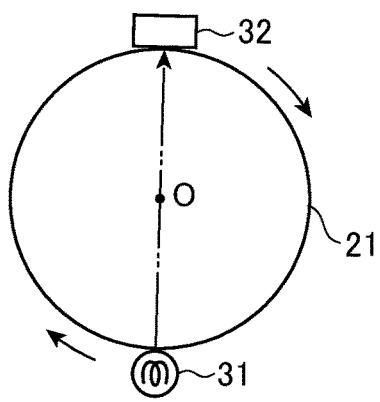
Figure 15E:
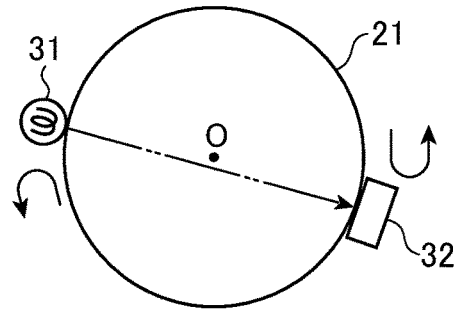
Figure 15F:
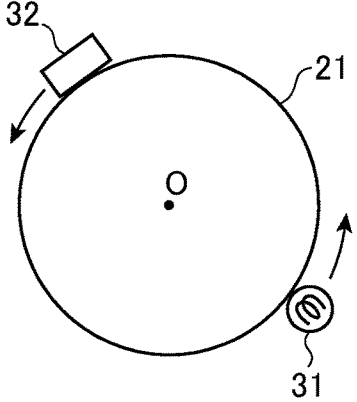

Accordingly, the X-ray tube 31 and the detector 32 (and the collimator 33) which are located at their initial positions as shown in FIG. 15(A) start to move along the circular orbit OB in response to start of their rotational operations (refer to FIG. 15(B)). During this movement, the X-rays are radiated from the X-ray tube 31 at intervals. The paths for the X-ray beams XB are dedicated to, for example, the predetermined orthogonal imaging, where the paths are set to be orthogonal as much as possible. The movement of the X-ray tube 31 and the detector 32 soon makes them to pass the front of the jaw of the patient P (refer to FIGS. 15(C) and (D)). During the movement, the X-ray scan is performed at intervals. When the X-ray tube 31 and the detector 32 arrives at their rotational end points (i.e., the end points of the angle range of 210 degrees) (refer to FIG. 15(F)), the scanning is ended and returns to their initial positions (refer to FIG. 15(F)).

The controller 55 always monitors a single from the motion sensor 38. On detecting a motion of the patient P, the controller responds to a command from the operation device 61 or a further not-shown emergency switch to stop the scanning and send out an alarm. Hence, when the patient P moves due to becoming frightened of the scan actions or unintentionally moves so that it is difficult to secure higher image quality, a scan can be performed again.

<3D Reconstruction>

Figure 29:
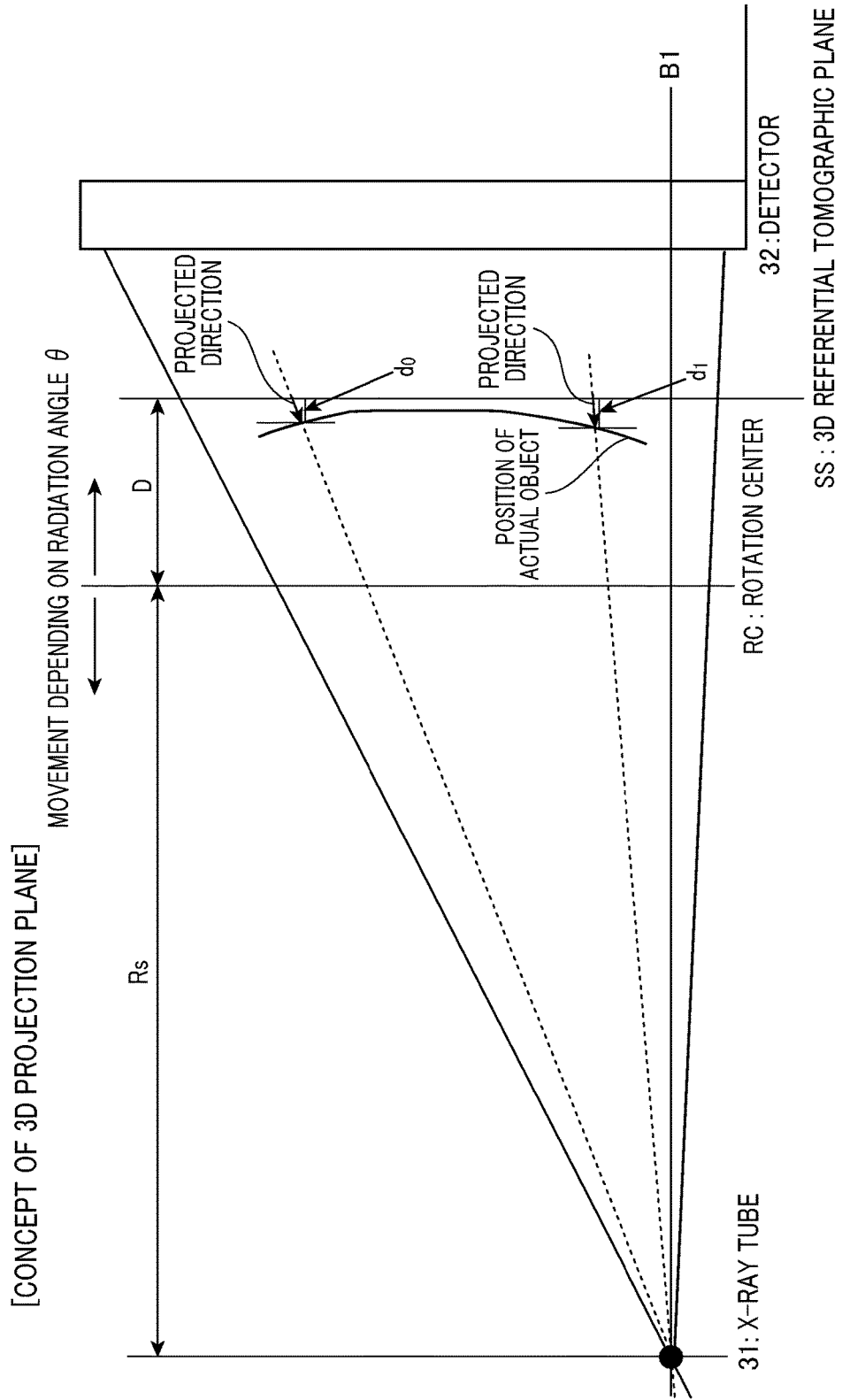
FIG. 29 is a view outlining three-dimensional projection along a direction viewing the X-ray tube position, with consideration of correction of the longitudinal enlargement factor, in the present embodiment.

Meanwhile, as will be detailed later, 3D reconstruction is performed to accurately understand the actual positions of tooth rows in the imaging space IS, when the jaw of a patient is imaged. As pictorially outlined in FIG. 29, this reconstruction is performed to based on data acquired along oblique X-ray radiation directions viewing from the X-ray tube 31 to the 3D referential tomographic plane SS, whereby an object (existent structural components) such as tooth rows can be identified positionally accurately. Hereinafter imaging including this identifying process will now be described.

(Calibration of Parameters Defining the Imaging Space)

Prior to explaining imaging, calibration for the imaging space which is performed using a phantom will now be explained. That is, the calibration is for estimating values and changes in the values of geometric parameters showing the three-dimensional structure of an imaging system to the referential tomographic plane in the imaging space. The results of this calibration are reflected in reconstructing images and, if need arises, used for structural analysis and design of the imaging space.

Processing for this calibration is performed by the controller 55 and the image processor 54 in a cooperative manner. Of course, a processor dedicated only to the calibration may be used. In the present embodiment, this calibration is characterized by use of a phantom that models a tooth row of patients P.

(Phantom)

Figure 16:
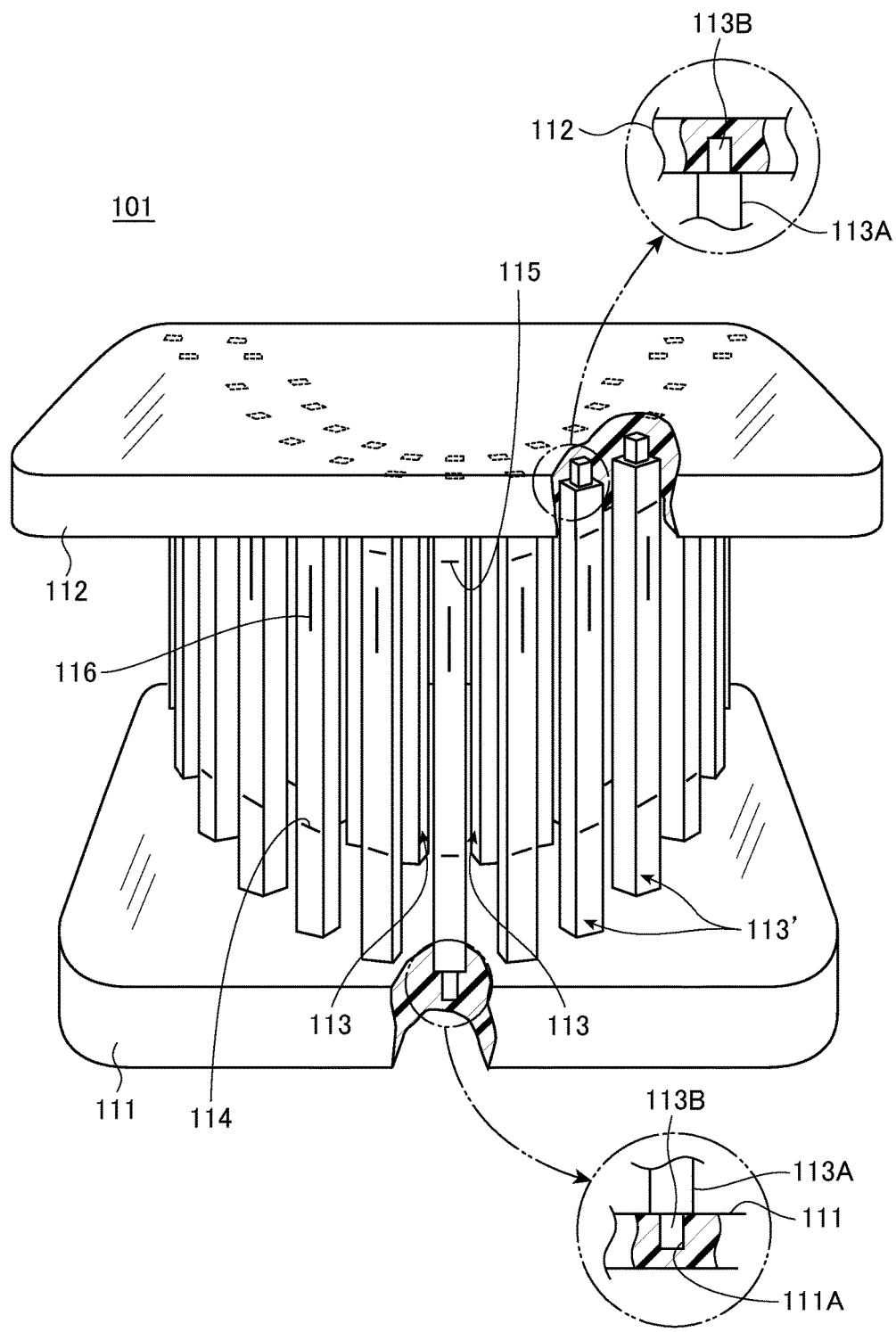
FIG. 16 is a perspective view, with partly broken, showing an example of a phantom.

FIG. 16 shows the appearance of a partly sectioned phantom 101 (phantom device). This phantom 101 is a single universal phantom with which parameters necessary for the calibration can be measured. However, the phantom for the present invention will not always be limited to such a universal type phantom, but its configuration may be modified in various ways as long as the parameters for 3D image reconstruction can be calibrated as will be described. Some of such modifications will also be described later.

The universal phantom 101 includes a clear resin-made plate-shaped base 111, a clear resin-made top plate 112, and a plurality of pillars 113 held between the base 111 and the top plate 112. As will be described later, these pillars 113 (113') have metal markers of which X-ray transmittance differs from that of resin materials. By way of example, one type of resin is acrylic, but other types of resin may be used provided that the X-ray transmittance is different from that of the markers. The reason for using the clear resin is that it is easier to optically see the markers.

Each of the pillars 113 (113') has upper and lower ends respectively inserted into the base 111 and the top plate 112 and supported there. In the following, this support will be detailed.

Figure 17:
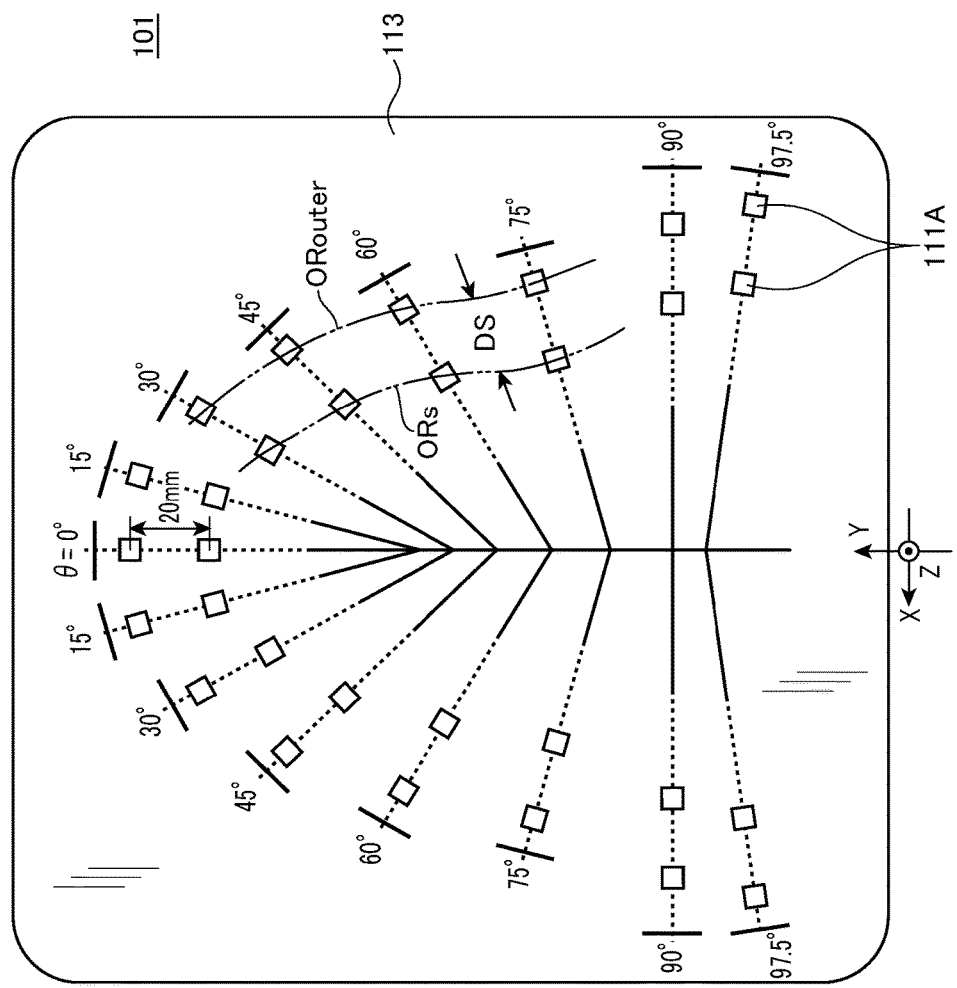
FIG. 17 is a plan view showing the base of the phantom, with which a relationship between planting positions of pillars with markers and positions of tomographic planes used for calibration.

As shown in FIGS. 16 and 17, the base 111 is shaped into a square plate and made of a clear resin material. On the upper surface of the base 111, a reference-plane trajectory (or orbit) OR and an outer-plane trajectory $OR_{outer}$ are set, where the reference-plane trajectory $OR_s$ is formed by projecting the 3D referential tomographic plane SS onto the XY plane and the outer-plane trajectory $OR_{outer}$ is formed by drawing, for example, parallelly with the reference-plane trajectory $OR_s$, a reference-plane trajectory at a position moved outwards apart from thereof by a predetermined distance DS, for example, 20 mm. These trajectories $OR_s$ and $O_{Router}$ may be depicted on the base 111 as actual lines so that an operator can easily recognize them, or those $OR_s$ and $OR_{outer}$ may be virtual.

On the upper surface of the base 111, there are formed square planting holes 111A at plural intersections at each of which both trajectories $OR_s$ and $OR_{outer}$ intersect with X-ray radiation angles θ produced when the X-ray tube 31 and the detector 32 are rotated to focus on the referential tomographic plane SS. The distance DS between both paths $OR_s$ and $OR_{outer}$ is not necessarily set to 20 mm, but may be another value provided that the parameters later described can be calculated accurately within limited size relations of the phantom.

Figure 18:
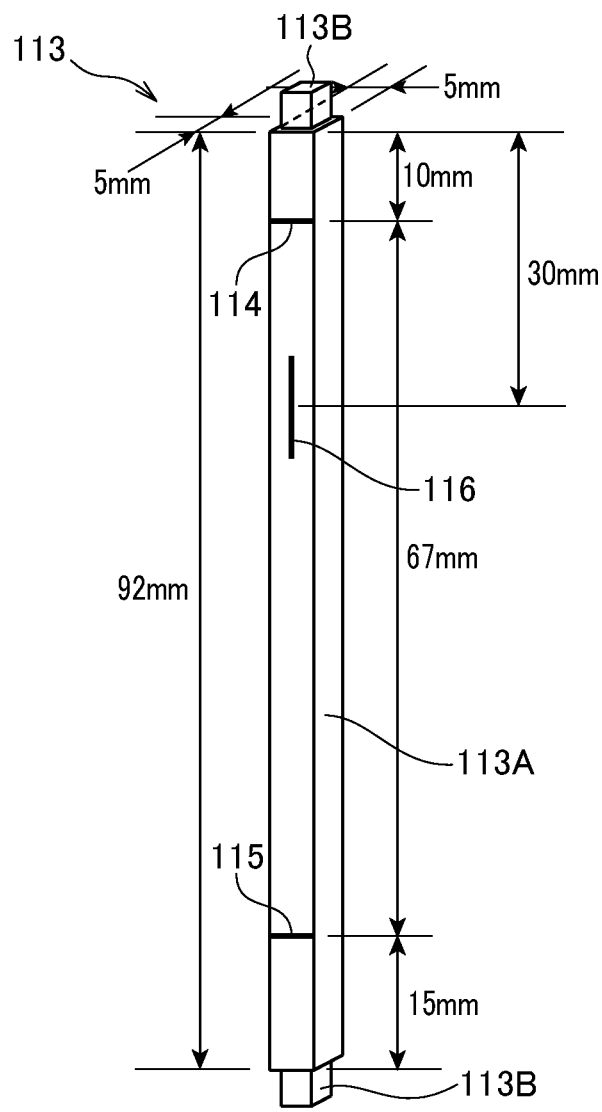
FIG. 18 is a perspective view explaining an example of the pillar being planted at the positions of the referential tomographic plane.
Figure 19:
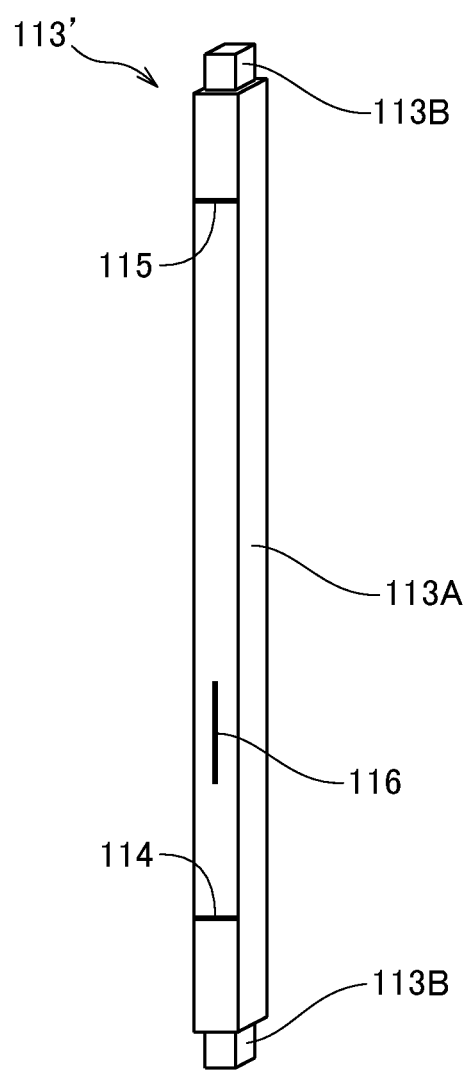
FIG. 19 is a perspective view explaining an example of the pillar being planted at the positions of an outer tomographic plane.
Figure 20A:
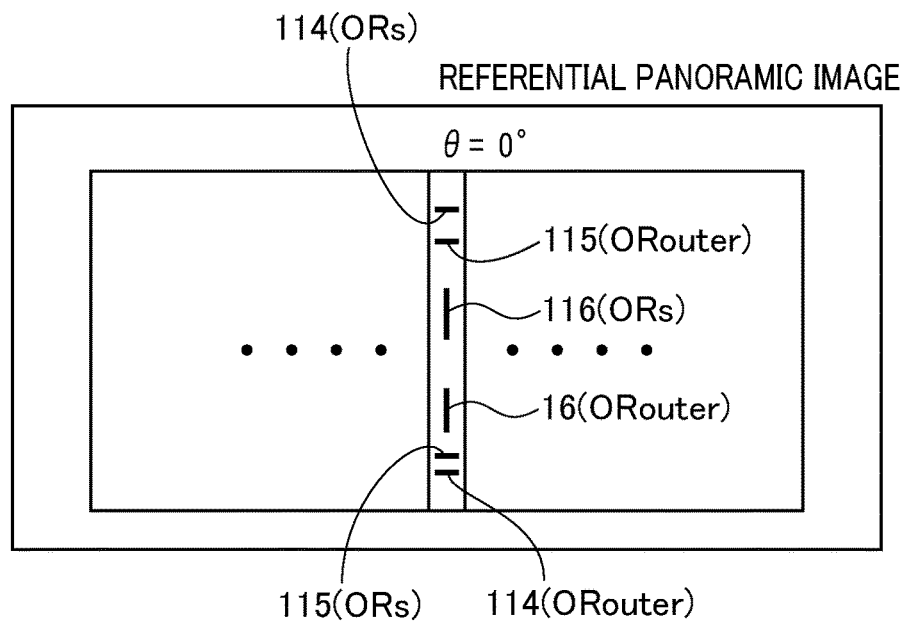
FIG. 20(A) and 20(B) are illustrations explaining positional relationships among the positions of markers imaged in the referential-plane panoramic image, the detector, and the markers.
Figure 20B:
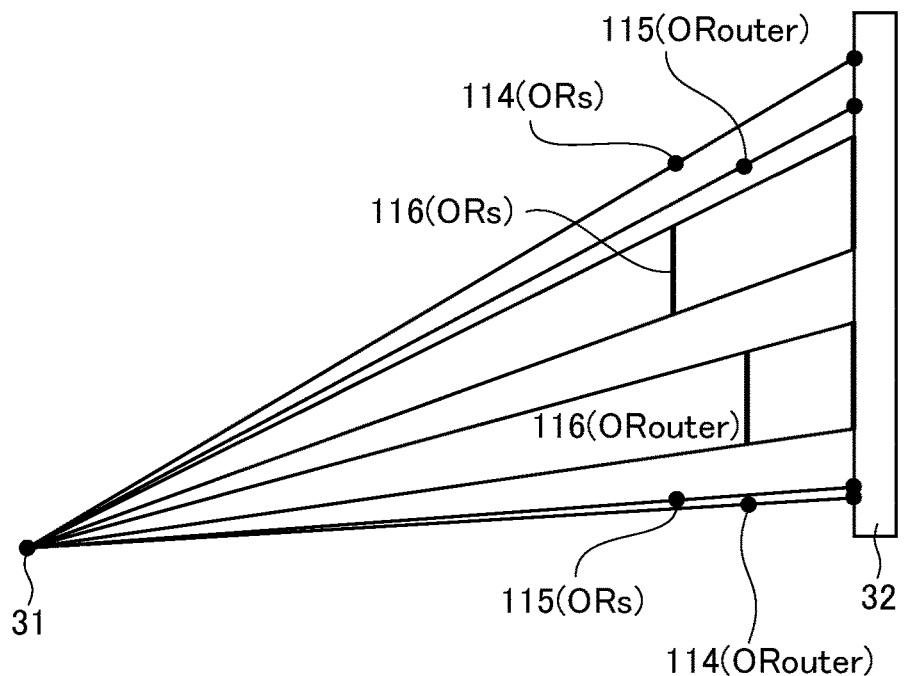

As shown in FIGS. 18 and 19, each of the plural pillars 113 is a prismatic body which is made of resin such as acrylic. Each pillar 113 includes a prismatic pillar body 113A of a specific length and square prismatic protrusions 113B which are integrally protruded from the upper and lower ends of the prismatic pillar body. Each pillar body 113A has a section of a size of 5 mm×5 mm, for example, which is perpendicular to the longitudinal direction of the pillar body, and has a length of 92 mm. Each protrusion 113B has a section size smaller than that of the pillar body 113A, and for example, has a height of approximately 5 mm.

Each pillar body 113A has one surface on which first, second and third markers 114, 115 and 116 are arranged for calibration. These markers 114, 115 and 116 all are produced as small-diameter rods made of aluminum or brass, and have a diameter of 0.6 mm for example. Of these markers, the first and second markers 114 and 115 are laterally arranged at positions apart from the upper and lower ends of the pillar body 113A, respectively, by specific distances of, for example, 10 mm and 15 mm. On the surface of the pillar body 11A, there are provided semicircle-section notches of which diameters are for example 0.6 mm. The first and second markers 114 and 115, which are the small-diameter rods, are secured in the notches.

Moreover, as shown in FIG. 18, the third marker 116 is longitudinally arranged and centered at a position apart from the upper end of the pillar body 113A by a distance of 30 mm, for example. This third marker 116 has a specific length, for example, 20 mm. This third marker 116 is also planted in the same way as the first and second markers 114, 115.

The foregoing pillar 113 and the foregoing marker positions are simply examples, and design can be made with other appropriate sizes.

As described above, as shown in FIG. 16, the pillars 113 are arranged along the reference-plane trajectory $OR_s$.

Figure 43:
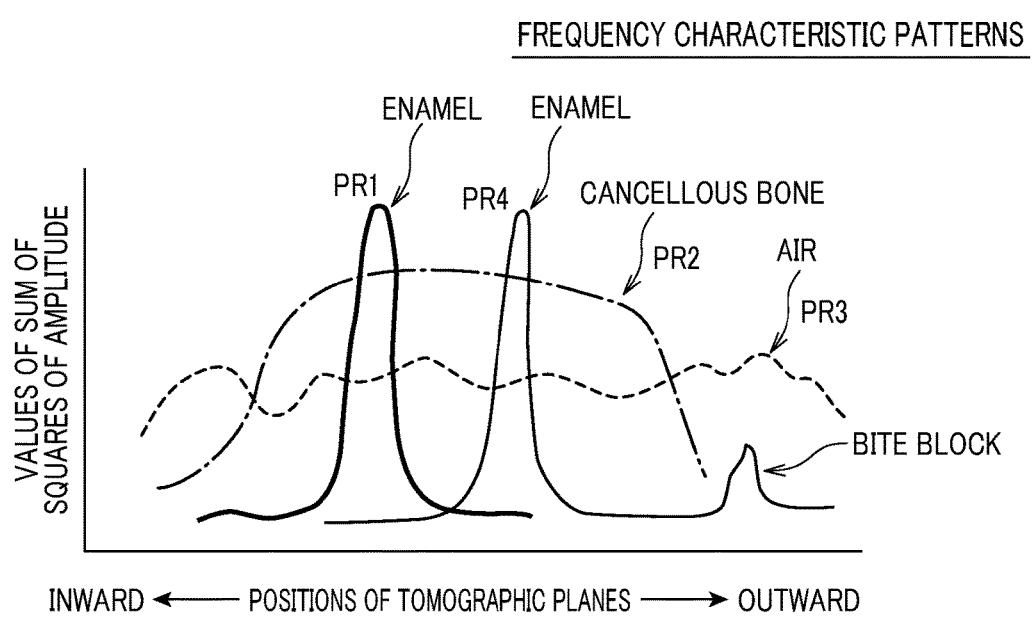
FIG. 43 is a graph exemplifying frequency characteristic patterns changing depending on tomographic plane positions.
Figure 44:
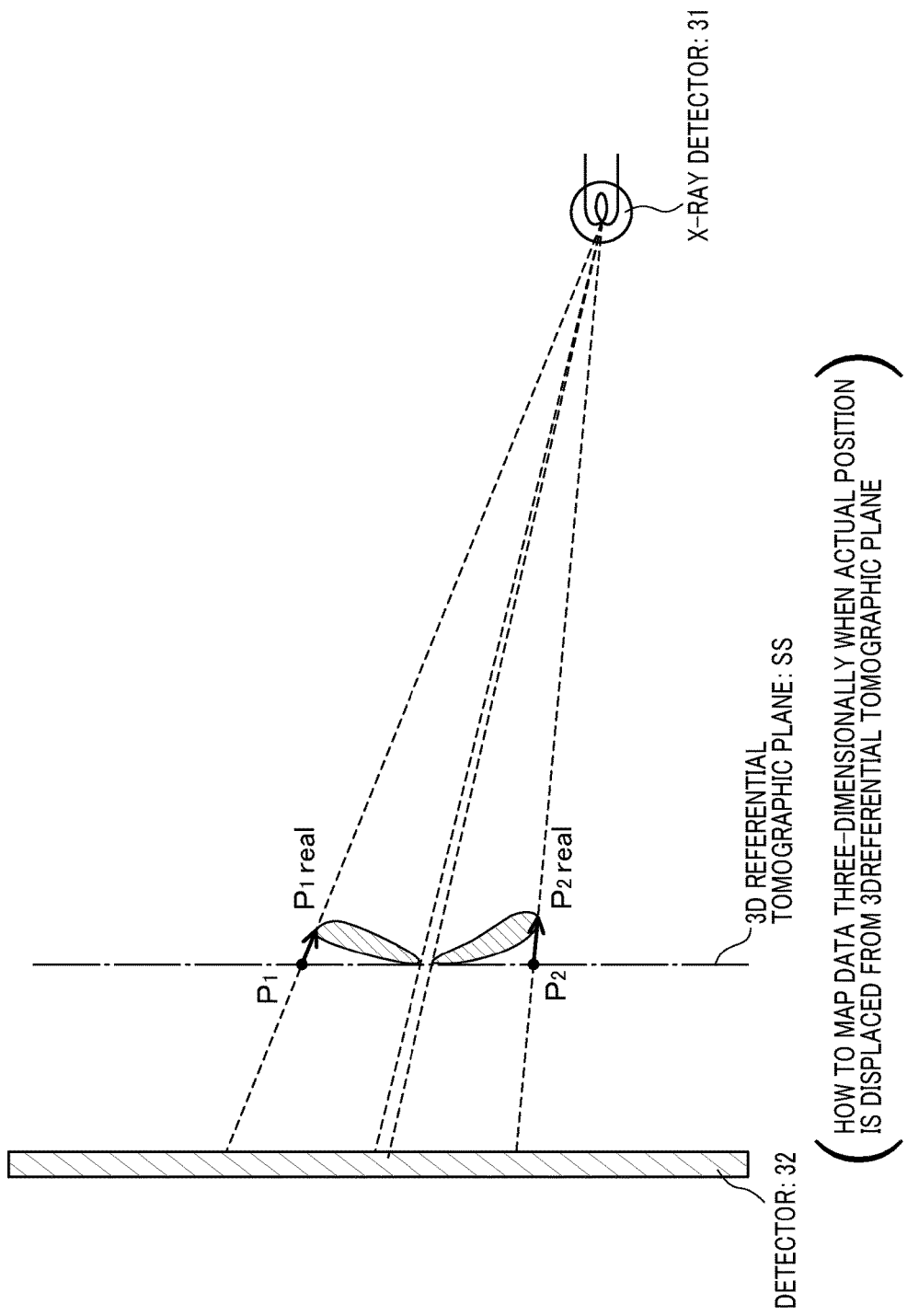
FIG. 44 is a view explaining a state where the real positions of teeth are deviated from the 3D referential tomographic plane.
Figure 45A:
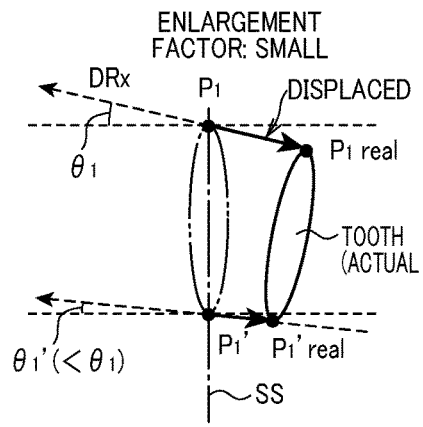
FIG. 45(A) and 45(B) are views explaining a state where a tooth is shifted from the position of the 3D referential tomographic image to its real position depending on the value of an enlargement factor.
Figure 45B:
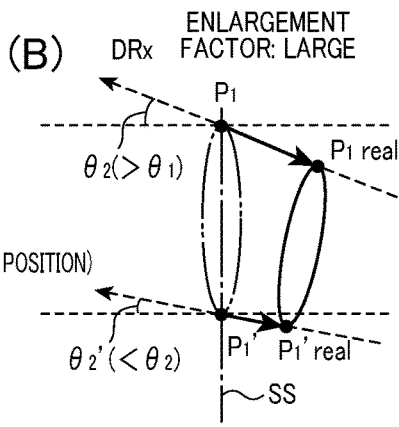
Figure 46A:
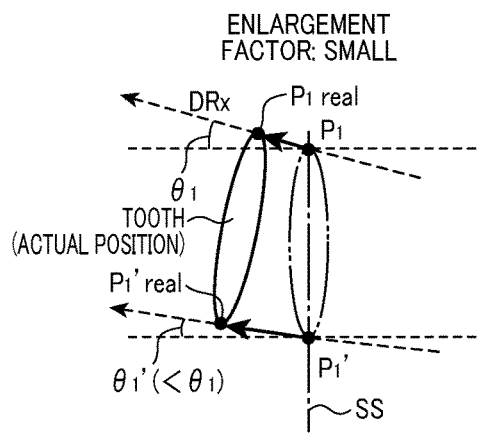
FIG. 46(A) and 46(B) are views explaining a state where a tooth is shifted from the position of the 3D referential tomographic image to its real position depending on the largeness of an enlargement factor.
Figure 46B:
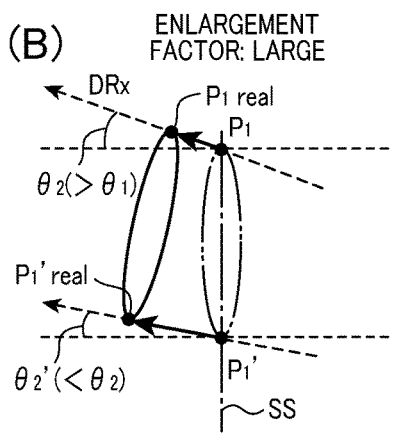

On the other hand, the phantoms 113' arranged on the outer-plane trajectory $OR_{outer}$ are constructed as shown in FIG. 19. Interestingly, the phantom 113 shown in FIG. 43 can be reversed longitudinally to provide the phantom 113' shown in FIG. 19. Namely, on each of the phantoms 113', the second and first markers 115 and 114 are laterally located close to the upper and lower ends and the third marker 115 is located longitudinally at a position close to the first marker 114. How to plant the markers are totally the same as the foregoing, so that, when the phantom 101 is assembled, it is sufficient that the planting orientations of the pillars are reversed between the reference-plane trajectory $OR_s$ and the outer-plane trajectory $OR_{outer}$. That is, sharing of the pillars can be realized, whereby manufacturing cost can be reduced. Of course, another marker indicating each of the upper and lower ends may be provided to the pillars so as not to confuse the longitudinal orientations. Such additional markers should not influence X-ray transmission trough the pillars. Another variation for preventing such confusion is that the shapes of both planting protrusion 113B and planting hole 111A are differentiated between the base 111 and the top plate 112.

As described, the first and second markers 114, 115 are different in their planting orientations and their lengths from the third marker 116. The reason is that the calibration needs measurement of different parameters so that different types of markers are needed depending on shapes according to the attributes of the parameters. In the present embodiment, one of the features is that, as described, all necessary types of markers are efficiently arranged in space on the single phantom 101. It is therefore advantageous not to use plural phantoms respectively depending on parameter types.

Although being described later, the first and second markers 114 and 115 are used for acquiring both information indicative of distance relationships among the X-ray tube 31, the detector 32, the rotation center RC, and the 3D referential tomographic plane SS and information indicative of a height position of the X-ray tube 31 to the detector 32. In contrast, the third marker 116 is used for measuring amounts (=ΔX/ΔFi) called gains described later and actual projection angles respectively corresponding to the X-ray radiation angle θ.

To be specific, the first, second and third markers 114, 115 and 116 which are present along the reference-plane trajectory $OR_s$ and the outer-plane trajectory $OR_{outer}$ are imaged in both a referential panoramic image and an outer-plane panoramic image. This situation can be understood for example at an X-ray radiation angle θ=75°. In this example, the imaging of, for example, the referential panoramic images are depicted as shown in FIG. 2O(A). That is, based on geometric relationships shown in FIG. 2O(B), the referential panoramic image depicts in black, serially from the top, the first marker 114 ($OR_s$) located at the reference-plane trajectory $OR_s$, the second marker 115 ($OR_{outer}$) located at the outer-plane trajectory $OR_{outer}$, the third marker 116 ($OR_s$) located at the reference-plane trajectory $OR_s$, the third marker 116 ($OR_{outer}$) located at the outer-plane trajectory $OR_{outer}$, the second marker 115 ($OR_s$) located at the reference-plane trajectory $OR_s$, and the first marker 114 ($OR_{outer}$) located at the outer-plane trajectory $OR_{outer}$.

Conversely, the distance of the outer-plane trajectory $OR_{outer}$ to the reference-plane trajectory ORs and the longitudinal positions of the respective markers are set so as to provide such a serial arrangement of depiction of the markers. It should be noted that in this case, the images of the markers 114($OR_{outer}$), 115($OR_{outer}$) and 116($OR_{outer}$) located at the outer-plane trajectory $OR_{outer}$ blur more than that of such markers located at the reference-plane trajectory $OR_s$. Incidentally if shift & add amounts for reconstructing a panoramic image are changed so as to focus on the outer tomographic plane, the relationship showing a degree of the blur, i.e., an optimal focusing becomes opposite to each other between both paths.

In the panoramic image, the images of the four markers 114($OR_s$), 115($OR_{outer}$), 115($OR_s$), and 114($OR_{outer}$) are depicted as lateral black lines. These images are used to measure parameters showing distance relationships among the X-ray tube 31, the detector 32, the rotation center RC, and the referential tomographic plane SS, and parameters showing a height position of the X-ray tube 31 to the detector 32. Images of the two markers 116 ($OR_s$) and 116 ($OR_{outer}$) are depicted as longitudinal black lines and used to measure a later-described amount (=ΔX/ΔFi) called gain and actual projection angles respectively corresponding to the X-ray radiation angle θ. In cases where an X-ray radiation angle is different from a designed or specified value, an actual projection angle is also different from such a value. In this case, the longitudinal black lines imaged as the two markers 116 ($OR_s$) and 116 ($OR_{outer}$) are positionally not matched to each other, being shifted from one the other in the lateral direction. Calculating such a shift amount will lead to measurement of an actual projection angle.

In this way, the phantom 101 can provide, through the single scan, necessary and sufficient positional information concerning the distances and heights of the imaging system positioned in the imaging space. Thus this phantom 101 provides general versatility that allows different types of parameters to be measured with the sole phantom.

In the foregoing phantom construction, it is not always necessary to arrange the top plate 112. However, preferably, it is desired to arrange the top plate 112, as the plural pillars 113 planted on the base 111 need to keep spatially accurate positions of the markers 114, 115 and 116. To prevent the pillars 113 from tilting, moving, and being damaged during installation and storing of the phantom, it is preferable to have the top plate 112. Alternatively, resin-made pillars just for supporting both upper and lower plates may be installed between the top plate 112 and the base 111.

(Principle of Reconstruction)

Principle of reconstruction performed by the X-ray extraoral imaging apparatus 1 will now be described mathematically.

In the embodiment, it is assumed that the rotation center RC of the pair of the X-ray tube 31 and the detector 32 approximately moves along a straight line passing the mathematical center O when the rotation angle θ=0 degrees (refer to FIG. 3). Hence, this moved distance of the rotation center RC is taken into account the reconstruction, which is one feature. In this explanation, the movement of the rotation center RC is generalized, i.e., such movement is not limited to a motion along a straight line, but applicable to any movements.

FIG. 21(A) shows a geometry in which the X-ray tube 31 and the detector 32 rotate different curved trajectories $T_S$, $T_D$ which are set around a horseshoe-shaped tooth row, in which the X-ray tube and the detector are directly opposed to each other. The X-ray tube 31 rotates along one of the trajectories, Ts, while the detector 32 rotates along the other trajectory $T_D$. In other words, the X-ray tube 31 and the detector 32 are rotated as a pair, and the center RC of a line connecting both paired components (rotation center) is also moved. FIG. 21(A) is a representative for such states where the rotation center RC moves.

It is now assumed that, as shown in FIG. 21(A), the rotation center RC of the paired X-ray tube 31 and detector 32 is present at a position O, the focus position of the X-ray tube 31 is $S_1$, the position of the center in the width direction of the detector 32 is $C_1$, the rotation radius of the X-ray tube 31 (hereinafter referred to as an X-ray tube-rotation center distance) is $R_S$, the rotation radius of the detector 32 (hereinafter referred to as a detector-rotation center distance) $R_D$, a distance from the rotation center RC, i.e., position O, to a point Q in the tooth row (hereinafter referred to as a rotation center-referential tomographic plane distance is D, and a trajectory drawn by the rotation center RC is $T_O$. The distances $R_s$ and $R_d$ are fixed amounts.

Further FIG. 21(B) shows a state where the focus position S of the X-ray tube 31 is rotated and moved from $S_1$ to $S_2$, and in response to this movement, the trajectory $T_O$ of the rotation center RC moves along a circle of a radius α at an angular speed curve ω so that the rotation center RC moves from $O(S_1)$ to $O(S_2)$. In this case, an angle $θ_1$ made between the two positions O(S1), O(S2) of the rotation center RC and the positions S1, S2 which are the focus positions is $θ_1=ωt$ (t: time). During such movement, a projected point of the point Q of the tooth row, which is projected to the detector 32, changes from $P_A(S_1)$ to $P_A(S_2)$. During this movement, the center position of the width direction of the detector 32 also moves $C_1$ to $C_2$.

Figure 22A:
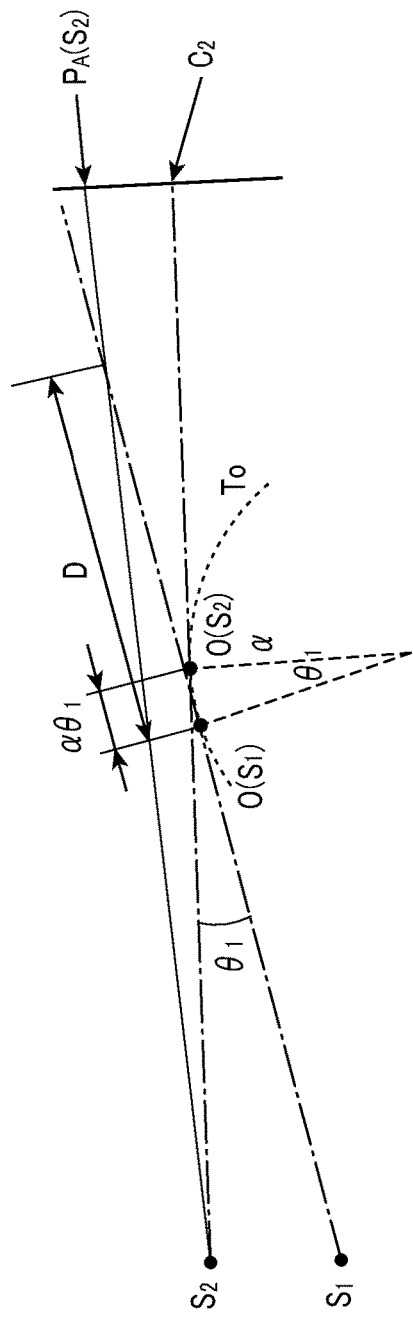
FIG. 22(A) and 22(B) are illustrations explaining the geometrical positional relationships shown in FIGS. 21 (A) and 21(B) in a numerical manner.

The geometrical relationship shown in FIG. 21(B) includes a relationship between the movement of the rotation center RC which is from the positions $O(S_1)$ to $O(S_2)$ and the trajectory $T_O$, so that such included relationship can be focused and described as shown FIG. 22(A). As a distance between both positions $O(S_1)$ and $O(S_2)$ is minute, the distance can be denoted as $θ_1α$ by using the angle $θ_1$ and the radius α. This results in that all of the rotation center positions $O(S_1)$, $O(S_2)$, the X-ray focus position S2, and the reconstruction position Q can be expressed using distance relationships, which can be shown as in FIG. 22(A). To be specific, when a distance between the X-ray tube position $S_2$ and the rotation center position $O(S_2)$ equals the X-ray tube-rotation center distance $R_s$ and a distance between the rotation center $O(S_2)$ and the detector center position $C_2$ equals the detector-rotation center distance $R_d$, a distance between the rotation center positions $O(S_1)$ and $O(S_2)$ is $αθ_1$, a distance between the rotation center position $O(S_2)$ and the reconstruction position Q is $D-αθ_1$, a segment produced by drawing a vertical line from the reconstruction position Q to the segment $o(S_2)-C2$ is $(D-αθ_1)\sin θ$, and a distance between an intersection B of the vertical line and the rotation center position $O(S_2)$ is $(D-αθ_1)\cos θ_1$.

In the present embodiment, it is a feature that calculation for calibrating parameters, which are necessary for an analysis of geometrical positional relationships of the imaging system operated in the imaging space (that is, a structural analysis) and 3D image reconstruction that extracts an actually existing position of a tooth row located in the imaging space (that is, autofocus), takes into account the distance α between the rotation center positions $O(S_1)$ and $O(S_2)$.

(Calculation of Gains)

Figure 22B:
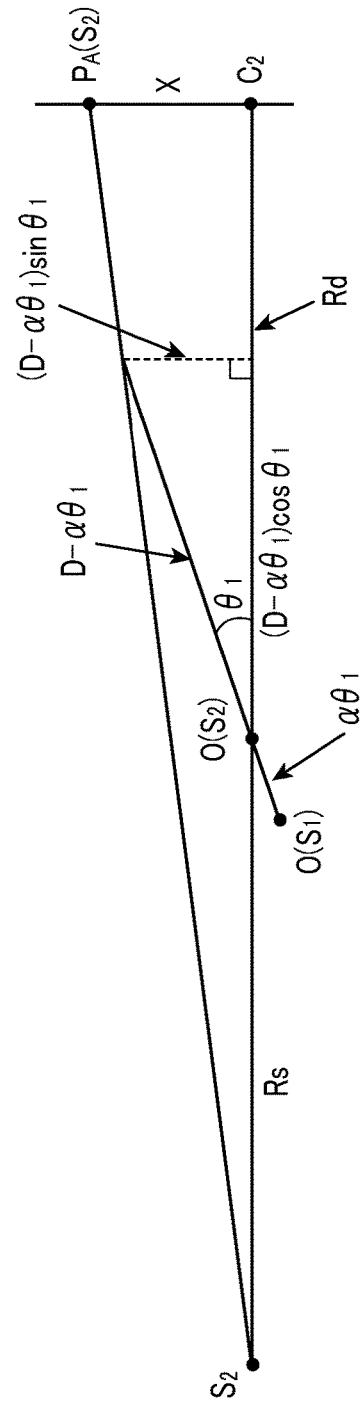

Using the distance relationships shown with FIG. 22(B), an amount which is referred to as a gain $(=ΔX/ΔFi)$ will now be obtained.

From the geometrical relationships shown in FIG. 22(B), a formula of $$x=[(Rs+Rd)/\{Rs+(D-αθ_1)\}]\cdot(D-αθ_1)\sin θ_1 \quad (1)$$

is realized. When understanding $αθ_1$ as a correction term $M(=αθ_1)$, an approximated formula of $$Δx/Δθ=\{(Rs+Rd)/(Rs+(D-M))\}(D-M) \quad (2)$$

is realized, where $θ_1$ and x are minute and negligible.

When the frame data outputted from the detector 32 are denoted as Fi, a formula of $$Δx/Δθ=(Δx/ΔFi)(ΔFi/Δθ) \quad (3)$$

is obtained, so that a formula of $$Δx/ΔFi=(Δθ/ΔFi)\{(Rs+Rd)/(Rs+(D-M))\}(D-M) \quad (4)$$

is obtained.

The left-had side $Δx/ΔFi$ of the formula (4) is called a gain (i.e., change rates in shift & add amounts). Namely this gain $ΔX/ΔFi$ shows change rates in shift & add amounts used by the tomosynthesis technique (that is, shift & add calculation), where plural frame data are mutually shifted and added under the tomosynthesis technique.

Further, in the right-hand side of the formula (4), the term $R_S+R_D$ shows a distance between the detector and the X-ray tube (the detector-X-ray tube distance), the term $R_S+(D-M)$ shows a distance between the X-ray tube and the focus (the focus-X-ray tube distance), which is corrected by an amount corresponding to the movement distance $αθ_1$ between the rotation center positions $O(S_1)$ and $O(S_2)$. Additionally, the term (D−M) shows a distance between a new rotation center position from which an amount corresponding to the movement distance αθ is deducted, and the reconstruction point Q.

In this way, a curve of gains $ΔX/ΔFi$ (simply, a "gain curve") can be calculated on the basis of the detector-X-ray tube distance $R_S+R_D$, the focus position-X-ray tube distance $R_S+(D-M)$, the rotation center-reconstruction point distance (D−M), and an angular speed curve $Δθ/ΔFi$ (refer to FIG. 26) indicating a relationship between frame data Fi and rotation angles θ. This gain curve is subjected to integration with the center of the anterior teeth located at the center of an image, a panoramic image focusing on the position apart from the rotation center RC by the distance D can be reconstructed at each of the rotation angles.

As described in JPA-2007-136163, the foregoing gain $ΔX/ΔFi$ is different in a concept of magnitudes from a gain used in normal electric circuits. In this embodiment, the larger the gain $ΔX/ΔFi$, the smaller an overlapped amount (shift amount) applied to frame data to be added pixel by pixel to each other. In this embodiment, as the gain $ΔX/ΔFi$ becomes smaller, the overlapped amount becomes larger.

In the present embodiment, parameters necessary for a structural analysis of the imaging space and for calibration are obtained using the calibration phantom and the foregoing gain formula (4). Hence, the calibration phantom will now be described in terms of its construction and functions, prior to a description of imaging.

(Calculation of Parameters)

Figure 23:
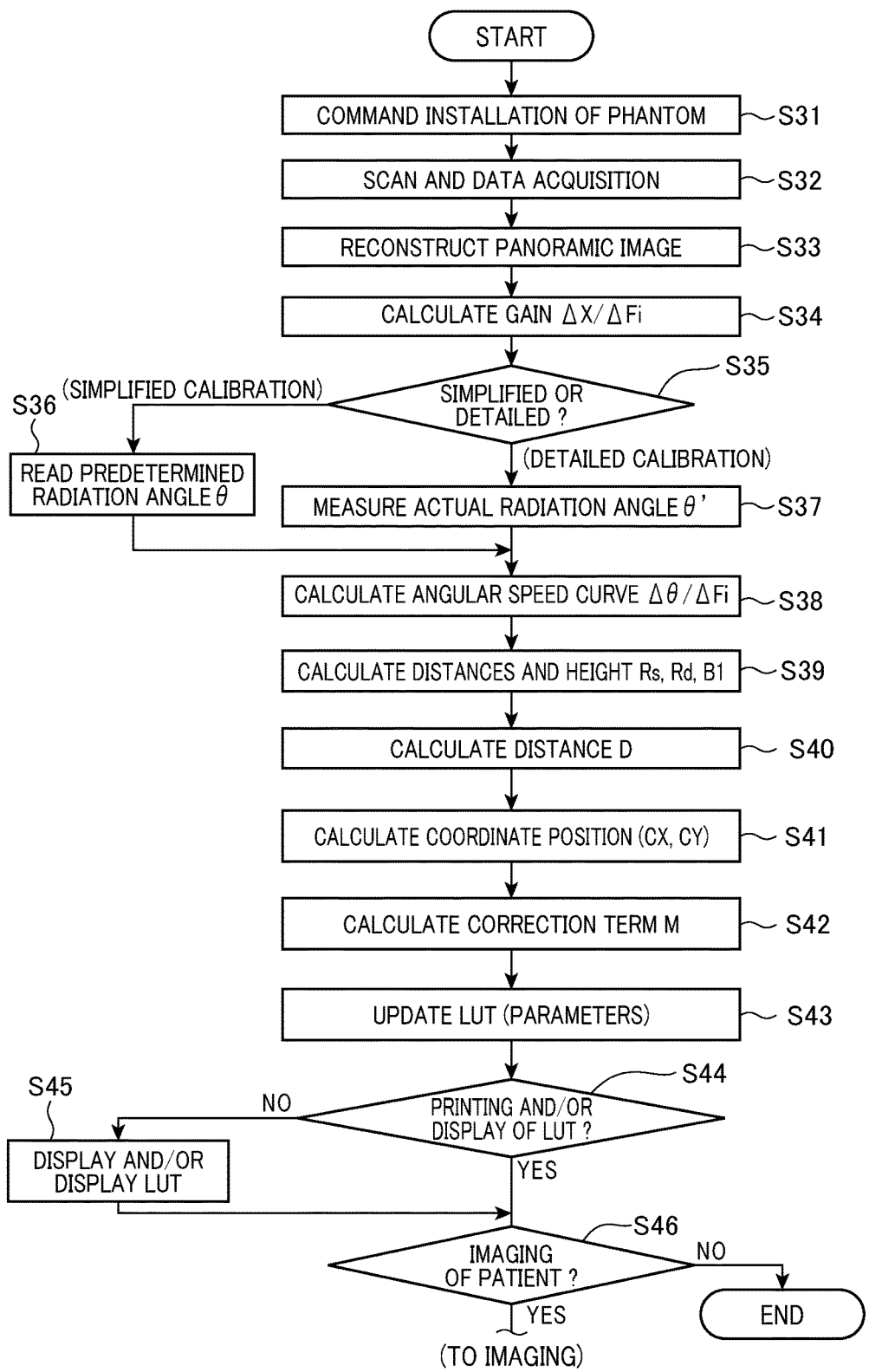
FIG. 23 is a flowchart outlining steps for structurally analyzing and calibrating an imaging space, which is executed cooperatively by a controller and an image processor.

Referring to FIG. 23, calculation for measuring the parameters necessary for a structural analysis of the imaging space and for calibration will now be described. The parameters being measured here are the X-ray tube-rotation center distance Rs, the detector-rotation center distance Rd, and the Z-axial height B1 of the X-ray tube 31 to the detector 32, which are used for the structural analysis; and the gain $\Delta x/\Delta Fi$, the X-ray radiation angle $\theta$, the angular speed curve $\Delta\theta/\Delta Fi$, the rotation center-referential tomographic plane distance D, the correction term M, and the coordinate (CX, CY) of the moving rotation center RC in the X-Y plane, which are used for the calibration.

Among them, the parameters for the calibration "$\Delta x/\Delta Fi$, $\theta$, $\Delta\theta/\Delta Fi$, D, M, (CX, CY)" are stored and updated in a look-up table LUT of the input values Fi.

Processing for calculating these parameters is performed through the following processes.

Process 1: installation of the phantom and X-ray radiography (scan) for the calibration;

Process 2: calculation of a profile of the gain $\Delta x/\Delta Fi$;

Process 3: calculation of a displacement of the X-ray radiation angle $\theta$ (i.e., an actual X-ray projection angle $\theta'$);

Process 4: calculation of the angular speed curve $\theta=f(Fi)$: $\Delta\theta/\Delta Fi$ Process 5: calculation of the parameters Rs, Rd, B1;

Process 6: calculation and update, that is, calibration of parameters $\Delta x/\Delta Fi$, $\theta$, $\Delta\theta/\Delta Fi$, D, M, (CX,CY); and Process 7: 3D reconstruction with actual positions of a tooth row depicted. These processes are performed during the performance of a flowchart shown in FIG. 23, which is performed cooperatively by the controller 55 and the image processor 54.

<Process 1>

The controller 55 commands an operator to install the phantom 101 at a predetermined position in the imaging space, via screen display and/or sound messages (step S31). The predetermined position referred here is a position on the chinrest 25 on which the jaw of a patient P will be rested during imaging.

The controller 47 then commands the apparatus to perform a calibrating scan via the operation device 48 (step S32). Responsively to this command, the controller 55 reads a program for the calibrating scan, which is previously stored in the ROM 61, into a work area of the controller. The controller 55 executes steps of the program, which makes the X-ray tube 31 with the collimator 33 and the detector 32 rotate around the phantom. During this rotation, for example, pulsed X-rays are radiated from the punctate X-ray focus of the X-ray tube 31, and the pulsed X-rays are collimated into a fan-shaped X-ray beam by the collimator 33. This X-ray beam is transmitted through the phantom, and enters the detection surface of the detector 32. Hence, the detector 32 detects the X-ray beam which has been transmitted through the phantom, and outputs at intervals (for example, 300 fps) electric digital frame data corresponding to the detected X-ray beam.

The rotation of both the X-ray tube 31 and the detector 32 is not a simple circulation around the phantom. As shown in FIG. 21(A), with the X-ray 31 and the detector 31 always kept to be opposed to each other, the X-ray 31 and the detector 31 are rotated such that the rotation center RC in a line connecting both devices positionally trances a trajectory which first moves closer to a frontal portion of the phantom and then moves away from the phantom. That is, during an actual scan, the rotation center RC moves closer to the tooth row as advancing toward the anterior teeth of the tooth row, so that the rotation center RC is positionally shifted. To allow this movement, rotated positions and angular speed curves of both the X-ray tube 31 and the detector 32 are controlled individually.

The frame data outputted from the detector 32 are temporarily stored in the buffer memory 52. The image processor 53 uses such frame data to reconstruct a referential panoramic image of the referential tomographic plane SS under the tomosynthesis technique (step S33).

<Process 2>

The image processor 54 then calculates the gain $\Delta X/\Delta Fi$ (step S34).

First, in the reconstructed referential panoramic image, the numbers of frame data $Fi_0$ is decided. This decision is performed by an operator who visually views the referential panoramic image, in such a manner that each of such reconstructed frame data provides a panoramic image in which the markers on each of the pillars of the phantom 101 are centered and depicted. As described, the pillars are arranged at each of the X-ray radiation angles $\theta$ along the referential plane positions tracing the path of the referential tomographic plane SS. Incidentally, this referential panoramic image includes images of the phantoms secured to the pillars arranged at each of the X-ray radiation angles $\theta$ along outer plane positions tracing the path of the outer plane located outside by 20 mm from the referential tomographic plane SS.

For the phantoms of each of the pillars standing at the referential plane positions, an amount of overlapping (i.e., a shift & add amount) of frame data Fi, which provides best focus, is then decided. This is also decided by the operator who visually observes the referential panoramic image during which the operation device is manipulated. This observation and manipulation is repeatedly performed by trial and error, in which frame data Fi on both sides of the center frame data $Fi_0$ are overlapped on one another to check a degree of blur in an overlapped image. In this way, the center frame data $Fi_0$ respectively directed to the markers on each of the pillars standing along the referential tomographic plane SS and optimum amounts of overlapping for each of the center frame data have been decided. Such decided data are smoothly connected with each other to obtain a profile Px of the amounts of overlapping. This profile Px is the used to obtain a gain $X/\Delta Fi$ at each of the X-ray radiation angles $\theta$ which have been set.

A modification is provided, where the amounts of overlapping are taken as an abscissa axis and statistic amounts of edges of the marker images (for example, half bandwidths) are taken as an ordinate axis. It may be possible to estimate an overlapping amount which provides a peak to the edge statistic amounts of the marker images. Such estimated overlapping amount provides an optimum overlapping amount. Hence, by positionally specifying the marker images depicted in the referential panoramic image via ROIs for example, it is possible to almost automatically calculate optimum overlapping amounts at the specified positions.

The image processor 54 then responds to a command from the controller 55 to receive a command of what type of calibration should be performed. In the present embodiment, there are provided two types of calibration. One type is a simplified calibration with which no calibration is performed for the X-ray radiation angles $\theta$, but default amounts for the respective X-ray radiation angles $\theta$, which are previously provided by the system, are employed as they are. The other type of calibration is a detailed calibration with which the phantom 101 is scanned to obtain a panoramic image and, from this panoramic image, the X-ray radiation angles $\theta$ are also calibrated. Thus, prior to calibration, the controller 55 enables the monitor 60 to display an image to ask the operator to desire which type of calibration, i.e., the simplified calibration or the detailed calibration. When receiving a command from the controller 55, the image processor 54 determines whether a desired calibration technique is the simplified type or the detailed type (step S35).

When it is determined to perform the simplified calibration, the image processor 54 reads values of radiation angles θ=0°, ±15°, ±30°, . . . , which are previously set as shown, for example, and sets those values to the radiation angles, as they are (step S36). In contrast, when it is determined that the detailed calibration technique be employed, displacements of X-ray radiation angles θ, that is, actual radiation angles θ', are calculated from a panoramic image.

<Process 3>

Then, a displaced amount $\theta_{shift}$ of each of the actual radiation angles (projection angles) θ' in relation to the X-ray radiation angles θ is calculated (step S37).

Through this calculation, similarly to that at step S34, concerning with the markers on the pillars arranged every X-ray radiation angle θ at the outer-plane positions which are along an outer tomographic plane, which is separated 20 mm outside of the referential tomographic plane SS, a gain ΔX/ΔFi for each X-ray radiation angle and a profile of the gains ΔX/ΔFi are produced based on the reconstructed referential panoramic image. The data of this profile is used to reconstruct an outer-plane panoramic image of a section separated 20 mm outside of the referential tomographic plane SS. In this outer-plane panoramic image, a physical lateral center position of each phantom on each of the pillars 113' located at the outer plane positions is decided. The lateral direction corresponds to a lateral direction in a two-dimensional referential panoramic image. This decision is also performed by an operator who visually observes the panoramic image.

The number $Fi_0$ of the central frame data imaging the markers on each pillar standing at each reference plane position has already been decided at step S34. Hence, from the lateral position (refer to FIG. 24(A)) of each marker in the outer-plane panoramic image (the lateral direction of the two-dimensional referential panoramic image), which marker is imaged in the center frame data, and from the lateral position (refer to FIG. 24(B)) of each outer-plane-positioned marker 116 in the outer-plane panoramic image, a displacement amount $P_{shift}$ between both markers in the images is calculated. This displacement amount $P_{shift}$ is converted to an actual-size displacement amount L (refer to FIG. 24(C)). Using this displacement amount L and the known distance DS (20 mm in the present embodiment) between both paths $OR_s$ and $OR_{outer}$, a displacement amount $\theta_{shift}$=arctan (L/DS) for the actual radiation angle θ' is calculated. This calculation is carried out every angle θ (=0°, ±15°, ±30°, . . . ). Hence, at each of the X-ray radiation angles θ which are set every predetermined angle, the displacement amount $P_{shift}$ for the actual radiation angle θ' can be obtained. FIG. 25 exemplifies this displacement amount $P_{shift}$.

<Process 4>

The image processor 54 then calculates a projection angle curve θ=f(Fi), i.e., the angular speed curve Δθ/ΔFi (step S38).

In the detailed calibration, the displacement amount $\theta_{shift}$ of the actual radiation angle θ', which shows a displacement from each X-ray radiation angle θ, has already been obtained. This displacement amount $\theta_{shift}$ is used to obtain a radiation angle θ' of each of the markers located along the referential tomographic plane SS. In the simplified calibration, designed default angles θ, which can be employed easily, are used without any correction.

Figure 26:
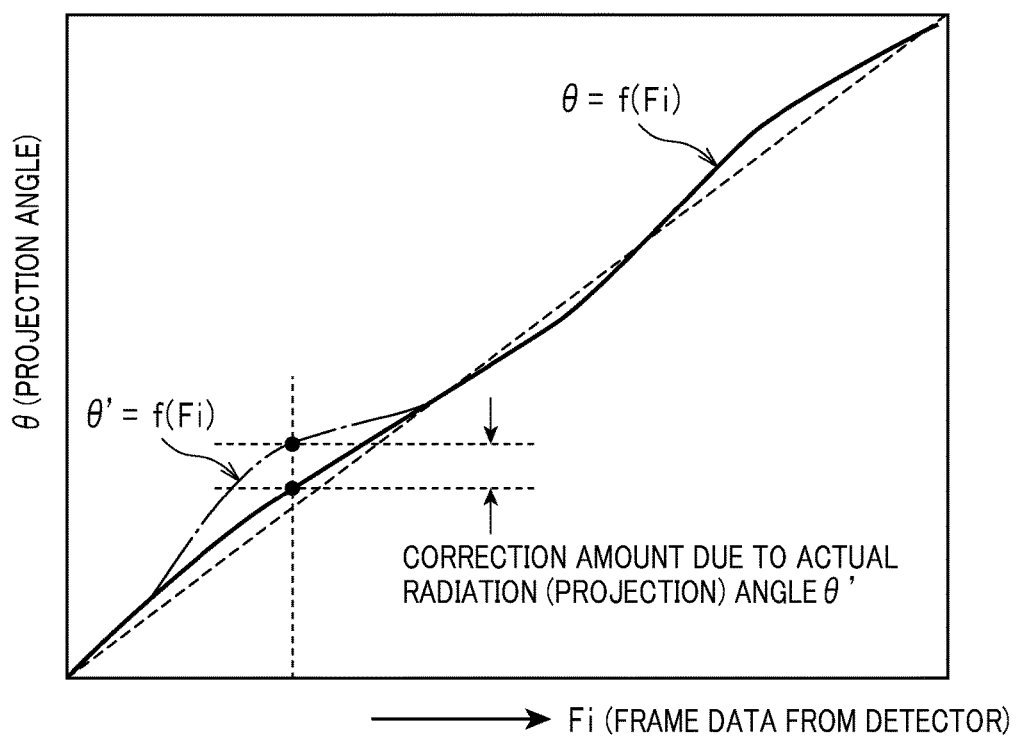
FIG. 26 is a view explaining an example of an angular speed curve and correction of the curve according to shifts in actual radiation angles.

As described, at the foregoing step S34, the number of the center frame data Fi0 centering each of the markers at the X-ray radiation angle θ, which markers are along the referential tomographic plane SS, has been known. Connecting frame data Fi acquired at the actual radiation angles θ' or the designed default radiation angles θ and smoothing the connected frame data provides a projection angle curve θ=f(Fi). FIG. 26 exemplifies this projection angle curve θ=f(Fi). In this figure, a projection angle curve θ'=f(Fi) shows that the original projection angle curve θ=f(Fi) is corrected in accordance with the actual radiation angle θ'.

<Process 5: Calculation of Constant Parameters at an X-Ray Radiation Angle θ=0 Degrees>

Then, from the panoramic image, the image processor 54 calculates, as constant parameters, the X-ray tube-rotation center distance $R_s$, the detector-rotation center distance $R_d$, and the height information B1 of the focus position of the X-ray tube, all of which are provided at an X-ray beam radiation angle of 0 degrees (step S39).

Figure 27:
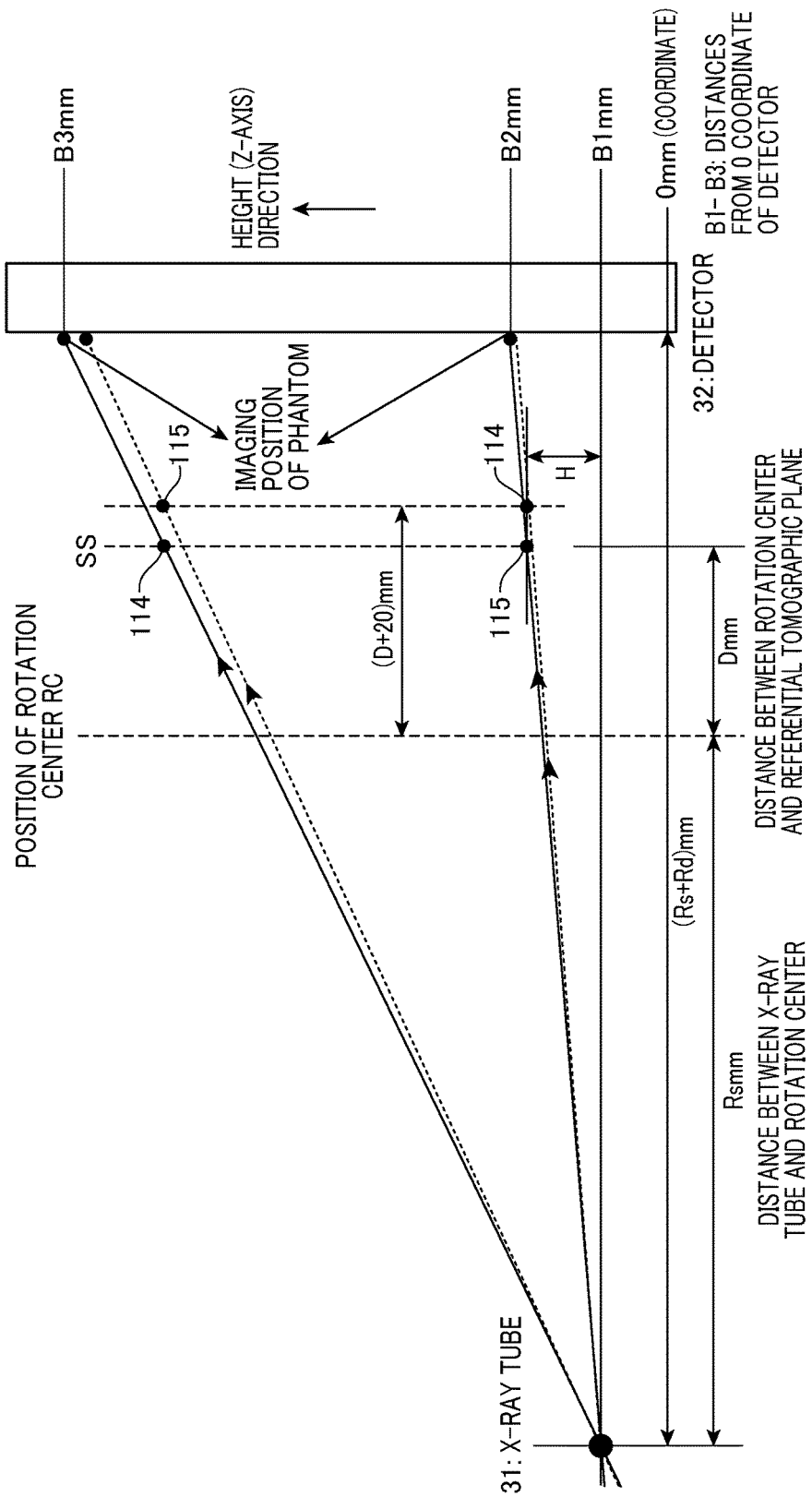
FIG. 27 is a view explaining a positional relationship between the marker at an X-ray radiation angle θ of 0 degrees and an imaging position of the marker.

As shown in FIG. 27, the X-ray tube 31 and the detector 32 are located to be opposed to each other, between of which the rotation center RC and the referential tomographic plane SS are positioned. At the position where the referential tomographic plane SS is present, the two markers 114 and 115 exist which are mutually separated 67 mm in the vertical direction. The X-ray focus of the X-ray tube 31 is small enough so as to be a punctate X-ray source (for example, a diameter of 0.5 mm). The radiation angle θ of this X-ray beam is 0 degrees. That is, the X-ray beam collimated by the collimator 33 is radiated to a central portion of anterior teeth of a tooth row assumed to be located along the referential tomographic plane SS. This X-ray beam is obliquely transmitted through the two markers 114 and 115, the transmitted beam is projected to the detection surface of the detector 32. This projection produces projected points at positions of heights B2 and B3 on the detection surface. Concretely the heights up to the markers 114 and 115 are enlarged in the longitudinal (Z-axis) direction and projected onto the projected points B2 and B3 being imaged. The lowermost end position of the detection surface of the detector 32 is set to the coordinate of 0, i.e, the origin, and the X-ray focus position has a height B1 when being calculated from a horizontal plane (X-Y plane) passing through the origin. Hence, along the detection surface of the detector 32, positions showing the origin of which coordinate is 0, the X-ray focus height B1, and the projection heights B2, B3 of the markers 114, 115 are mapped in this order from its lower end.

The foregoing gain formula (4) of $$\Delta x/\Delta Fi=(\Delta\theta/\Delta Fi)\{(R_s+R_d)/(R_s+(D-M))\}(D-M)$$

is applied to the geometrical relationship at the X-ray radiation angle of θ=0° which is pictorially shown in FIG. 27. In this X-ray radiation angle of θ=0°, as can be understood from (A) and (B) of FIG. 22, the correction term M is regarded as 0 (M=0). Hence, the formula (4) can be converted to $$\Delta x/\Delta Fi=(\Delta\theta/\Delta Fi)\{(R_s+R_d)/(R_s+D)\}D \qquad (5).$$

Based on calculation of enlargement factors of the markers 114 and 115 in the image, a relationship of $$(R_s+R_d)/(R_s+D)=(B3_{(D)}-B2_{(D)})/67=K_{(D)} \qquad (6)$$

is provided, wherein an enlargement factor $K_{(D)}$ is a known value. Specifically, this factor $K_{(D)}$ can be known from projected positions B2 and B3 detected by the detector 32, where such projected positions are given by the markers 114 and 115 located along the referential tomographic plane and at the X-ray radiation angle of θ=0°.

Similarly, a relationship of $$(R_s+R_d)/(R_s+D+20)=(B3_{(D+20)}-B2_{(D+20)})/67=K_{(D+20)} \quad (7)$$

is provided, wherein an enlargement factor $K_{(D+20)}$ is also a known value. Specifically, this factor $K_{(D+20)}$ can be known from projected positions B2 and B3 detected by the detector 32, where such projected positions are given by the markers located along the plane separated 20 mm outside of the referential tomographic plane and at the X-ray radiation angle of θ=0°.

Hence, the foregoing formulae (6) and (7) still provide $$(R_s+R_d)/(R_s+D)=K_{(D)} \quad (8)$$

$$(R_s+R_d)/(R_s+D+20)=K_{(D+20)} \quad (9).$$

When a relationship of $$X=R_s+R_d,\ Y=R_s+D \quad (10)$$

is used, there are provided $$X/Y=K_{(D)} \quad (11)$$

$$X/(Y+20)=K_{(D+20)} \quad (12),$$

from which values of X and Y can be calculated.

Further, using the formula (8), the formula (5) can be converted to $$\Delta x/\Delta Fi=(\Delta\theta/\Delta Fi)\cdot K_{(D)}\cdot D \quad (13).$$

In this formula (13), amounts of terms other than the rotation center-referential tomographic plane distance D are all known, so that the formula (13) provides such a distance D at the X-ray radiation angle θ=0°. When this distance D becomes known, the formula (10) can be used, as the values of X and Y have been known, which provides respective amounts of both the X-ray tube-rotation center distance $R_s$ and the detector-rotation center distance $R_d$ at the X-ray radiation angle θ=0°.

After obtaining the distances D, $R_s$, and $R_d$, solving two formulae of $$(B2_{(D+20)}-B1)/H=K_{(D+20)} \quad (14)$$

$$(B2_{(D)}-B1)/H=K_{(D)} \quad (15),$$

which are geometrically realized in FIG. 27, can provide values of both the position B1 of the X-ray tube 31 in the longitudinal (Z-axis) direction and the height H up to the lower phantoms from the X-ray tube 31.

<Process 6: Calculation of Functional Parameters Whose Input is Frame Data Fi, at X-Ray Radiation Angles Other than an Angle θ=0 Degrees>

Figure 28:
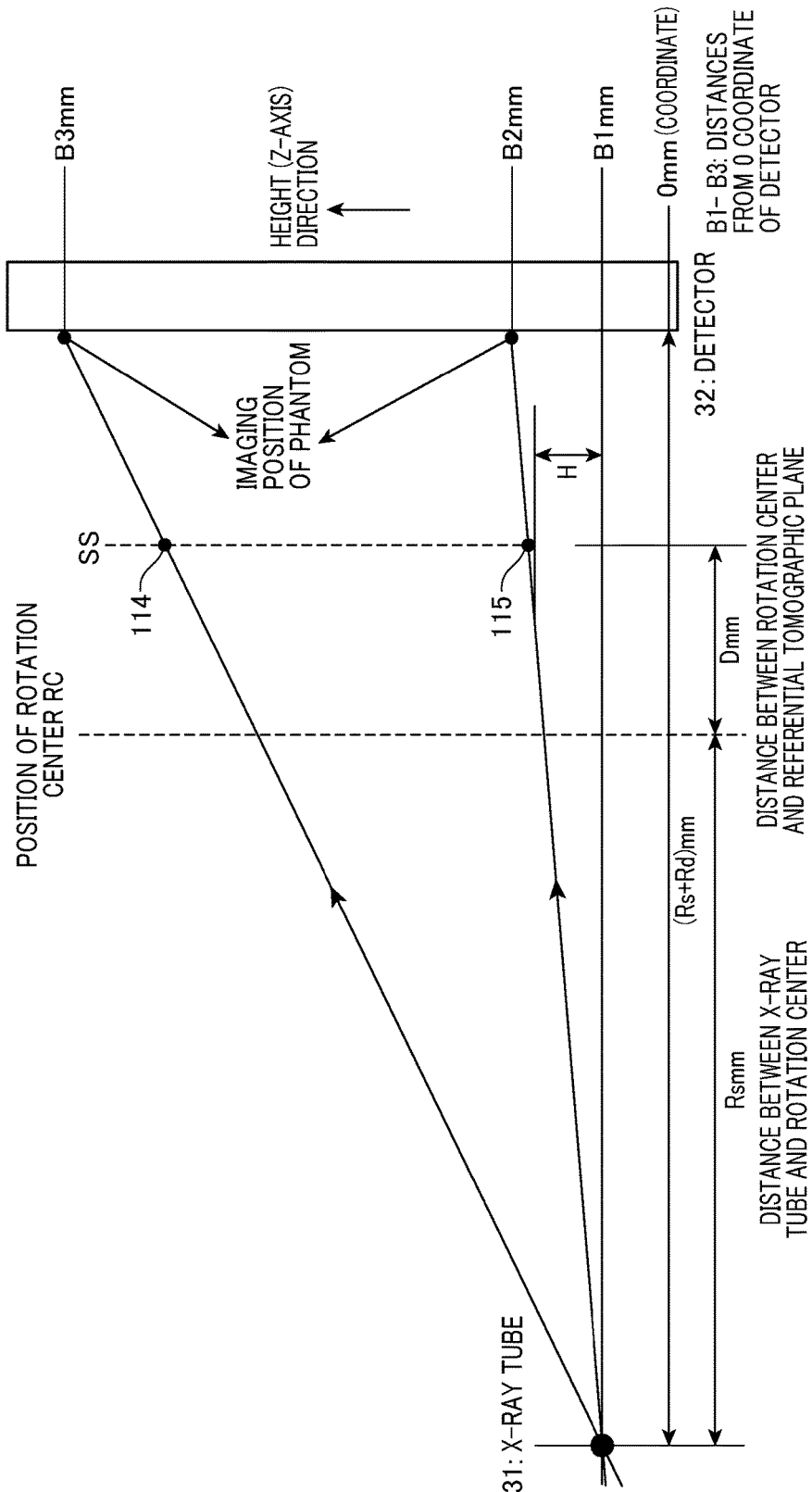
FIG. 28 is a view explaining a positional relationship between the markers at angles other than an X-ray radiation angle θ of 0 degrees and imaging positions of the markers.

In this case, at each radiation angle θ, a geometrical relationship among the X-ray detector 31, the detector 32, the rotation center RC, and the phantom (markers) can be shown as in FIG. 28.

Even at X-ray radiation angles other than the angle θ=0 degrees, the foregoing formulae (6) and (8) are realized. Hence, projected images $B3_{(D)}$ and $B2_{(D)}$ produced at positions B2 and B3 by the markers 114 and 115 are obtained at each of the radiation angles θ. Hence, using the formulae (6) and (8), the rotation center-referential tomographic plane distance D is calculated at each radiation angle θ (step S40). This known distance D are the already known X-ray radiation angle θ or its actual value θ' which has also been known are used to positional coordinates (CX, CY) of the rotation center RC (step S41).

Moreover, at the X-ray radiation angles θ other than 0 degrees, it is necessary to take the correction term M (≠0) into consideration, as can be understood from (A) and (B) of FIG. 22. Hence, it is necessary to replace the foregoing formula (4) with $$\Delta x/\Delta Fi=(\Delta\theta/\Delta Fi)\{(R_s+R_d)/(R_s+(D-M))\}(D-M).$$

As the terms other than the correction terms have been calculated, such known values are applied to the replaced formula (4) to obtain an amount of the correction term M (step S42). In this way, through steps S30 to S42, the functional parameters Δx/ΔFi, θ, Δθ/ΔFi, D, M, and (CX, CY) are calculated at each X-ray radiation angle θ.

The image processor 54 then updates the values of the functional parameters, which are stored in the image memory 53, with the newest ones calculated this time (step S43). This can calibrate the parameters necessary for 3D image reconstruction.

After the foregoing calculation for the structural analysis and calibration, the image processor 54 determines, responsively to operator's manipulation information, whether or not it is necessary to output, through printing or display, the constant parameters $R_d$, $R_s$ and B1 and the functional parameters Δx/ΔFi, θ, Δθ/ΔFi, D, M and (CX,CY), which have been calculated (step S44). If it is determined that such output is necessary, the image processor 54 prints or displays the amounts of such parameters (step S45).

After the parameter output is completed or when such output is unnecessary, the processing is continued by the computer 57. This computer determines if imaging of a patient is need interactively with the operator (step S46). When the imaging is not required, the processing is completed. In this way, the simplified type or detailed type of calibration as well as the structural analysis of the imaging space is completed.

Meanwhile, when it is required to image the jaw of a patient, 3D image reconstruction is performed which allows an accurate understanding of actual positions of a patient's tooth row located in the imaging space. In this reconstruction outlined in FIG. 29, components are projected along the oblique radiation directions of the X-ray beams, which view the X-ray tube 31 obliquely from each point of the 3D referential tomographic plane SS. This provides accurate identification of three-dimensional positions of an object being imaged (actual object), such as a tooth row. Hereinafter, imaging which involves processes for the positional identification will now be described.

<Image Reconstruction>

Figure 30:
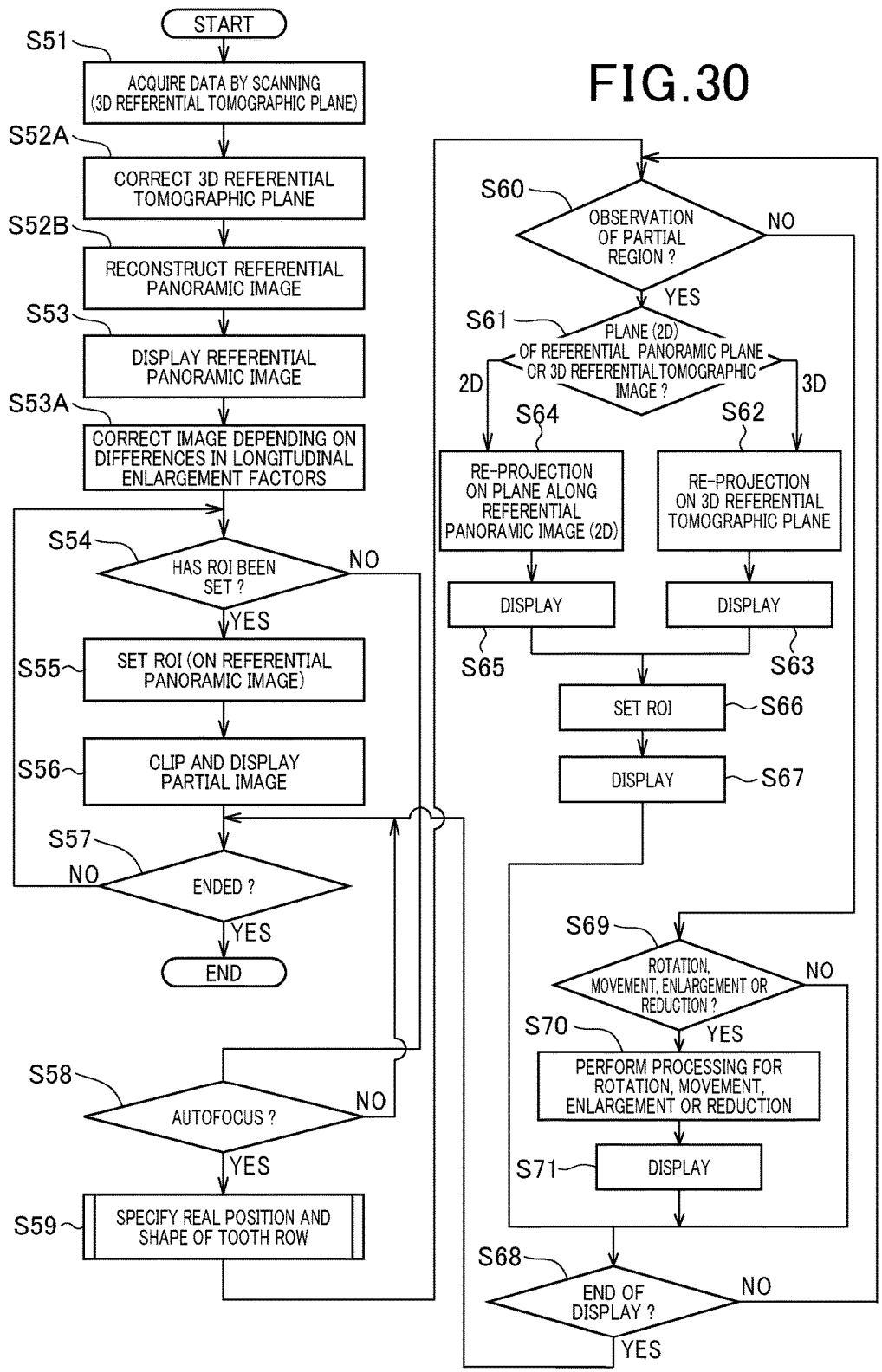
FIG. 30 is a flowchart showing an outline of processing for imaging performed cooperatively by a controller and an image processor provided in the panoramic imaging apparatus.

With reference to FIG. 30, the controller 55 and the image processor 54 cooperate with each other to perform processes for imaging will now described. As described, the processes include data acquisition by scans, reconstruction of a referential-plane panoramic image executed as a pre-process, production of a three-dimensional autofocused image (3D surface image) executed as a main process, and display and measurement of the produced image based on various display modes.

(Data Acquisition and Reconstruction of Referential Panoramic Image)

After finishing various imaging preparations such as positioning of an object (patient) P, the controller 55 responds to an operator's command given through the operation device 61 to command scanning for acquiring data (in FIG. 30, Step S51). By this command, the rotary drive mechanism 30A, the movement mechanism 3OB, and the high-voltage generator 41 are commanded to be driven according to a predetermined control sequence. As a result, during rotation of the pair of the X-ray tube 31 and the detector 32 around the jaw of the object P, the X-ray tube 31 radiates a pulsed or a continuous-wave X-ray at intervals or continuously. As described before, the pair of the X-ray tube 31 and the detector 32 is driven to rotate under a given drive condition so as to optimally focus on the 3D referential tomographic plane SS. The X-ray radiated from the X-ray tube 31 thus is transmitted through the object P to be detected by the detector 32. Accordingly, the detector 32 outputs, for example, at a rate of 300 fps, digital frame data (i.e., pixel data) in which amounts of X-ray transmission are reflected. The outputted frame data are temporarily stored in the buffer memory 52.

After the command for the scanning, the next command for the processing is provided to the image processor 54. The image processor 54 reads, from the look-up table LUT, every frame number Fi for each X-ray radiation direction, the newest amounts of the radiation angle, the angular speed curve, the rotation center-referential tomographic plane distance D, and the correction term M, and uses the read amounts to correct the 3D referential tomographic plane SS. This enables the plane SS to be positionally, part by part, changed in the front-back direction, so that the plane is smoothed (step S52A). The image processor 54 reconstructs a referential panoramic image $PI_{st}$ based on the shift & add process based on the tomosynthesis technique according to spatial positions in the corrected 3D referential tomographic plane SS, and the respective pixel values of the reconstructed image are stored (step S52B).

In this reconstruction process, the reconstructed image is multiplied by coefficients such that, similarly to the conventional, longitudinal and lateral enlargement factors at the center of the anterior teeth become equal to each other.

Figure 31:
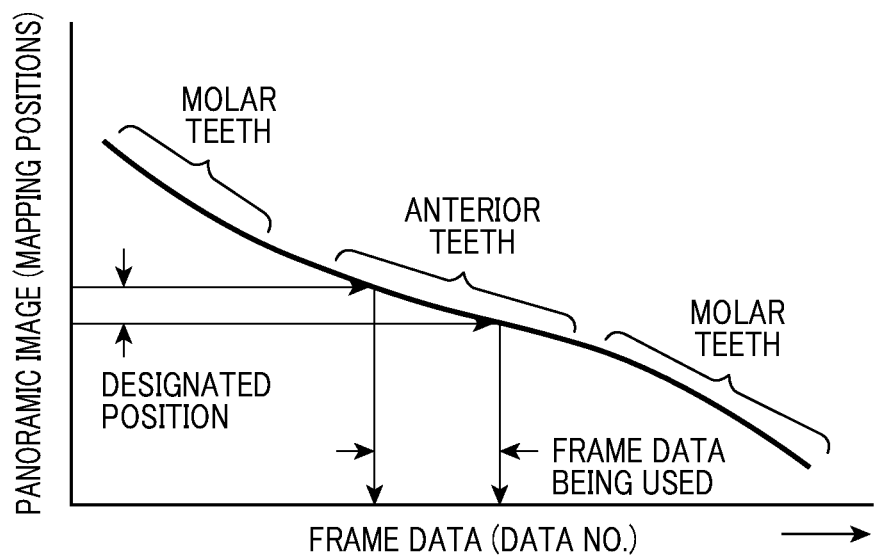
FIG. 31 is a graph explaining a relationship between frame data and mapping positions of the frame data to produce a panoramic image.

Although how to reconstruct an image is known, this will now be described a little. A set of frame data used for the reconstruction is obtained from a mapping characteristic which shows, as shown in FIG. 31 for example, mapping positions in the lateral direction of a panoramic image and a set of frame data which will be subjected to mutual addition for producing an image at the mapping positions. A curve showing this mapping characteristic consists of two curved portions which are steeper depending on molar teeth on both sides in the frame data direction (abscissa axis) and a curved portion which is gentler than those of the two curved portions for the molar teeth depending on the anterior teeth. As shown, in this projection characteristic is used to designate a desired mapping position in the lateral direction of the panoramic image. Based on this designation, the set of frame data used to produce an image at the designated mapping position and amounts of shift (i.e. degrees of overlapping necessary frame data, which is a gradient of the curve) are designated. The designated frame data (i.e, pixel values) are shifted in accordance with the designated shift amounts to be overlapped on one another and added to each other, thus providing data of a longitudinally extending image at the designated mapping position. By repeating the designation of mapping positions and shift & add calculation through the entire range in the lateral direction of the panoramic image, it is possible to reconstruct the referential panoramic image $PI_{st}$ which focuses on the 3D referential tomographic plane SS.

Figure 32:
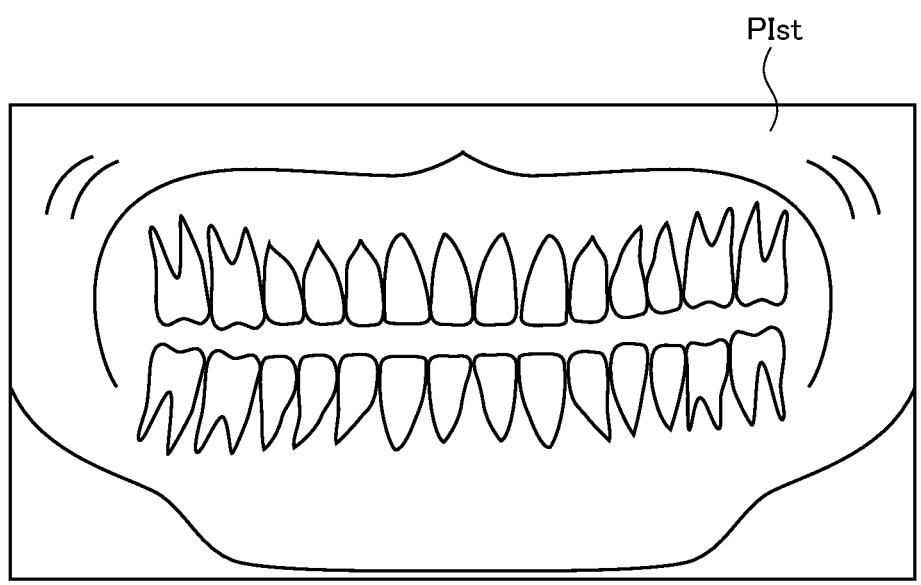
FIG. 32 is a view pictorially showing an example of a reference panoramic image.

The image processor 54 then displays the reconstructed referential panoramic image $PI_{st}$ on the monitor 60 (step S53), of which example is pictorially shown in FIG. 32.

This image $PI_{s}t$ is produced by mutually adding plural sets of frame data with shifted from each other, thus being a rectangular two-dimensional image. A process is executed in the reconstruction, which process multiplies the image with coefficients which make the ratio between the longitudinal and lateral enlargement factors equal at the center of the anterior teeth. Hence, like the conventional, image distortions in both longitudinal and lateral directions, which distortions are due to the enlargement factor, are improved to some extent in the anterior teeth. However, as advancing toward the molar areas, the ratio between the longitudinal and lateral enlargement factors deteriorate. Practically depiction of the molar areas are reduced sizes more than the actual ones.

Figure 33A:
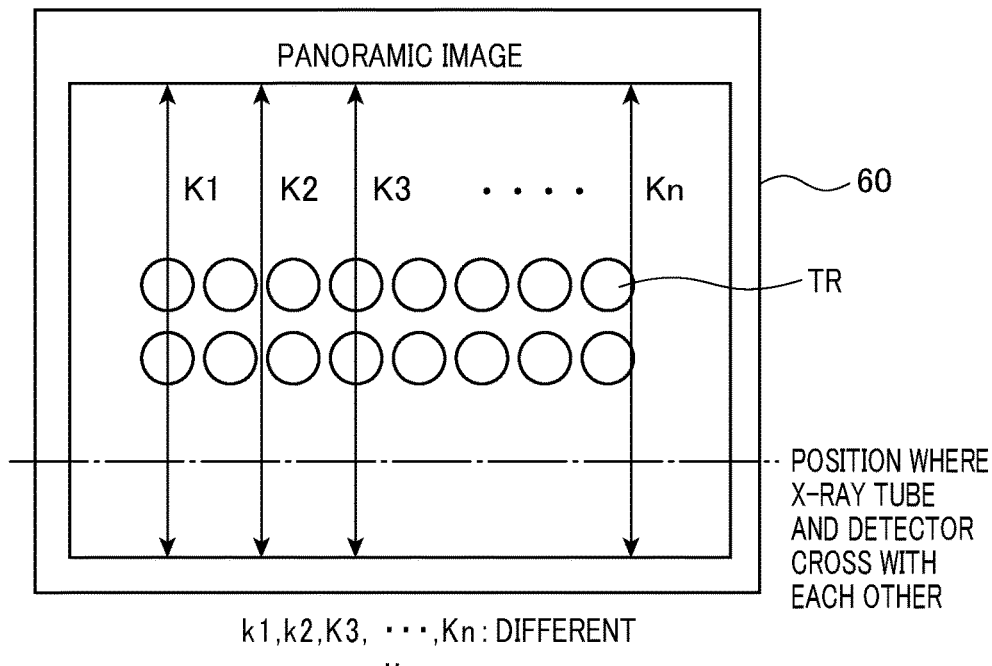
FIG. 33(A) and 33(B) are views explaining processing for correcting differences in the longitudinal enlargement factor of a panoramic image.

In addition, in the embodiment, the X-ray tube 31 and the detector 32 are rotated along the physically same circular orbit OB. Hence, also due to this fact, there are large distortions in a reconstructed image $PI_{st}$ due to changes in the longitudinal enlargement factor. Practically as shown in FIG. 33(A), the longitudinal enlargement factors K(K1, K2, ..., Kn) at respective lateral positions of the referential panoramic image $PI_{st}$ are all different from each other.

Figure 33B:
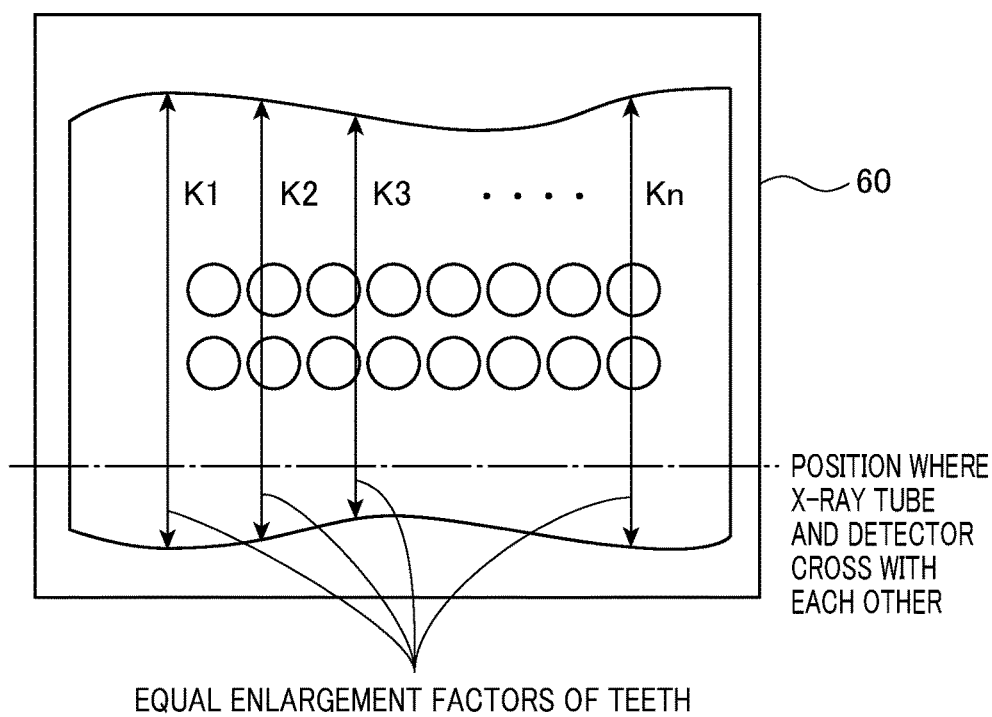

In consideration of this, the image processor 54 uses the enlargement factors K at the respective rotation angles θ, which are already obtained, to multiply each longitudinal line of pixels at each of the lateral positions with coefficients 1/K (1/K1, 1/K2, ..., 1/Kn) (step S53A). This process makes it possible that the longitudinal enlargement factors K at the respective lateral positions are almost equal to each other. As a result, as shown in FIG. 33(B), the longitudinal actual sizes and shapes of the tooth rows TR are accurately reflected in a displayed image, the contours of the image heave a little. Data of this image $PI_{st}$, whose longitudinal enlargement factors have been corrected, are again stored in the image memory 53, and used for display and 3D reconstruction.

Incidentally, the enlargement factors K may be prepared in advance in the apparatus, and such factors may be read for the foregoing correction whenever necessary.

(Setting ROI on Referential Panoramic Image)

Then, the image processor 54 determines whether or not the operator uses the operation device 61 to set a ROI (a region of interest) on the referential panoramic image $PI_{st}$ (step S54). For example, the ROI shows a rectangular partial region in which the interpreter has a special interest. The ROI is not always limited to rectangular. In addition, the ROI can be set on the panoramic image automatically focused, which will be described later.

Figure 34:
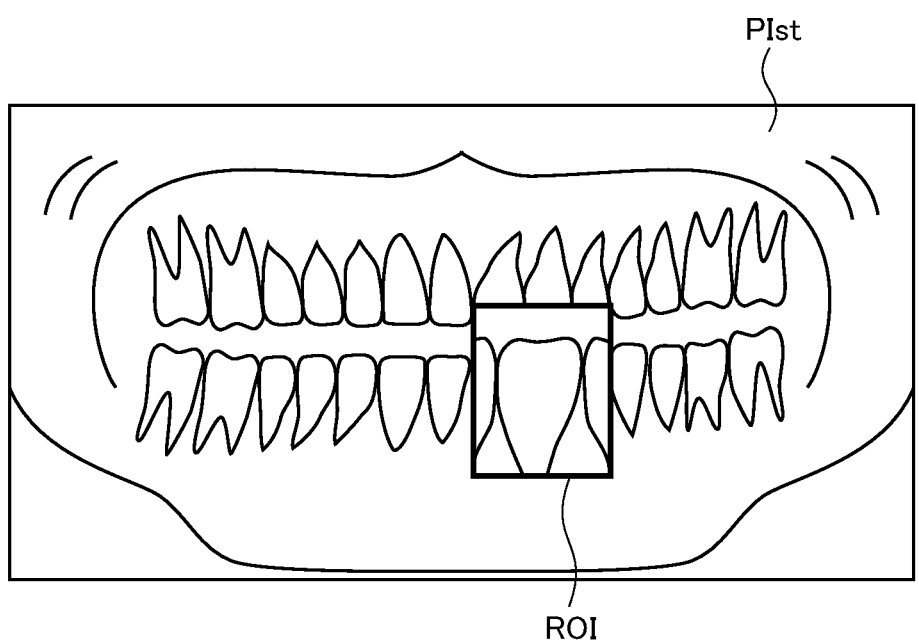
FIG. 34 is a view pictorially showing an example where a ROI is set on a referential-plane panoramic image.

When the determination at step S54 is YES, the image processor 54 responds to operational information from the operator to set the ROI on the referential panoramic image $PI_{st}$ (step S55). Then a partial image, which corresponds to the partial region sectioned by the ROI, is clipped out, and the partial image is displayed in a magnifying scale for example (step S56). For example, as shown in FIG. 34, this partial image is displayed in a superposed manner on the original referential panoramic image $PI_{st}$. Alternatively, one or more partial images can be displayed by being mapped in a template in which blocks arranged to pictorially depict partial tooth rows in both the upper and lower teeth are arranged in a predetermined order.

Then the image processor 54 determines whether or not the processing should be ended. This determination depends whether or not there is operational information from the operator (step S57). When it is determined to continue the processing (NO at step S57), the processing is returned to step S54 for repetition of the foregoing steps. In contrast, when the determination shows completion of the processing, the processing shown in FIG. 30 is ended.

Meanwhile, when the determination at step S54 is NO, that is, when the ROI will not be set, the image processor 54 proceeds to the next step. Practically, it is determined based on operational information from the operator whether or not production of a 3D autofocus image is performed as a main process (step S58). If it is determined that this production will not be performed (NO at step S58), the processing is made to return to step S57 to determine the end of the processing similarly as described.

(Specification of Position of Optimally Focused Section)

In contrast, when it is determined that production of the 3D autofocus image is desired (YES at step S58), the processing proceeds to a subroutine provided at step S59. The processing executed at step S59 provides one of the features of the present invention, which is automatic identification of the real position and shape of a tooth row. In the identification, changes of the rotation center RC are taken into consideration and longitudinal distortion of the tooth row is corrected in oblique projection directions $DR_x$ which are directed from respective pixels to the X-ray focus of the X-ray tube 31.

Figure 35:
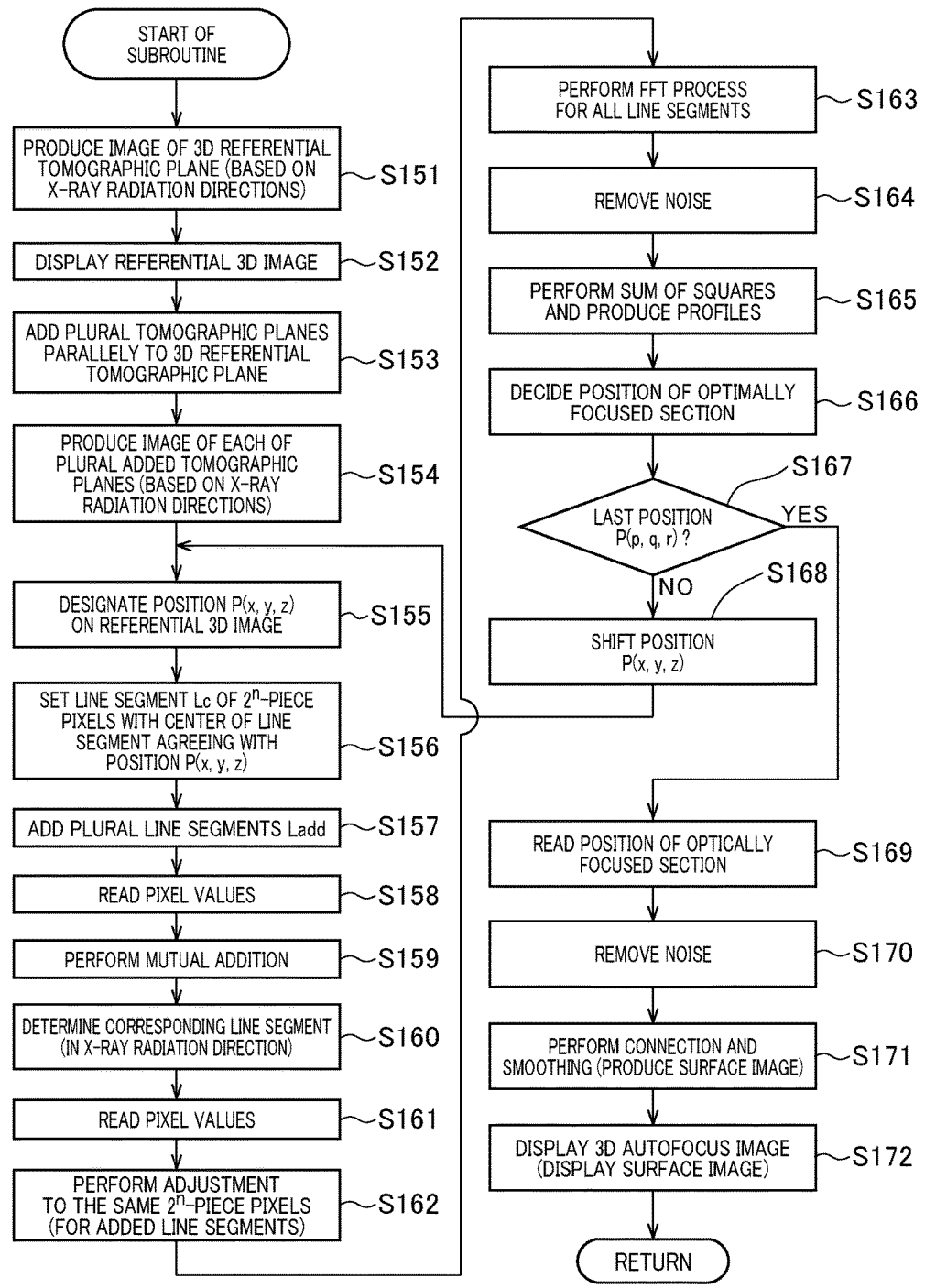
FIG. 35 is a flowchart outlining a process to identify the real positions and shapes of teeth, which is performed by an image processor.

FIG. 35 shows processing of the subroutine for such identification.

First, the image processor 54 coordinate-converts, only once, the referential panoramic image $PI_{st}$ (rectangular) onto a curved plane parallel with the 3D referential tomographic plane SS (a curved plane), thus producing a 3D panoramic image. The image processor then reads, from the look-up table LUT, every frame number Fi, both the radiation angle θ and the newest values of the coordinate position (CX, CY) of the rotation center. The image processor further extends the direction from the coordinate position (CX, CY) by an amount of the X-ray-rotation center distance $R_s$, so that the position of the X-ray tube 31 is calculated every X-ray radiation angle θ. Oblique projection directions $DR_x$ are then set which are always oriented from the respective pixels of the produced 3D panoramic image to the X-ray focus of the X-ray tube 31. After this, calculation for changing tomographic planes is performed to obtain frame data, and the obtained frame data are projected to the 3D referential tomographic plane SS through coordinate conversions along each of the projection directions $DR_x$. This provides a projected image along the curved 3D referential tomographic plane SS (step S151). The pixel values of this projected image are stored in the image memory 53.

Figure 36:
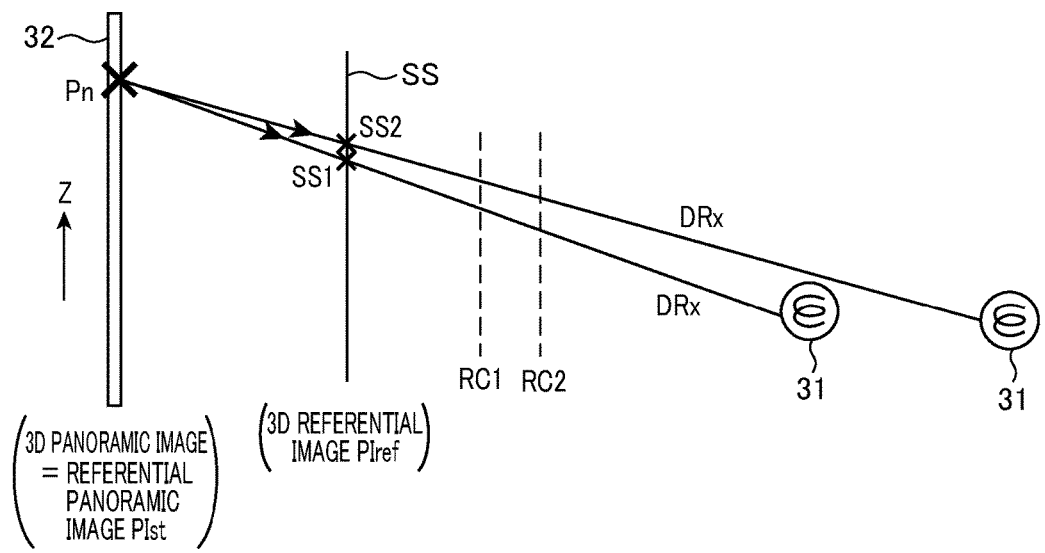
FIG. 36 is a view explaining a difference between projection angles from the same position in the Z-axis direction on a 3D panoramic image to the X-ray tube, which angles are caused by positional changes in the rotation center of the pair of the X-ray tube and the detector.

The projection is performed, as shown in FIG. 36, along each of the oblique projection directions $DR_x$ directed to the rotation center RC (RC1, RC2), that is, the position where the X-ray tube 31 is present. When referring to the example in FIG. 36, a pixel located at a position Pn in the height direction (the Z-axis direction) of the 3D panoramic image will be projected to different positions SS1 and SS2 on the image of the 3D referential tomographic image SS, which is due to differences of positions at each of which the X-ray tube 31 is located.

The projection image produced by this projection is called a 3D referential image $PI_{ref}$ in the present embodiment. This 3D referential image $PI_{ref}$ is produced by oblique projection with consideration of characteristics of the foregoing enlargement factor, in which the oblique projection is performed every pixel of the referential panoramic image $PI_{st}$. By this oblique projection, enlargement of teeth belonging to the anterior teeth, which have large enlargement factors, is corrected to have real sizes thereof, while enlargement of teeth belonging to the molar teeth on both sides of the tooth row, which have small enlargement factors, is also corrected to have real sizes thereof. Hence, in the 3D referential image $PI_{ref}$, the teeth are depicted with their real sizes and have no or less distortion which is due to the largeness of the enlargement factors caused by the moved rotation center RC during the scanning. However it should be noted that this 3D referential image PIref is produced on the assumption that the tooth row is present at and along the 3D referential tomographic plane SS. It is rare that actual teeth are present at and along the plane SS, so that it is required to perform further processing to identify the real spatial positions and shapes of the teeth.

Figure 37:
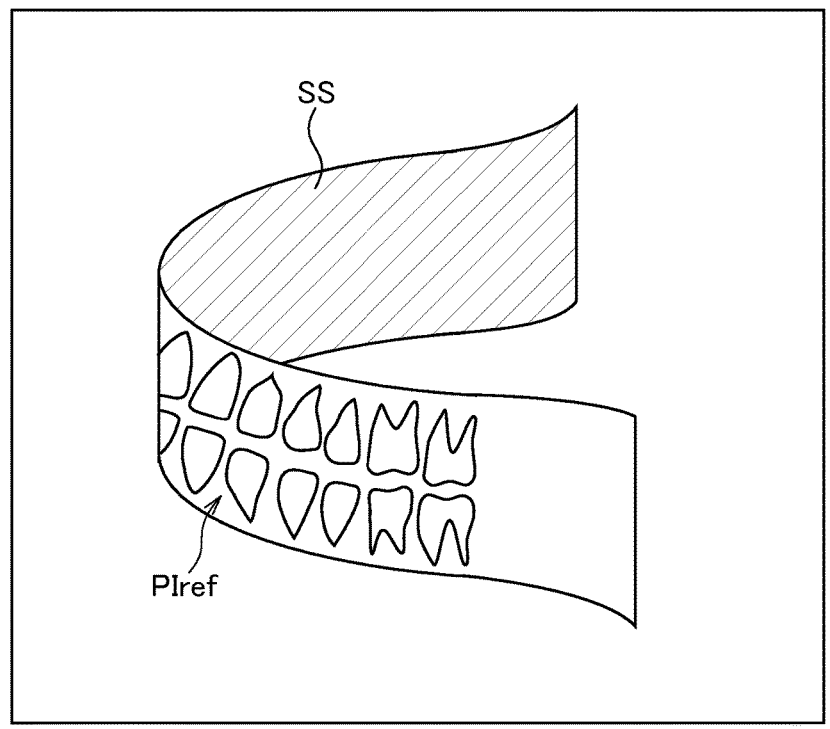
FIG. 37 is a view pictorially showing an example of a 3D reference image.

The image processor 54 displays the 3D referential image $PI_{ref}$ on the monitor for operator's reference (step S152). This is shown in FIG. 37.

Figure 38:
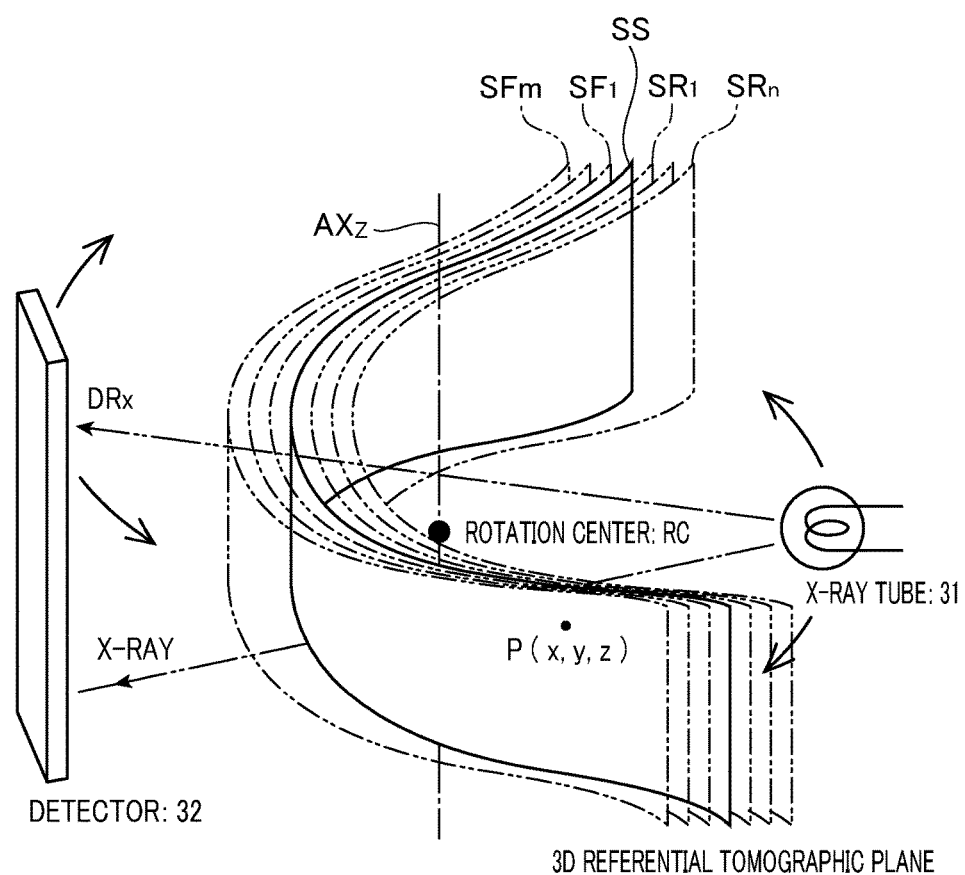
FIG. 38 is a perspective view explaining a plurality of parallel tomographic planes added to a 3D referential tomographic plane.

The image processor 54 then adds a plurality of curved and parallel tomographic planes (sections) to the 3D referential tomographic plane SS (step S153). This is shown in FIG. 38. As shown, a plurality of tomographic planes are added to the 3D referential tomographic plane SS such that such tomographic planes are set before and after the plane SS respectively in the X-ray radiation directions DRx (i.e., the depth direction of the tooth row). Each of these plurality of tomographic planes is also partially corrected in positions in the front-back directions hereof, in accordance with amounts corrected by the rotation center-referential tomographic plane distance D and the correction term M which have been applied to the 3D referential tomographic plane SS.

By way of example, plural tomographic planes $SF_m$-$SF_1$ are located on the front side of the 3D referential tomographic plane SS at intervals of D1 (for example, 0.5 mm), while plural tomographic planes $SR_1$-$SR_n$ are located on the rear side of the plane SS at intervals of D2 (for example, 0.5 mm). The intervals D1 and D2 may be equal to each other or different from each other. In addition, the number of tomographic planes to be added may be one on the front and rear sides of the plane SS respectively (i.e., m, n=1) or may be one or plural on either the front side or the rear side of the plane SS.

Incidentally, position data indicative of the virtually added tomographic planes $SF_m$-$SF_1$ and $SR_1$-$SR_n$ are previously stored in the ROM 61 together with positional data of the 3D referential tomographic plane SS, so that the image processor 54 can perform the addition through reading of the positional data and loading them into a work area of the image processor 54. The heights of the tomographic planes $SF_m$-$SF_1$, SS, and $SR_1$-$SR_n$ are decided appropriately in consideration of the maximum gradient of the X-ray radiation directions $DR_x$ and the height of the tooth row. Every time the identification processing is performed, the positions (the intervals D1, D2) of the tomographic planes to be added and the number thereof may be changed interactively.

Further, similarly to the processing at step S151, the image processor 54 calculates projection directions $DR_x$ depending on changes in the coordinate positions (CX, CY) of the rotation center RC. And along the calculated projection directions $DR_x$, the image processor 54 projects the referential panoramic image $PI_{st}$ onto each of the added tomographic planes $SF_m$-$SF_1$ and $SR_1$-$SR_n$ by obtaining frame data through calculation of changes of tomographic planes and coordinate-changing the obtained frame data (step S154). As a result, images projected to the respective added tomographic planes $SF_m$-$SF_1$ and $SR_1$-$SR_n$ are produced. The pixel values of such projection images are stored in the image memory 53.

Figure 39:
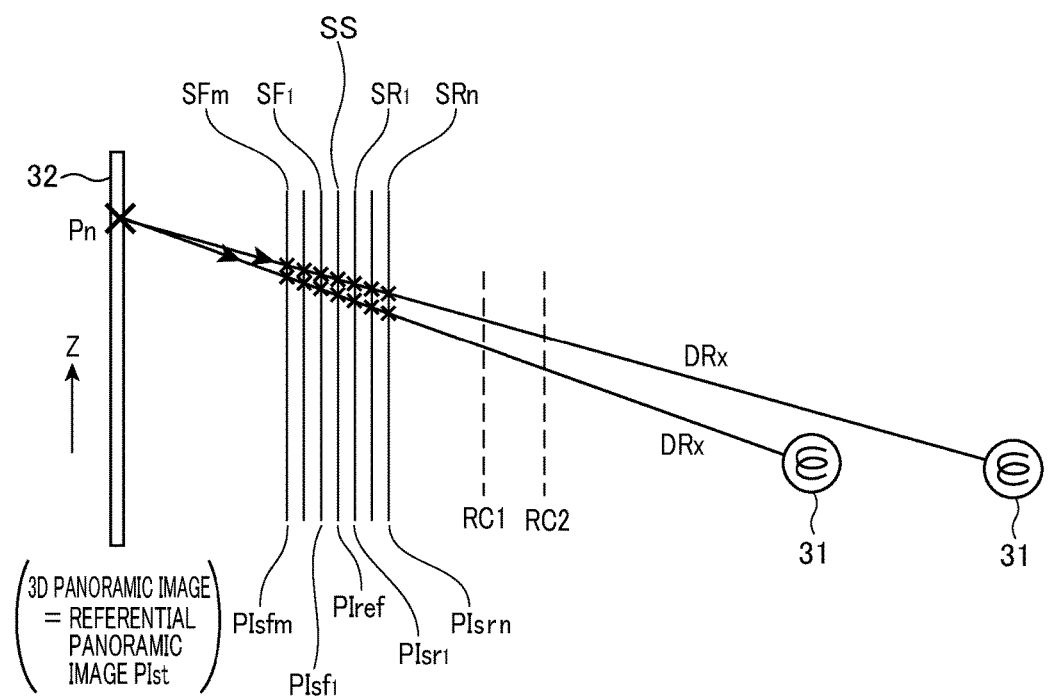
FIG. 39 is a view explaining differences of positions projected on the plurality of tomographic planes, which positions are obtained when the same Z-axial position on a 3D panoramic image is projected to portions of the X-ray tube, wherein the positional differences are caused by positional changes in the rotation center of the pair of the X-ray tube and the detector.

In the present embodiment, the produced projection images are referred to as 3D added images $PI_{sfm}, \ldots, PI_{sf1}, PI_{sr1}, \ldots, PI_{srn}$. Each of these 3D added images $PI_{sfm}, \ldots, PI_{sf1}, PI_{sr1}, \ldots, PI_{srn}$ is also produced by the oblique projections performed through the individual pixel positions of the referential panoramic image PIst, in which the oblique projections take into account of the foregoing differences in the longitudinal enlargement factors. This is exemplified in FIG. 39, in which the same pixel existing at a position Pn in the height direction of a 3D panoramic image (i.e., the Z-axis direction) is projected onto different positions on the respective 3D added images $PI_{sfm}, \ldots, PI_{sf1}, PI_{sr1}, \ldots, PI_{srn}$, which are due to differences in positions where the X-ray tube 31 is located.

Hence, the teeth depicted in the 3D added images $PI_{sfm}, \ldots, PI_{sf1}, PI_{sr1}, \ldots, PI_{srn}$ are depicted with their real sizes and distortion due to the largeness of the enlargement factors, which is due to the movement of the rotation center RC during the scanning, is removed or suppressed from such 3D added images. It should be noted however that the 3D added images $PI_{sfm}, \ldots, PI_{sf1}, PI_{sr1}, \ldots, PI_{srn}$ are produced on the assumption that the tooth row is present at and along each of the 3D added images $PI_{sfm}, \ldots, PI_{sf1}, PI_{sr1}, \ldots, PI_{srn}$.

As a modification, the plural 3D added images $PI_{sfm}, \ldots, PI_{sf1}, PI_{sr1}, \ldots, PI_{srn}$ thus produced can be displayed on the monitor 60 as three-dimensional images as they are or displayed on the monitor 60 as rectangular two-dimensional images produced through coordinate conversion.

Figure 40B:
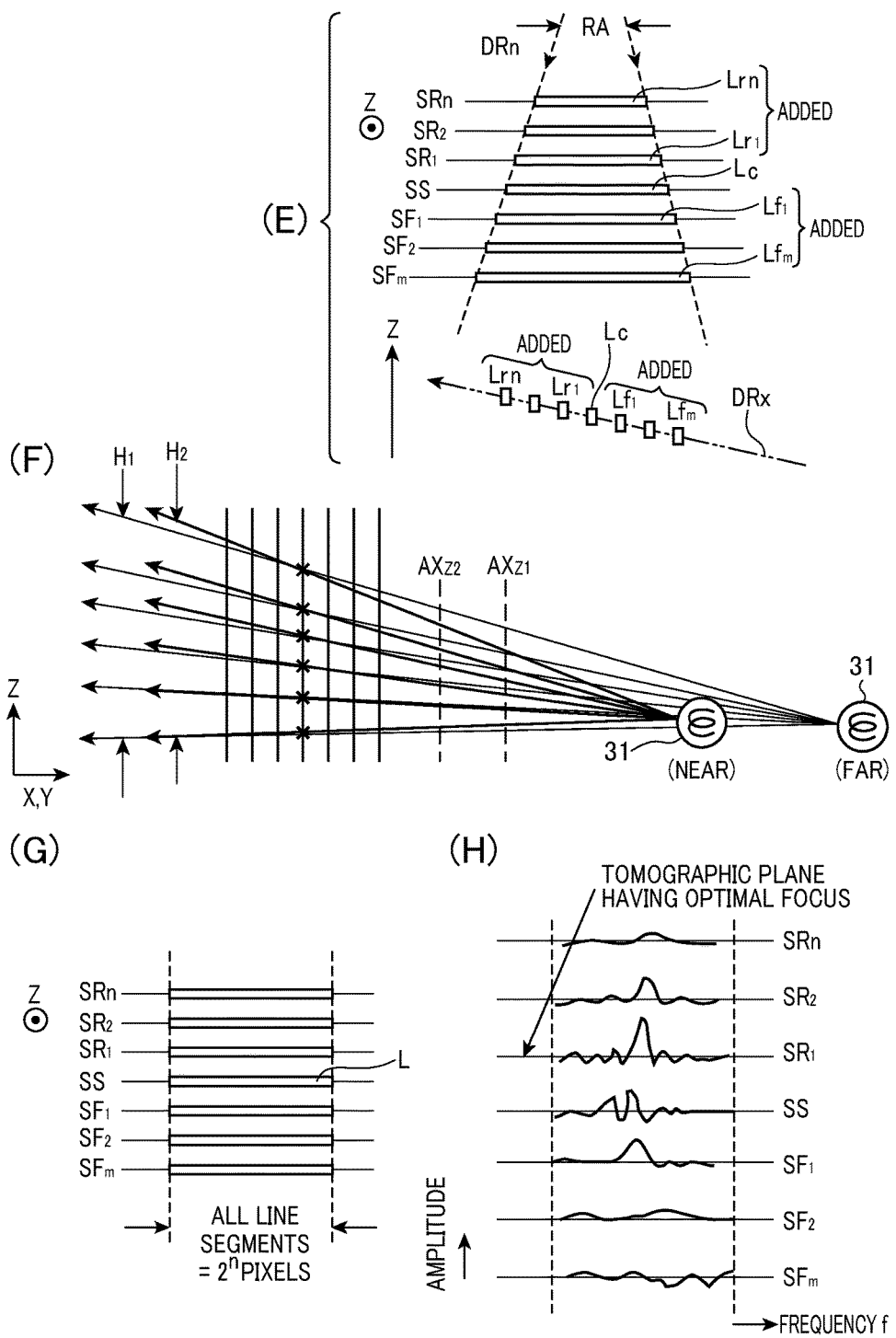
FIG. 40(B) is a view explaining, in the order of (E) to (H), the process to identify optimally-focused tomographic planes for each of positions on the 3D reference image.

The image processor 54 then designates an initial position P(x, y, z) on the 3D referential image $PI_{ref}$ that is, the 3D referential tomographic plane SS (step S155; refer to FIG. 40(A)). After this, the image processor designates a line segment Lc of a given length centering the designated position P(x, y, z) on the 3D referential image $PI_{ref}$ (step S156; refer to FIG. 40(B)). This line segment Lc has the given length corresponding to $2^n$ pieces (n=1, 2, 3, . . . ; for example 128 pieces). As modifications, the line segment Lc can be drawn along a part of the curved 3D referential tomographic plane SS so that the lien segment is curved or can be drawn in a limited range regarded as being liner.

Then the image processor 54 virtually adds plural line segments Ladd on the upper and lower sides of the designated line segment Lc(x, y, z) on the image, respectively, in which the plural line segments Ladd have the same length as that of the line segment Lc(x, y, z) (step S157; refer to FIG. 40(C)).

The image processor then reads, from the image memory 53, the pixel values $P_{ij}$ of respective $2^n$-piece pixels composing each of the foregoing line segment Lc and plural line segments $L_{add}$, and assigns the read pixel values to the respective line segments (step S158). The pixel values $P_{ij}$ have been already acquired and stored through the foregoing steps S151 and S154.

The image processor then mutually add the pixel values $P_{ij}$ of the pixels corresponding to the line segment Lc and line segments $L_{add}$ to obtain $2^n$-piece pixel values $P_{ij}*$ that composes the line segment Lc(x, y, z), the 2n-piece pixel values $P_{ij}*$ being for a frequency analysis (step S159; refer to FIG. 40(D)). This addition makes it possible to reduce statistical noise in a later-described frequency analysis of changes in the pixel values, even if the pixel values of the line segment Lc(x, y, z) originally contain the statistical noise.

Then, on each of the 3D added images $PI_{sfm}, PI_{sf1}$ and $PI_{sr1}, \ldots, PI_{srn}$, the image processor 54 calculates the spatial positions of the line segments $L_{fm}$-$L_{f1}$ and $L_{r1}$-$L_{rn}$ that face the line segment Lc(x, y, z) designated currently on the foregoing 3D referential image $PI_{ref}$ in the X-ray radiation direction DRx passing through the currently designated position P(x, y, z) (step S160; refer to FIG. 40(E)). In this case, the current center position P(x, y, z) and the length of the line segment Lc, and the rotational positions of the X-ray tube 31 during the scanning are known. Hence, it is possible to calculate an X-ray radiation range RA which is fan-shaped when being viewed in the Z-axis direction, in which this range RA is formed by connecting each of both ends of the line segment Lc to the X-ray tube 31. As a result, as long as the position P(x, y, z) is designated, the special positions of the line segments $L_{fm}, \ldots, L_{f1}$ and $L_{r1}, \ldots, L_{rn}$ limited by the X-ray radiation range in compliance with the designated position can also be designated by the image processor.

The process of step S160 to designate the position the position P(x, y, z) on the 3D referential image $PI_{ref}$ is repeated until the same process for all the positions thereon is completed. Hence, in terms of effective X-ray radiation, the X-rays radiated from the X-ray tube 31 whose position comes near and farer transmit through the virtually set tomographic planes $SF_m$-$SF_1$, SS, and $SR_1$-$SR_n$ within a range of H1 to H2 (a Z-axial range) in the fan shape (refer to FIG. 40(F)). With consideration this fact, the tomographic planes $SF_m$-$SF_1$, SS and $SR_1$-$SR_n$ themselves may be horseshoe-shaped sections having heights which change in every scanning direction and being parallel with each other.

When the line segments $L_{fm}$-$L_{f1}$ and $L_{r1}$-$L_{rn}$ have been set as above, the image processor 54 reads pixel values $P_{ij}*$ of such line segments from the image memory 53 (step S161).

As shown in FIG. 40(E), since the X-ray tube 31 has a punctate X-ray source, the X-ray radiation range RA becomes a fan shape (when being viewed along the Z-axis direction). Hence, the pixels of each of the line segments $L_{fm}$-$L_{f1}$ and $L_{r1}$-$L_{rn}$ are not $2^n$-pieces in number. Thus the image processor 54 multiplies each of the line segments $L_{fm}$-$L_{f1}$ and $L_{r1}$-$L_{rn}$ by a coefficient depending on the distances D1 and D2 in such a manner that the number of pixels of each of the added line segments $L_{fm}$-$L_{f1}$ and $L_{r1}$-$L_{rn}$ becomes equal to the number of pixels, $2^n$, of the referential line segment Lc(x, y, z). Accordingly, as pictorially shown in FIG. 40(G), all the line segments $L_{fm}$-$L_{f1}$, Lc and $L_{r1}$-$L_{rn}$ are formed to be parallel with each other and to have the same number of pixels, $2^n$.

After this, the image processor 54 applies a frequency analysis to changes in the values of pixels of each of all the line segments $L_{f1}$-$L_{fm}$, Lc, and $L_{r1}$-$L_{rn}$ (step S163). Thus, as shown in FIG. 40(H), as to the line segments $L_{fm}$-$L_{f1}$, Lc and $L_{r1}$-$L_{rn}$, there are provided analyzed results consisting of an abscissa axis showing frequencies and a vertical axis showing Fourier coefficients (amplitudes).

In the present embodiment, the frequency analysis is performed using fast Fourier transformation, but wavelet transformation may be adopted as such frequency analysis. Moreover, instead of such frequency analysis, a Sobel filter to calculate the first derivation for edge extraction can be used for the equivalent process to the above. In using this filter, the position of a tomographic plane which provides an edge with a maximum filtered value can be regarded as an optimally focused position.

Figure 41:
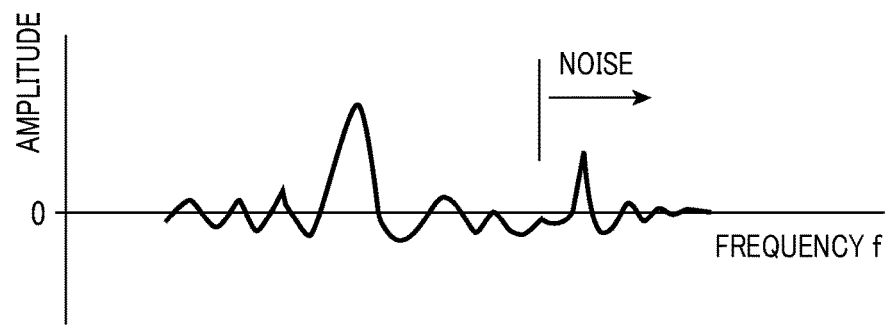
FIG. 41 is a graph exemplifying a frequency analysis result in an identification process for the optimally focused positions.

The image processor then removes noise from the frequency analyzed results for all the line segments $L_{f1}$-$L_{fm}$, Lc, and $L_{r1}$-$L_{rn}$ (step S164). FIG. 41 exemplifies the frequency analyzed characteristic for one line segment. Coefficients of frequency components which belong to a given frequency range beyond a maximum frequency of the analysis are removed, with coefficients of the remaining high-frequency components adopted. The reason for such removal is that frequency components which are present in the given frequency range beyond the maximum frequency provide noise components.

Further the image processor 54 calculates sums of squares for the coefficients of the frequency analyzed characteristic of each of the line segments, and produces a profile having a vertical axis to which the values of sums of squires are assigned and an abscissa axis to which the positions of the respective tomographic planes $SF_m$-$SF_1$, SS, and $SR_1$-$SR_n$ are assigned, where the X-ray radiation direction $DR_x$ passing through the initial position P(x, y, z)=P(0, 0, 0) passes through the positions of such tomographic planes (step S165). This profile is exemplified in FIG. 41. In this profile, the positions of the tomographic planes mean the positions the plural tomographic planes $SF_1$-$SF_m$, SS, and $FR_1$-$FR_n$ in the X-ray radiation direction $DR_x$ (i.e., the depth direction of the tooth row).

Figure 42:
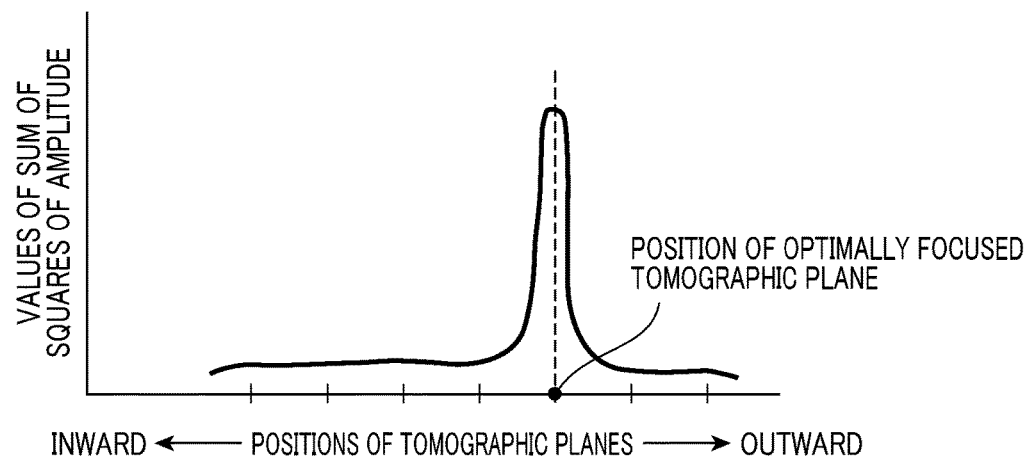
FIG. 42 is a graph exemplifying the position of an optimally focused tomographic plane obtained in the identification process for the optimally focused positions.

FIG. 42 exemplifies, as typical patterns, a plurality of types of profiles PR1, PR2, PR3 and PR4 respectively showing substances composed of enamel, cancellous bone, air and bite blocks. If there is a substance composed of enamel, i.e., tooth, anywhere in the X-ray radiation direction $DR_x$ that passes through the currently designated position P(x, y, z), the profile PR1 has a sharp peak. If there is cancellous bone in that X-ray radiation direction $DR_x$, the profile PR2 has a gentle convex curve. Similarly, if there exists only air in that X-ray radiation direction $DR_x$, the profile PR3 tends to show a curve having no specific peaks. Moreover, when the bite block is present in that X-ray radiation direction $D_{Rx}$, the profile PR4 exhibits two sharp peaks. Of such two peaks, one appearing inward (on the X-ray tube side) in the X-ray radiation direction DRx shows that the substance thereat is enamel, while the other appearing outward (on the detector side) shows that the substance thereat is the bite block. Data indicating the patterns of the profiles shown in FIG. 42 are previously stored, as reference profiles, in the ROM 61 in the form of a reference table.

Hence, the image processor 54 refers to the reference table to specify an optimum focused position of the tooth in the X-ray radiation direction DRx passing through the currently designated position P(x, y, z) (step S166).

That is, a pattern recognition technique is used to determine that the profile obtained in the last step S165 corresponds to which of the reference profiles PR1-PR4.

First, when the obtained profile is the reference profile PR2 or PR4, such a profile is withdrawn from the consideration. In contrast, when the obtained profile corresponds to the reference profile PR1 (i.e., enamel), it is identified that the section position showing its peak, i.e., the position of any of the plural tomographic planes $SF_1$-$SF_m$, SS, $FR_1$-$FR_n$, is optimally focused. Moreover, when the obtained profile is fit to the reference profile PR4, it is also identified that an inward sectional position expressing a peak (a sectional position showing enamel on the X-ray tube side), in other words, the position of any of the plural tomographic planes $SF_1$-$SF_m$, SS, FR1-$FR_n$, is optimally focused.

By the foregoing specifying steps, it is identified that a portion of the tooth depicted at the currently designated position P(x, y, z) is actually present at which position in the depth direction. In effect, a tooth portion depicted on the 3D referential image $PI_{ref}$ along the 3D referential tomographic plane SS may be present on the front or rear sides of the plane SS. The real position of the tooth portion in the imaging space is specified precisely by the foregoing specifying steps. In other words, it can be understood that a tooth portion depicted on the 3D referential image $PI_{ref}$ under the condition that the tooth portion is on and along the 3D referential tomographic plane SS is shifted to its real special position by the foregoing specifying steps.

Figure 47:
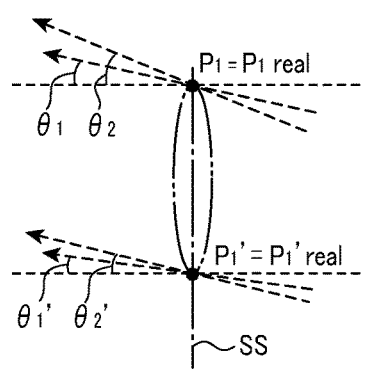
FIG. 47 is a view explaining a state where a tooth is shifted from the position of the 3D referential tomographic image to its real position depending on the largeness of an enlargement factor.

As a result, as shown in FIGS. 44-47, every time the position P(x, y, z) is designated, a position P1 on the 3D referential tomographic plane SS (i.e., in the 3D referential image $PI_{ref}$) is shifted to a position $P1_{real}$ (or a position P2 is shifted to a position P2real). In particular, the positions of the line segments $L_{fm}$-$L_{f1}$ and $L_{r1}$-$L_{rm}$ which are set on the plural added tomographic planes $SF_m$-$SF_1$ and $FR_1$-$FR_n$ are set in consideration of the oblique angle θ of each of the X-ray radiation directions $DR_x$. Thus, the shifted position $P1_{real}$ in the case of a smaller oblique angle θ (refer to FIGS. 45(A) and 46(A)) becomes lower in the Z-axis direction than in the case of a larger oblique angle θ (refer to FIGS. 45(B) and 46(B)). Accordingly, the shifted position $P1_{real}$ can be compensated in distortion depending on the oblique X-ray radiation angle θ, i.e., the largeness of the enlargement factor. Incidentally as shown in FIG. 47, when the tooth is present at and along the 3D referential tomographic plane SS, a relationship of $P1=P1_{real}$ is met. In this case, the 3D referential tomographic plane SS, at and along which it is assumed that the tooth is present, provides a real position, thus providing a shift amount of zero.

The image processor 54 then proceeds to step S165, at which data indicating the real position of the tooth portion is stored every position P(x, y, z) in the work area thereof.

In this way, as to the currently designated position P(x, y, z) on the 3D referential image $PI_{ref}$ (i.e., the 3D referential tomographic plane SS), practically, in this description, the first designed initial position P(0, 0, 0), the specification is performed in the depth direction passing through the initial position P(0, 0, 0). This specification is filtering to check whether or not there is a portion of the tooth (enamel). And when it is checked that there is such a tooth portion, an optimally focused position for the tooth part is specified in the depth direction.

Figure 48:
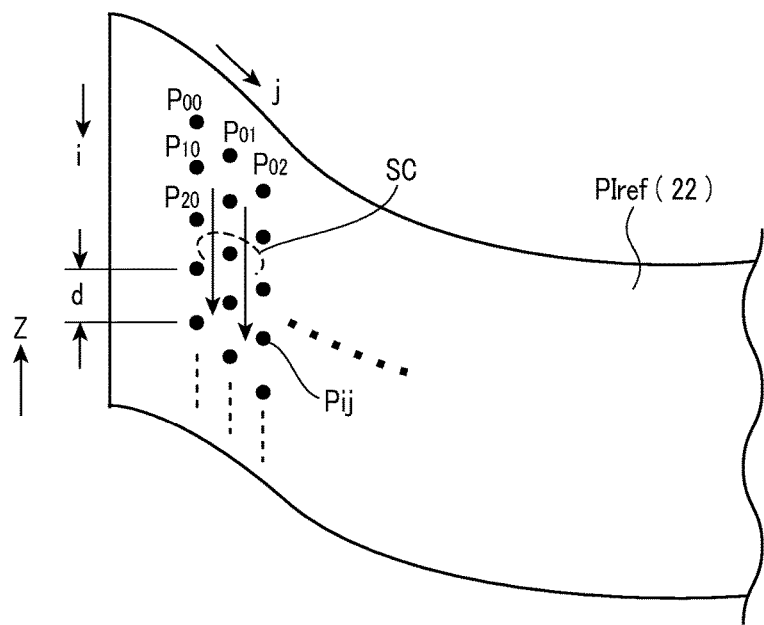
FIG. 48 is a perspective view explaining a process for moving processing points on the 3D reference image in order to perform the position identifying process.

After this, as shown in FIG. 48 for example, the image processor 54 determines whether or not the foregoing specifying steps has been completed at all determination points (sampling points) P previously set on the 3D referential image $PI_{ref}$ (step S167). This determination is executed by checking whether or not the currently processed position P(x, y, z) is the last position P(p, q, r). If this determination is NO which shows the specifying steps have not been competed at all the determination points P, the image processor 54 shifts the determination point P(x, y, z) by one (step S168), before returning to the foregoing step S155 to repeat the foregoing series of specifying steps.

As shown in FIG. 48, the plural determination points P are previously mapped with given intervals on the 3D referential image $PI_{ref}$ (i.e., the 3D referential tomographic plane SS). In the example shown here, along both the vertical direction i and the horizontal direction j of the 3D referential image $PI_{ref}$, the positions P are mapped at the same given intervals d in the vertical and horizontal directions. Alternatively, the internals d may be differentiated between the vertical and horizontal directions i and j from each other. The direction along which the shift is carried out at step S168 may be any of the vertical, horizontal and oblique directions on the 3D referential image $PI_{ref}$. As shown in FIG. 48, the shift can be made along the first vertical direction i, and the line is transferred in the horizontal direction j to repeat the shift in the second vertical direction i. This shifting manner is repeated regularly (refer to a reference numeral SC in the figure). Oppositely to this, the shift can be made along the horizontal direction j, and the line is transferred in the vertical direction i to repeat the shift in the horizontal direction. Moreover, the shift may be performed obliquely.

Meanwhile, when the foregoing specifying steps have completed for all the plural determination points P, the determination at step S167 reveals YES during the repeated processing. This means that, every determination point P, an optimally focused sectional position has been detected in the depth direction passing through the position P on the 3D referential tomographic plane SS (including determination whether or not there is an optimally focused position). In this case, the processing proceeds to a connection process of the optically focused sectional positions.

<Process to Connect Optimally Focused Sectional Positions>

Figure 49:
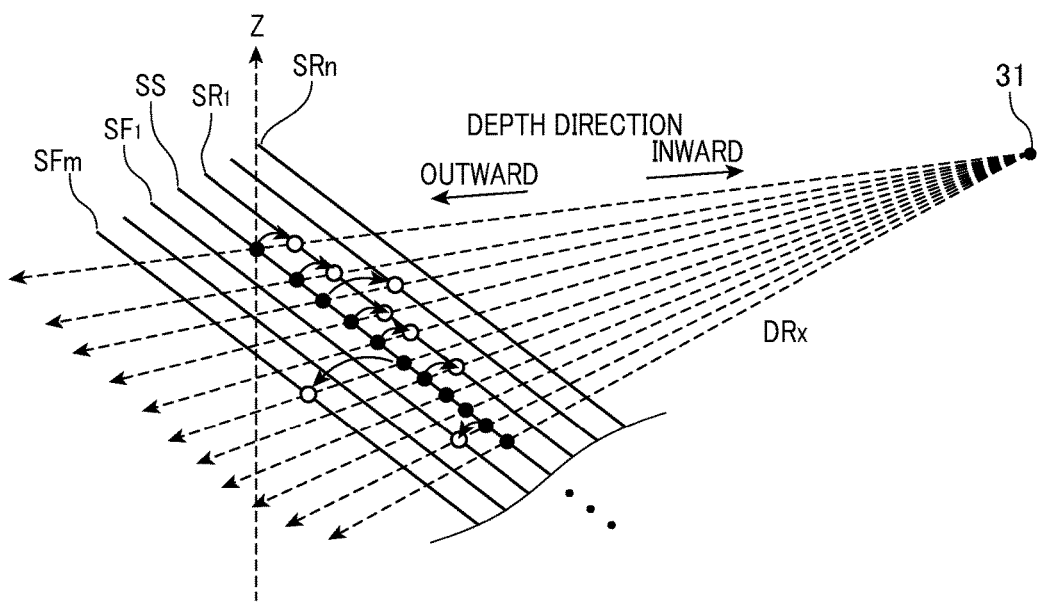
FIG. 49 is a perspective view explaining identification of the position of an optimally focused tomographic plane being identified every processing point and its abnormal identification.

When it is determined YES at the foregoing step S167, the image processor 54 reads data indicative of the optimally focused sectional positions specified and stored at step S165 (step S168). The data of these sectional positions show positions in each of the X-ray radiation directions $DR_x$ passing through each of the determination points P(x, y, z). This is pictorially exemplified in FIG. 50. In this drawing, filled circles indicate determination points P(x, y, z) on the 3D referential image $PI_{ref}$ (i.e., the 3D referential tomographic plane SS). In this case, the vertical and horizontal directions of the curved 3D referential image $PI_{ref}$ are denoted by (i, j). In FIG. 49, as shown by open circles, for example, an optimally focused sectional position at a determination point $P(x_{00}, y_{00}, z_{00})$ for i, j=0, 0 is read as a position actually preset at the position of a tomographic plane SR1, which is shifted inwardly by one section (toward the X-ray tube side). An optimally focused sectional position at a determination point $P(x_{01}, y_{01}, z_{01})$ for i, j=0, 1, which is next to the determination point for i, j=0, 0, is read as a position also actually present at the position of the tomographic plane SR2, which is shifted inwardly by one section. Furthermore, an optimally focused sectional position at a determination point $P(x_{02}, y_{02}, z_{02})$ for i, j=0, 2, which is next to the determination point for i, j=0, 1, is read as a position actually present at the position of a tomographic plane SR3, which is shifted inwardly by a further one section. In FIG. 49, for the sake of an easier understanding the process at step S168, only one position in the Z-axis direction (i.e., the vertical direction) are shown, but, at each of the positions in the Z-axis direction, the process at step S168 is performed.

The image processor 54 then performs removal of noise (i.e., singularities) (step S170). In the example shown in FIG. 49, an optimally focused sectional position at a determination point P(x03 y03, z03) for i, j=0, 3 is read as a position actually present at the position of a tomographic plane $SF_m$, which is shifted outwardly by no less than m-piece sections (toward the detector side). In such a case, the image processor 54 applies, for example, a threshold checking to a difference between the sectional positions to find out noise, thus regarding it abnormal data. Hence, the data of mutually adjacent sections are for example smoothed to smoothly connect the sections and replaced with a new set of smoothed positional data. Alternatively, data used for the data replacement may be produced by selectively giving priority to sectional data closer to the outside of the detector. Still alternatively, instead of such compensation using the data replacement, abnormal data may simply be removed from data being processed. It is also possible that the abnormal data to be removed include data abnormal in the Z-axis direction.

The image processor 54 then connects the positions with noise removed (that is, the positions showing the enamel) and three-dimensionally smoothens the connected positional data, whereby a surface image tracing the enamel is produced (step S171). Furthermore, the image processor 54 displays the produced surface image, as a 3D autofocus image $PI_{focus}$ which is a three-dimensional panoramic image all portions of which are automatically optimally focused, on the monitor 60 at a desired view angle (step S172).

Figure 50:
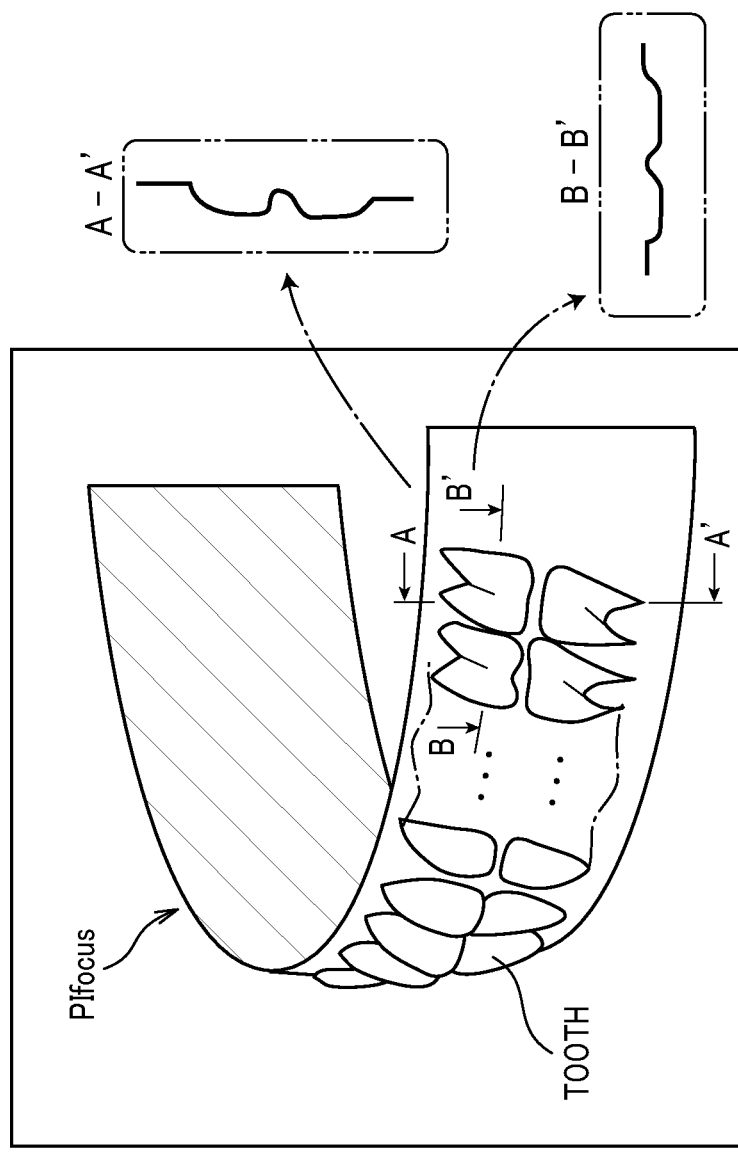
FIG. 50 is a view pictorially showing identification of the position of an optimally focused tomographic plane and a 3D autofocus image produced through smoothing.

Hence, as shown in FIG. 50, it is possible to provide the 3D autofocus image $PI_{focus}$ at the desired view angle, where the 3D autofocus image structurally shows the tooth row of the oral cavity of the object P in the clearest manner. In the drawing, the curved horseshoe-shaped range shows a range to display the 3D autofocus image $PI_{focus}$ and solid lines show the real positions and shapes of the tooth row. As shown by an A-A' line and a B-B' line, portions such as part of the gum (alveolar bone), the mandibular antra, the articulation of jaw, and the carotid artery can be depicted by a tomographic plane produced apart a given distance from the edges of the teeth (mainly the enamel) and the tomographic plane is projected three-dimensionally. In such a case, although it is not guaranteed that such portions other than the teeth are optimally focused, there cannot provide an unnatural feeling to 3D panoramic images. Of course, the calculation for optimal focusing may be improved to optimally focus such portions other than the teeth in the whole calculation, depending on purposes of diagnosis.

In this way, the produced 3D autofocus image $PI_{focus}$ is entirely curved to trace the tooth row and its surface is rough. This "roughness" depicts the real position and shape (contour) of each of the teeth by densities of pixel values. The remaining parts can also be depicted with no unnatural feeling.

Hence, the autofocus image $PI_{focus}$ indicating the real position and shape of the tooth row of each object P.

<Various Display Processes>

The image processor 54 then provides the operator with chances to observe the produced 3D autofocus image $PI_{focus}$ in other modes. Practically, in response to operation information from the operator, the image processor 54 determines whether or not it is desired to display the 3D autofocus image $PI_{focus}$ in other modes, in an interactive manner.

Figure 51:
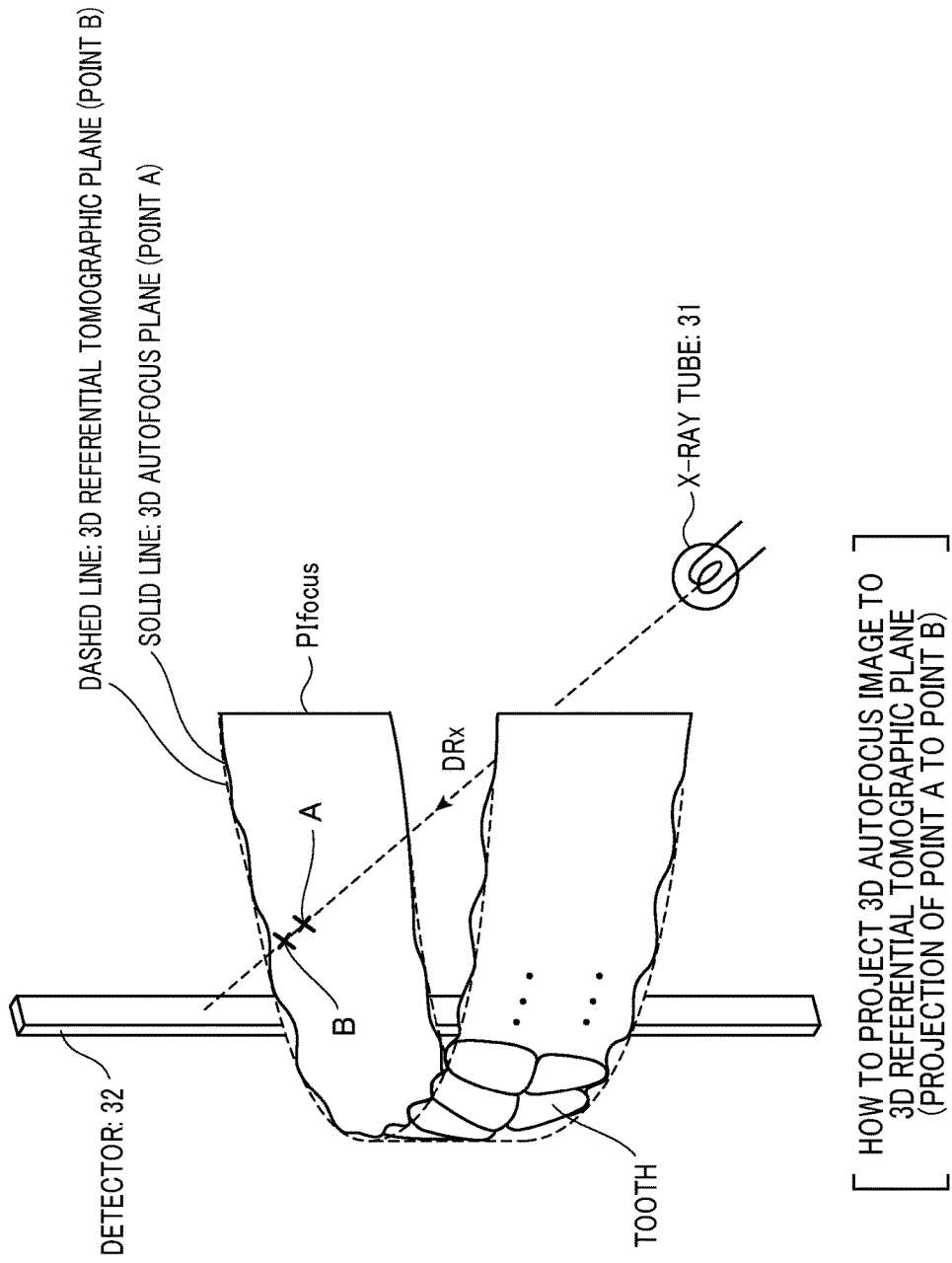
FIG. 51 is a view explaining a concept of processing for projecting the 3D autofocus image onto the 3D referential tomographic plane.

By way of example, the image processor 54 determines whether or not it is desired to observe a partial region of the 3D autofocus image (3D panoramic image) $PI_{focus}$ (in FIG. 30, step S60). When the determination at this step S60 is YES, it is further determined based on information from the operator whether the partial region is desired to be observed using a 3D referential tomographic plane SS or the rectangular plane (two-dimensional) of a referential panoramic image (step S61). When it is determined at this step S61 that the 3D referential tomographic plane SS is used, the image processor 54 re-projects the 3D autofocus image $PI_{focus}$ to the 3D referential tomographic plane SS in the X-ray radiation directions $DR_x$ passing through the pixels of the plane SS respectively (step S62). This re-projection is shown in FIG. 51. This re-projection can be performed by a sub-pixel method, by which each pixel of the 3D referential tomographic plane is sectioned by sub-pixels corresponding to the three-dimensional pixels and then subjected to the re-projection.

A re-projected image to the 3D referential tomographic plane SS is displayed on the monitor 60 as a 3D reference image $PI_{proj-3D}$ (step S63). An example of this 3D reference image $PI_{proj-3D}$ is shown in FIG. 52.

Meanwhile, when it is determined at step S61 that the rectangular plane of the referential panoramic image $PI_{st}$ is desired, the image processor 54 re-projects the 3D autofocus image $PI_{focus}$ to the rectangular plane, that is, the plane of a referential panoramic image (step S64). This re-projection is also performed by the known sub-pixel method, by which each pixel of the plane of the referential panoramic image is sectioned by sub-pixels corresponding to the three-dimensional pixels and then subjected to the re-projection. This re-projection is conceptually shown in FIG. 53. This re-projected image is displayed as a 2D reference image $PI_{proj-2D}$ on the monitor (step S65). An example of this 2D reference image $PI_{proj-2D}$ is shown in FIG. 54.

Figure 52:
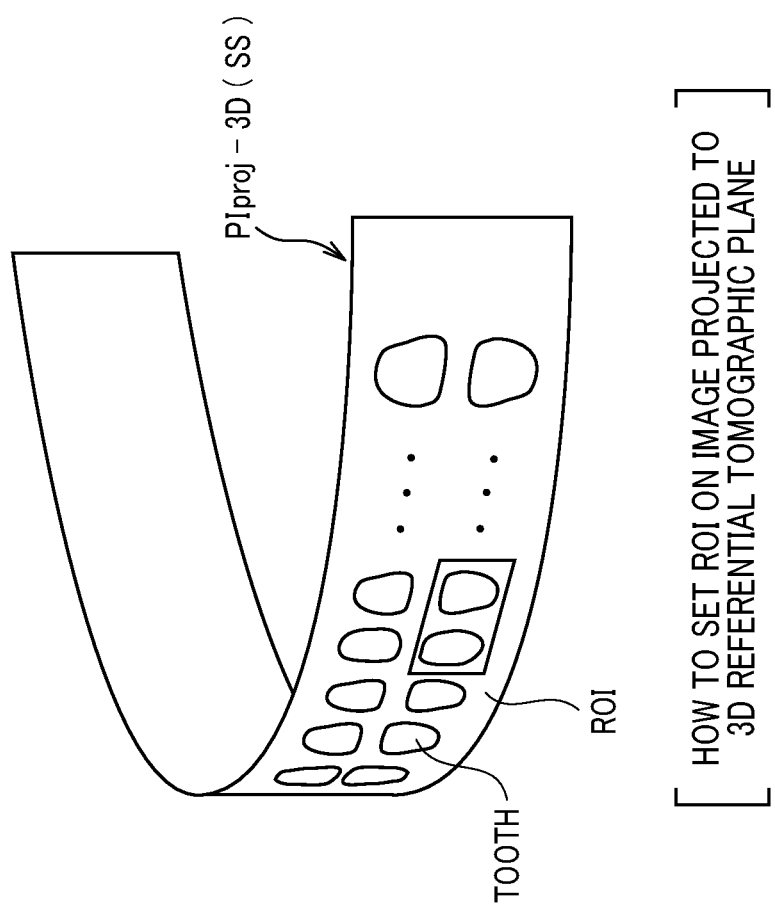
FIG. 52 is a pictorial view explaining an image projected to the 3D referential tomographic plane and a ROI set on the image.
Figure 53:
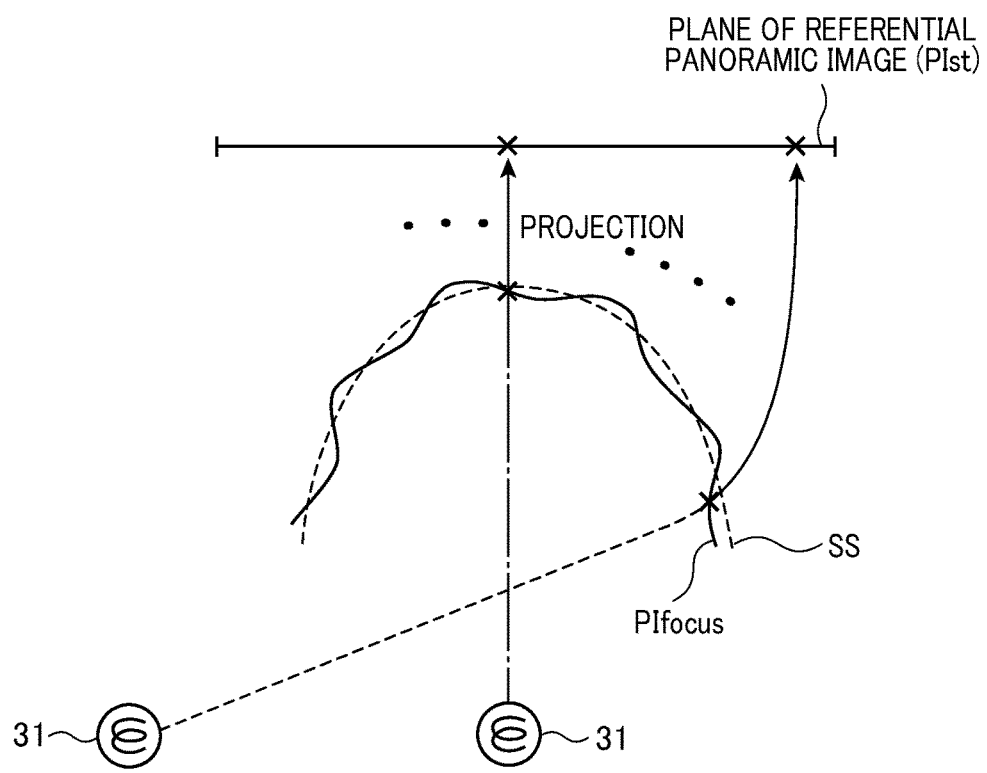
FIG. 53 is a view explaining a concept of processing for projecting the 3D autofocus image to a two-dimensional plane owned by a referential panoramic image.

The operator sets a desired ROI (region of interest) of, for example, a rectangle on either the 3D reference image $PI_{proj-3D}$ or the 2D reference image $PI_{proj-2D}$ (step S66; refer to FIGS. 52 and 53). A partial region designated by this ROI is enlarged, and superposed on the currently displayed 3D reference image $PI_{proj-3D}$ or the 2D reference image $PI_{proj-2D}$, for example (step S67). Of course, such a re-projected image may be displayed differently from the panoramic image, displayed together with the panoramic image in a divided manner, or displayed using a template consisting of a plurality of display blocks mapped along the tooth row.

The image processor 64 then determines whether or not the foregoing set of processes should be ended, using information from the operator (step S68). When being determined YES, the processing is returned to step S57, while being determined NO, the processing is returned to step S60 for repeating the foregoing processing.

By the way, when it is determined at step S60 that the partial region will not be observed, the image processor 54 further determines interactively whether or not the currently displayed 3D automatic image $PI_{focus}$ is necessary to be rotated, moved, and/or enlarged or reduced for display (step S69). If this determination is YES, the image processor responds to a command to rotate, move, and/or enlarge or reduce the 3D autofocus image $PI_{focus}$, and displays such a processed image (steps S70, S71). Then the processing proceeds to step S68 for repeating the foregoing steps.

Of course, the display modes will not be limited to the foregoing, but can adopt various other modes such as color representation.

When the operator commands to end the foregoing processing, the image processor 64 ends the processing via performance at steps S68 and S57.

Incidentally, after setting at step S66, the processing may skip the display at step S17 to directly proceed to step S69. In such a case, the ROI which has been set may be displayed together with the rotated, moved, and/or enlarged or reduced image at step S71.

As stated above, in the present embodiment, the structure of the panoramic imaging space can be analyzed three-dimensionally, which represents the projection directions three-dimensionally. Hence, as long as a panoramic image is focused, a 3D image produced from the panoramic image is prevented from being blurred and is accurately presented. This makes it possible to display the panoramic image reliably regardless of quality of positioning an object being imaged and to provide the entire images with clearer depiction.

The X-ray extraoral imaging apparatus 1 performs the scan as stated. It is therefore possible that the X-ray tube 21 and the detector 22 are moved along the orbit OB located closer to the object, while the X-ray beams XB scan the tooth row TR. In the embodiment, by way of example, the distance between the center of the anterior teeth of the tooth row TR and the detector 22 is 54 mm. The distance between the X-ray tube 21 and the detector 22 is 300 mm in the path of the X-ray beam XB passing through the geometrical center O of the orbit OB, and is less than 300 mm in other paths. As a result, even when the current of the X-ray tube 21 is lowered to values of approx. 500 μA, the imaging can be performed sufficiently. This tube current amount is less than 1/10 of a current amount needed by the conventional apparatus. The amount of X-ray exposure to the patient P can thus be lowered largely. In addition, the radiation controlled area is limited to the imaging space produced by the scan device 10. In other words, the outside space of the scan device 10, i.e., the orbit member 12 is not subjected to the regulations to the radiation controlled area. A dentist can thus stand by the scan device 10 and engage in work for imaging. The radiation controlled area occupies a lesser space.

In this way, compared with the conventional, the radiation controlled area can be confined to the inside area of the scan device 10, which is very narrow space, thus leading to a less-space and compact structure. With a patient seated on a treatment chair, panoramic images of the tooth row can be obtained under treatment. In consequence, this apparatus provides dentists with high usability. Thanks to three-dimensionally and finely detecting real positions and shapes of structural components, which are inherent to the present embodiment, the apparatus according to the embodiment is able to provide panoramic images whose resolution is comparable to or more than the conventional X-ray intraoral imaging apparatus.

Of course, the scan device 10 can be covered by an X-ray shield member during imaging, but this is not absolutely necessary.

In addition, since it is possible to image with use of X-ray amounts which is less than the conventional, there can have a margin up to the limit of the X-ray exposure even when the scan is performed two times or more. This means that the pre-scan can be performed to check a portion of interest beforehand, before performing a detailed scan for part of the portion of interest. The patient can view this condition though the patient monitor and the dentist can explain using the patient monitor in the treatment.

Hence, the radiation controlled area can be limited to the space provided by the scan device, thus using less space, while, with a patient seated (or lies) on the treatment chair, panoramic images of the tooth row can be acquired under the treatment. It is therefore to possible to provide three-dimensional panoramic images of high resolution, with enjoying good usability as well as a high capability which is almost a successor to the X-ray intraoral imaging apparatus.

(Mounting Example)

Figure 55:
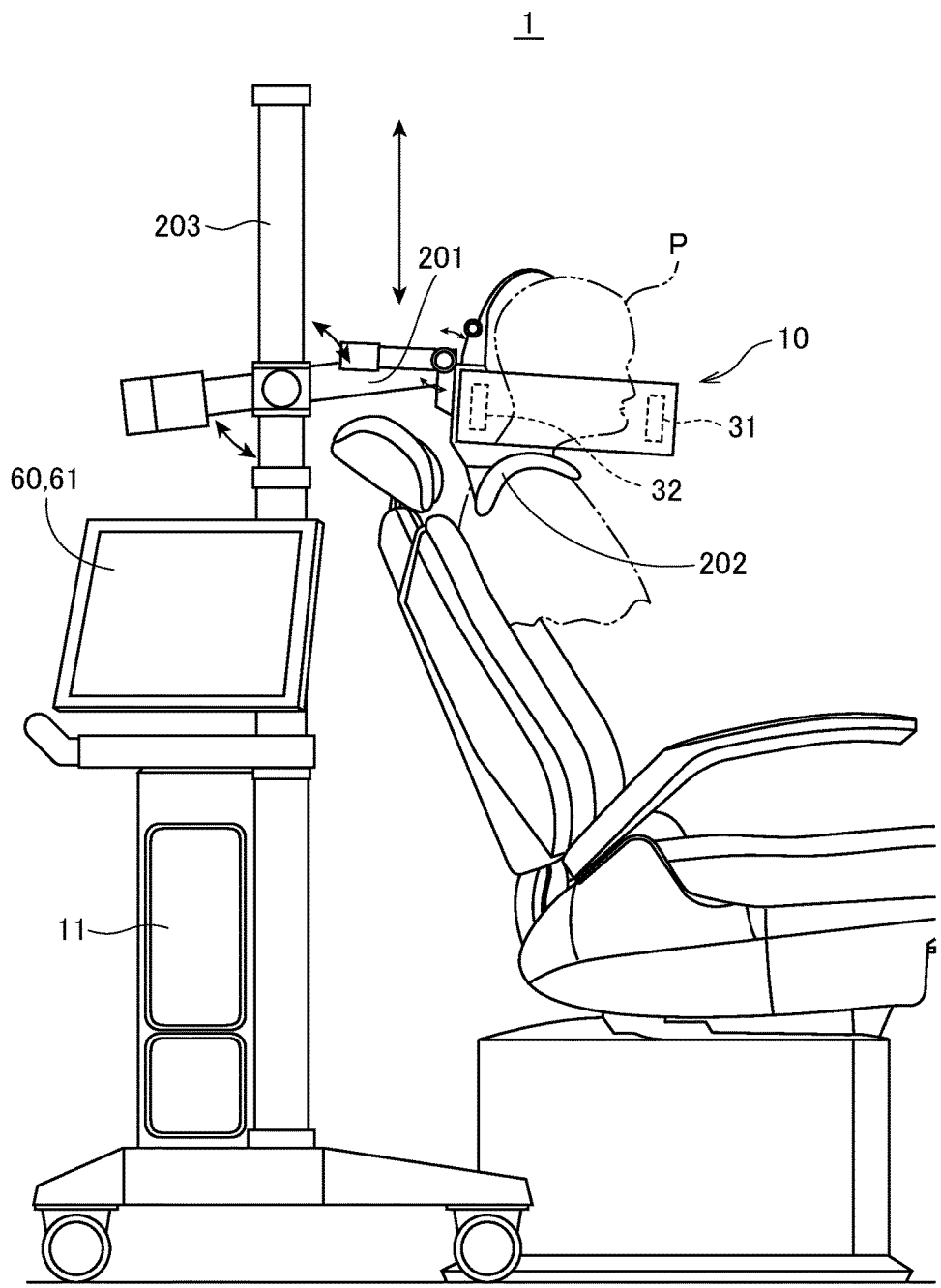
FIG. 55 is a view exemplifying mounting of the X-ray extraoral imaging apparatus according to the present embodiment.
Figure 56:
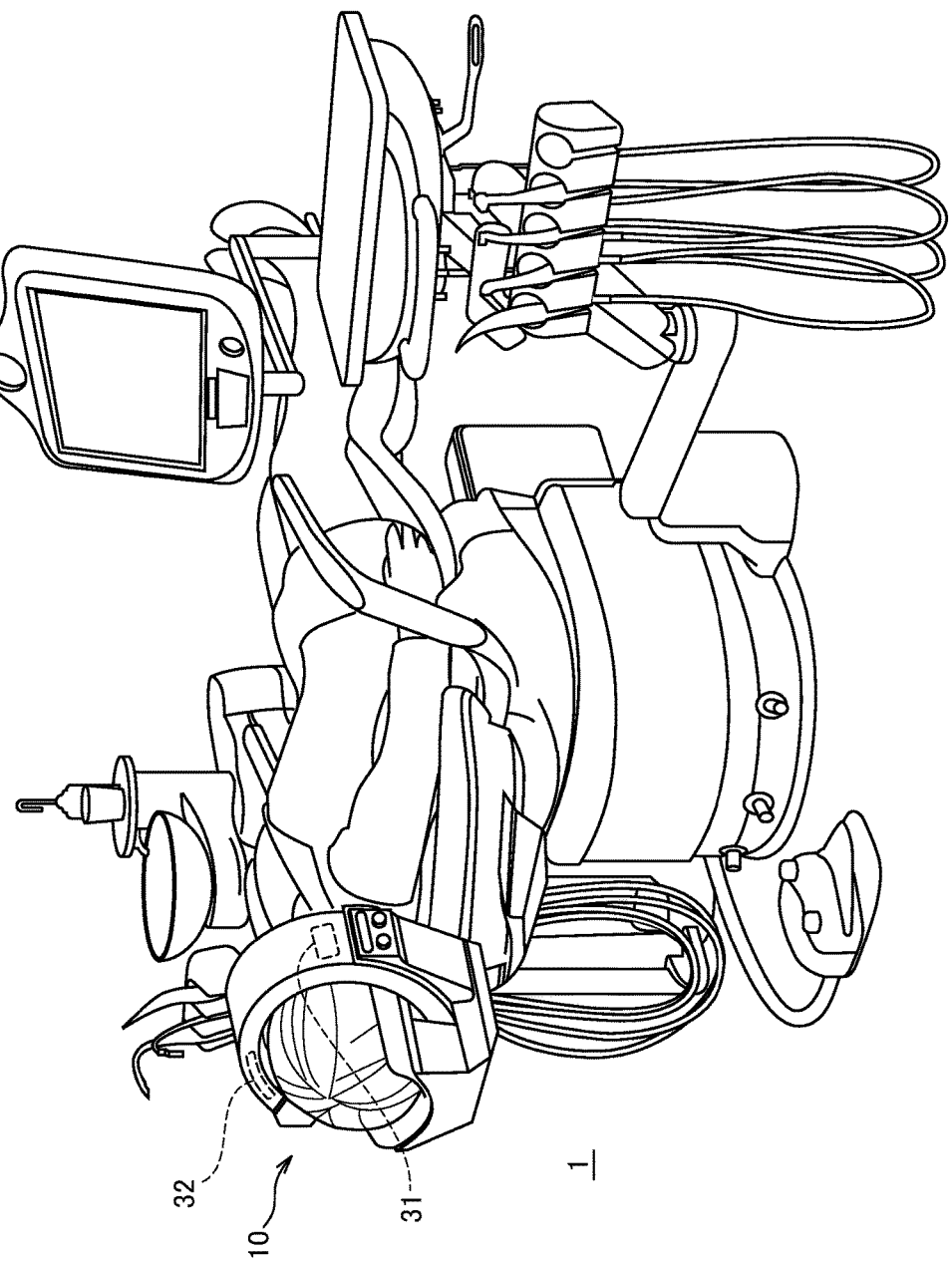
FIG. 56 is another view exemplifying mounting of the X-ray extraoral imaging apparatus according to the present embodiment.

The foregoing X-ray extraoral imaging apparatus 1 can be mounted in various modes. For example, as shown in FIG. 55, the scan device 10 is fixedly or detachably attached to an arm 201 behind the backrest of a treatment chair on which a patient is seated. The scan device 10 suspended from the above may be received by the seated patient. In the mounting example of FIG. 55, the scan device 10 is also held by a shoulder pad 202 put on the shoulders of the patient P. This makes it easier to position the jaw of the patient P. The arm 201 is attached to a pole 201 with wheels, and the pole 202 is equipped with computer 11, the touch-panel type monitor 60, and the operation device 61. The mounting system shown in FIG. 55 can be modified such that the scan device 10 itself is mounted solely on the patient's shoulders, head via a shoulder pad or a head pad, separately from any support Further, as shown in FIG. 56, the scan device 10 can be attached fixedly or detachably to the headrest portion of a dental treatment chair.

Figure 57:
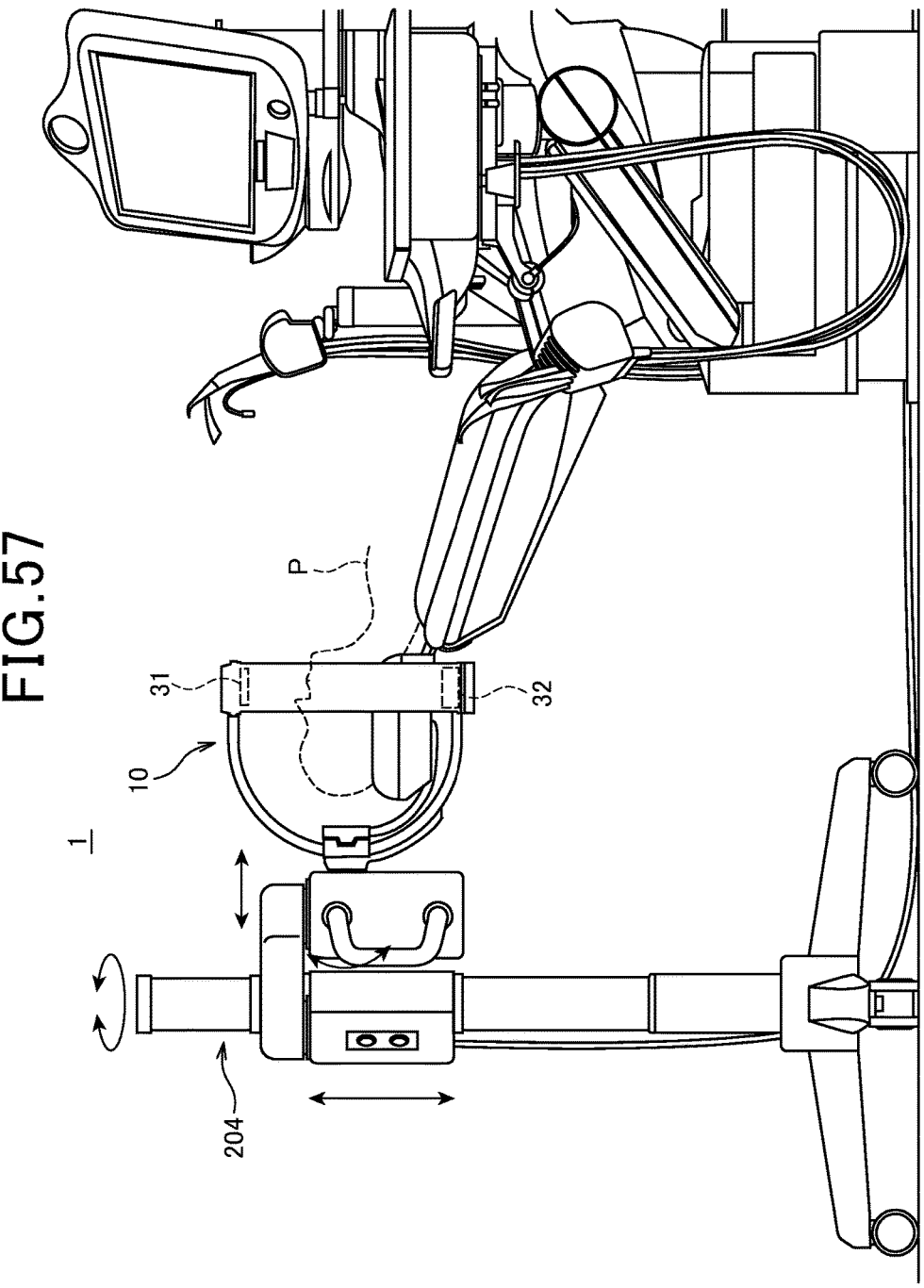
FIG. 57 is another view exemplifying mounting of the X-ray extraoral imaging apparatus according to the present embodiment.

Furthermore, as shown in U.S. Pat. No. 5,428,660, the scan device 10 can be attached to the end of an arm apparatus 204 which is a separate device. In this case, for imaging, the scan device 10 can be positioned to be around the head of a patient P seated on a treatment chair. This example is shown in FIG. 57.

In the embodiment, the scan device 10 has been described using the circular ring member 21 which provides the circular orbit OB, but this is just an example. The shape of a member providing the orbit OB is not necessarily circular. By way of example, an elliptical member may be used or a member with part of which is curved or formed into other shapes. Furthermore, with considering angle ranges necessary for the scanning, part of the ring member 21 may be opened, not closed. From openings of such open ends, cables for power and control signals can be connected to its inner circuits.

Meanwhile, the measure to improve irregularities in image densities can be applied as a post-process to a reconstructed image. For example, each lateral pixel row of the reference panoramic image $PI_{st}$ can be multiplied by smoothing weighting coefficients.

Using the phantom shown by the embodiment, it is possible to calibrate various parameters needed for structurally analyzing the imaging space and for reconstructing 3D images, such as an enlargement factor. Meanwhile, without using the phantom, previously designed values can be used as the necessary parameters, thus being a simplified manner.

By the way, the radiation tomographic imaging apparatus according to the invention is not limited to apparatuses practiced as the dental X-ray extraoral imaging apparatus, but may be practiced as an apparatus that three-dimensionally checks the real shape (position) of structural components based on the tomosynthesis technique.

[Second Embodiment]

With reference to FIGS. 58-68, the X-ray tomographic imaging apparatus of a second embodiment of the present embodiment will now be described.

In the present embodiment, the same or similar components to those in the apparatus described in the first embodiment will be given the same reference numerals for the sake of simplified description.

The X-ray tomographic imaging apparatus according to the present embodiment is provided with a construction for tomographic imaging (for panoramic imaging) based on the tomosynthesis technique and, without changes of its construction, a function for performing X-ray CT imaging by switching the apparatus to tomographic imaging based on a CT(Computed Tomography) technique, responsively to an operator's demand. In other words, there is provided a combined system capable of providing double role functions.

Figure 58:
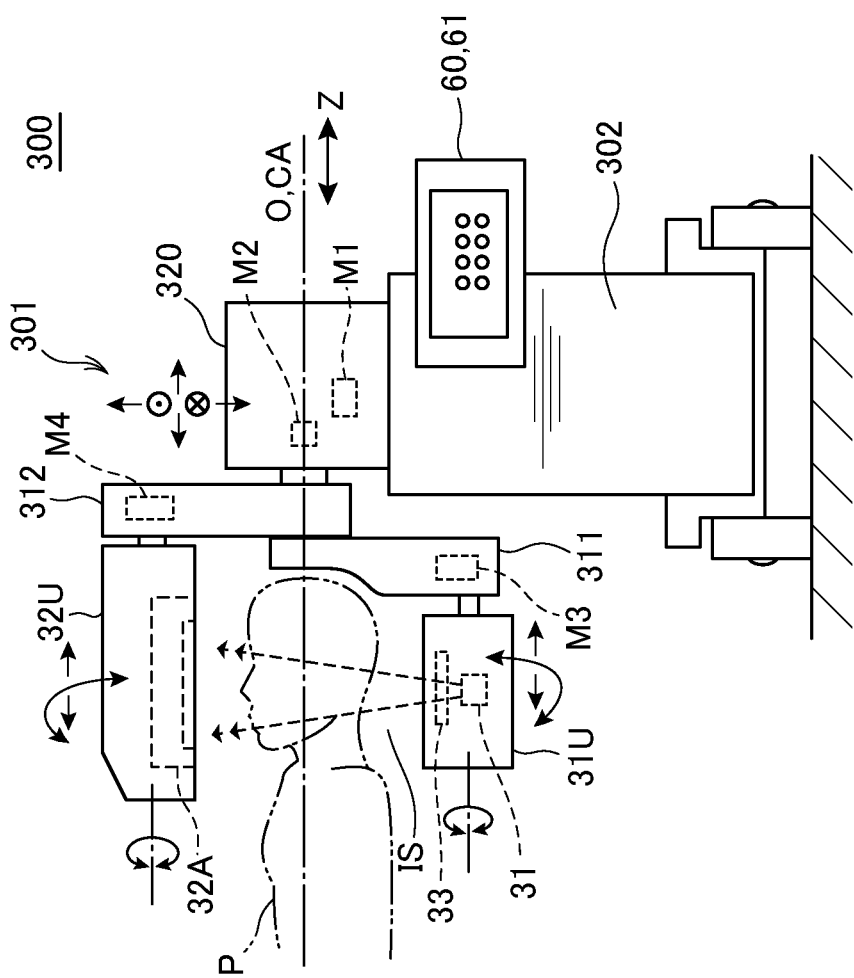
FIG. 58 is an outer view explaining an X-ray tomographic imaging apparatus according to a second embodiment of the invention.
Figure 59:
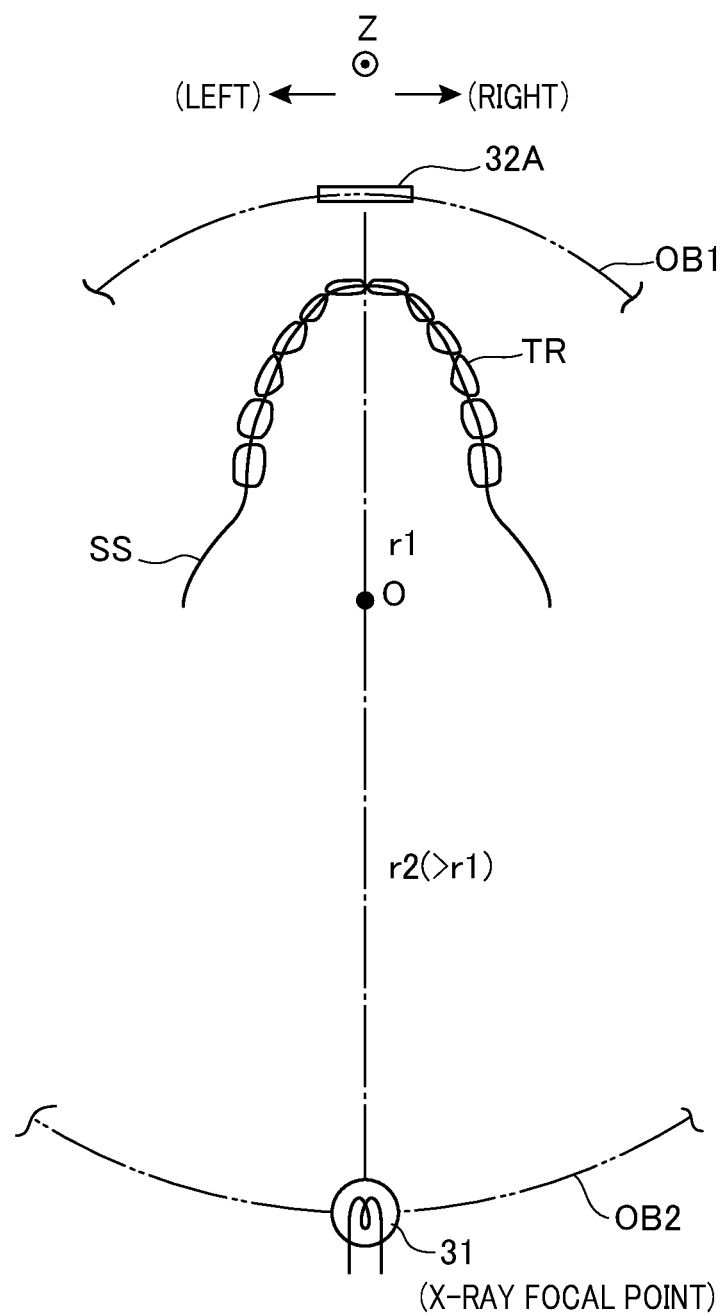
FIG. 59 is a view explaining different orbits for the X-ray tube and the detector in the second embodiment.
Figure 61:
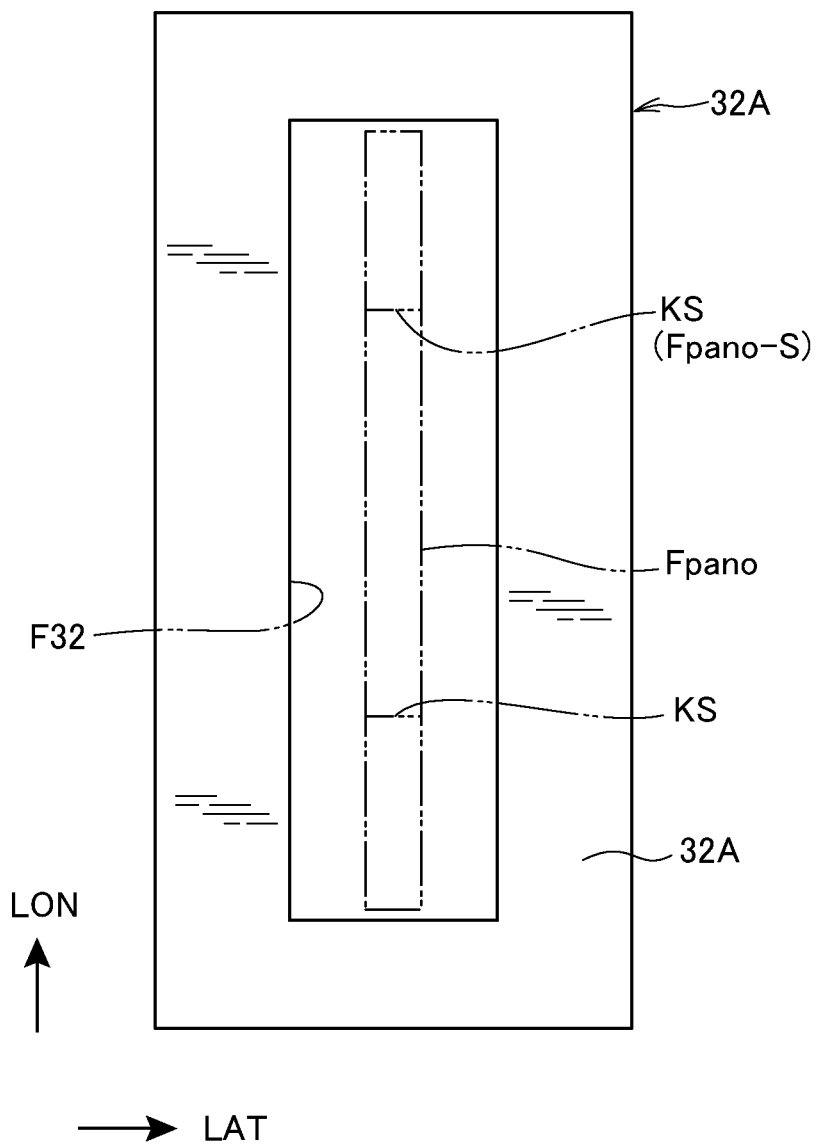
FIG. 61 is a view explaining an effective field of view in a panoramic imaging mode for the detector used in the second embodiment.

As shown in FIG. 58, an X-ray tomographic imaging apparatus 300 is equipped with a scan device 301 and a main cabinet 302. The scan device has first and second two arms 311 and 312 which are rotatable independently of each other. The first and second arms 311 and 312 have ends at which an X-ray unit 31U and a detector unit 32U are attached to cross with their arms, respectively. Hence, the first and second arms 311, 312, the X-ray tube unit 31U, and the detector unit 32U are provided to form two L-shaped arm portions as shown, where the two arm portions are rotatable around a CA passing through the rotation center O. The rotation provides an imaging space IS between the two arm portions. Within the imaging space IS, the jaw of an object P (patient) is positioned, who is lying on a dental chair or a patient couch.

The direction of the central axis CA is assigned to the Z-axis. Since the head of the patient P is directed along this Z-axis, this Z-axis is referred to as a body axis direction.

The X-ray tube unit 31U and the detector unit 32U are directly opposed or obliquely to each other with the jaw of the patient P therebetween. Similarly to the first embodiment, the X-ray unit 31U is provided with the X-ray tube 31 and the collimator 33. Also similarly to the first embodiment, the detector unit 32U is provided with an X-ray detector 32A.

The other ends of the first and second arms 311 and 312 are supported rotatably by the same support member 320 and are rotatable around the central axis CA. This support member 320 is secured to the main cabinet 302 with wheels. The main cabinet 302 is equipped with, inside thereof, the foregoing computer 11 and high-voltage generator 12. In order to interactively communicate with an operator, the main cabinet is provided with, outside thereof, the monitor 60 and the operation device 61.

Further, the X-ray tube 31 and the collimator 33 are incorporated in the X-ray tube unit 31U, while the detector 32A is incorporated in the detector unit 32U. X-rays radiated from the X-ray tube 31 is then subjected to collimation of its radiation field, and then pass through the jaw of the patient P. The transmitted X-rays are then detected by the detector 32A. Accordingly, in an of a panoramic imaging mode and a CT imaging mode, the paired X-ray tube 31 and detector 32A are rotated around the jaw of the patient P (however, the rotations of both X-ray tube 31 and detector 32A are controlled independently of each other), while the jaw portion is scanned by the X-ray beams. In other words, the same scan device 301 is used for imaging on both panoramic and CT modes.

In order to achieve the panoramic and CT imaging modes using the same scan device 301 without changes geometries, the distance from the rotational center O to the X-ray tube 31 is set to be longer by a desired length. The geometries here include a distance from the rotation center O to (the focal point of) the X-ray tube 31 and a distance from the rotation center O to (the detecting elements of) the detector 32A. For instance, the distance r1 between the rotation center O and the detector 32A is 15 cm, whilst the distance r2 between the rotation center O and (the focal point of) the X-ray tube 31 is 21.5 cm. Accordingly, as pictorially shown in FIG. 59, the detector 32A rotates around the rotation center O along a first circular orbit OB1, and the X-ray tube 31 rotates along a second circular orbit OB2 whose radius is larger than that of the first circular orbit OB1. Having the two circular orbits OB1 and OB2 is different from the first embodiment where the X-ray tube 31 and the detector 32 are rotated along the same circular orbit OB. As an alternative, the scan device provided with the two circular orbits OB1, OB2 whose radii are different from each other can be applied to the X-ray extraoral imaging apparatus described in the first embodiment.

In addition, to achieve both panoramic and CT imaging modes with use of the same scan device 301, various features are prepared which include control of a radiation field performed by the collimator 33, changes of attitudes of the detector 32A, movement of both X-ray tube 31 and detector 32A in the body axis direction Z of the patient P, and positional changes of the scan device 301 itself relatively to the patient jaw. These features will be described in the descriptions of operations.

For example, the tube voltage to the X-ray tube 31 is set to 70 kV and the tube current is set to an amount of 900 μA to 1.3 mA. Similarly to the first embodiment, the radiation controlled area is limited to the imaging space IS provided by the scan device 301.

The detector 32A will now be described. Similarly to that in the first embodiment, the detector 32A is configured as a semiconductor detector that directly converts X-rays to digital electric data corresponding to the incident X-rays. In this embodiment, the semiconductor detector is modularized into plural modules (17×4 pieces) MJ which are arrayed two-dimensionally, whereby, as shown in FIGS. 60(*a*),(*b*), the detector provides a strip-shaped rectangular effective field of view (i.e., an effective area that can detect incident X-rays for measurement). For instance, the effective field of view F32 is provided whose longitudinal length (the first direction) LON=14.2 cm and lateral length (the second direction) LAT=3.2 cm. The plural modules are packed in a box-shaped case 32*b*.

Control of the aperture of the collimator 33 and a masking process of the modules MJ are performed to this detector 32A for every imaging mode. For the panoramic imaging mode, the masking process and the control of the aperture of the collimator 33 are performed to obtain, for instance, a thin slit-shaped effective field of view $F_{pano}$ shown in FIG. 61. This effective field of view $P_{pano}$ has a longitudinal size LON=10 cm and a lateral size LAT=0.6 cm. As shown by an imaginary line KS in FIG. 61, the longitudinal size LAT may be shortened by controlling the collimator 33 in order to obtain an effective field of view $P_{pano-s}$. In this shorter field of view $F_{pano-s}$ can be used when the upper and lower tooth rows are imaged as main target structural components.

Figure 62:
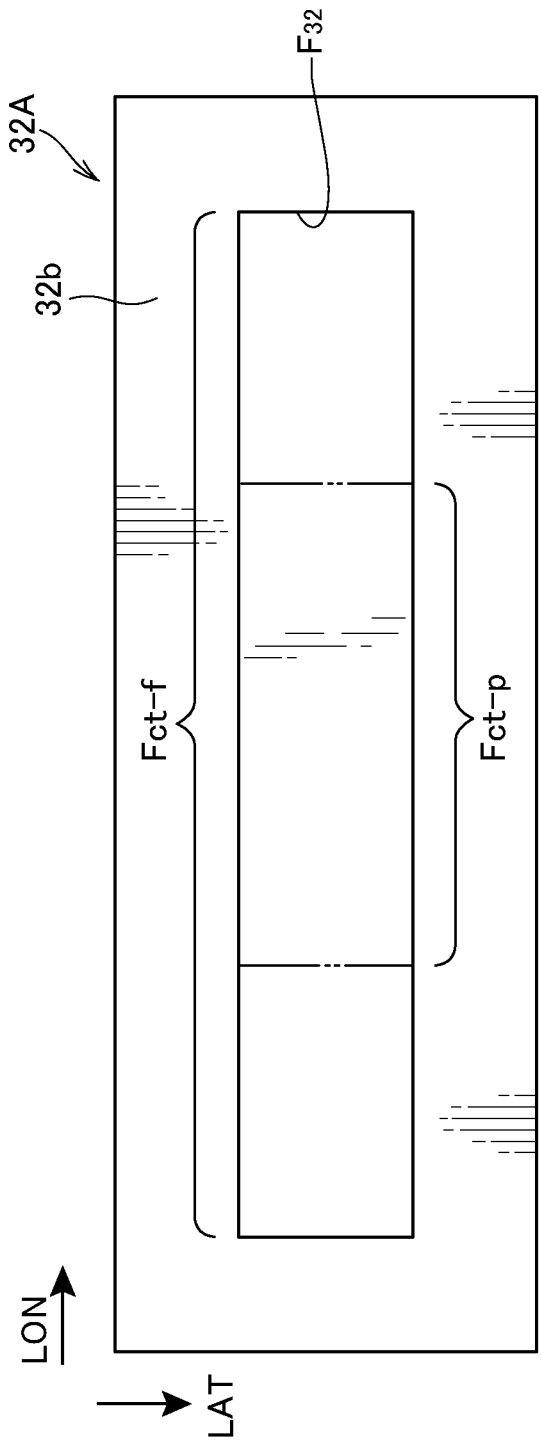
FIG. 62 is a view explaining an effective field of view in a CT imaging mode for the detector used in the second embodiment.

Meanwhile, for the CT imaging mode, the detector 32A is used by bringing down (rotating) it approx. 90 degrees to obtain a laterally oriented attitude. That is, the detector 32A is used as a laterally extending detector. In this case, the making process and the control of aperture of the collimator 33 make it possible to obtain two types of slit-shaped effective field of views $F_{ct-f}$ and $F_{Fct-p}$, as shown in FIG. 62, for instance. One of the effective field of view, $F_{ct-f}$ is suitable for CT imaging of the whole tooth rows in the jaw, and has a lateral size (the longitudinal size LON in FIG. 62) of 14.2 cm and a longitudinal size (the lateral size LAT) of 3.2 cm. The other effective field of view $F_{ct-p}$ is proper for CT imaging of partial portions of the tooth rows (e.g. only an anterior tooth area, a left molar area, or a right molar area), and has a lateral size (the longitudinal size LON in FIG. 62) of 7.1 cm and a longitudinal size (the lateral size LAT) of 3.2 cm.

Alternatively, the bringing-down (rotation) angle given to the detector 32A in the CT imaging mode is not always 90 degrees or approx. 90 degrees, but, with consideration of the shape of the effective field of view, may be an oblique angle to the longitudinal direction of the detector used for the panoramic imaging mode. In short, for the CT imaging mode, it is desired to widen the field of view to improve efficiency in scanning and secure a field (pixel area) of more than a certain length in the body axis direction.

Figure 63:
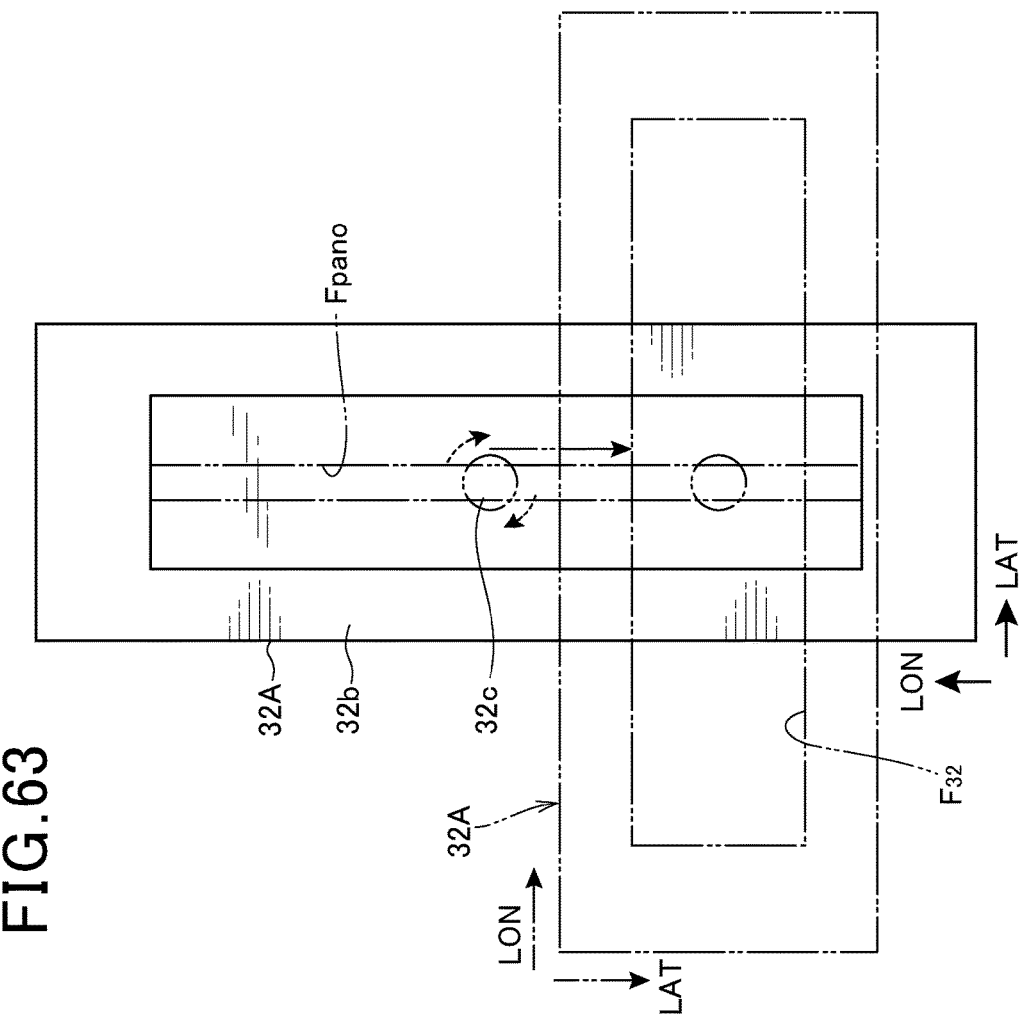
FIG. 63 is a view explaining rotation and movement in the height direction of the detector when the imaging mode is changed to the panoramic imaging mode to the CT imaging mode in the second embodiment.

This detector 32A is used in common for both panoramic and CT imaging modes. Hence, when shifting from the panoramic imaging mode to the CT imaging mode, it is necessary to rotate the detector 32A by approx. 90 degrees. This rotation is shown in FIG. 63. For this, the detector 32A is mounted in a case 32*b* and a rotatory shaft 32*c* is attached to a surface of the case 32*b*, which is the opposite side to the X-ray detection section. This rotary shaft 32*b* can be rotated by hand or automatically responsively to an instruction to change the imaging modes. This rotary shaft 32*c* is centered in the longitudinal direction of the detector 32A.

In addition, for the dental CT imaging, it is not sufficient that the detector 32A is simply brought down (rotated) by 90 degrees. It is necessary to perform positional adjustments including that i) the X-ray tube 31 and the detector 32A are moved in the body axis direction, ii) the detector 32A is brought down (rotated) 90 degrees, and iii) the detector 32A is slid to the body axis direction, iv) the scan device 301 is moved in the body axis direction Z, and v) the scan device 301 is shifted to the left or right along a plane orthogonal to the body axis direction Z.

These positional changes are due to particularities in the panoramic imaging of the tooth row and positioning necessary for X-ray CT imaging.

Through not described in the first embodiment, the panoramic imaging of the tooth rows should be performed in consideration of the fact that the cervical spine CS is present in the neck portion. The X-ray paths should be set by taking this fact into account (refer to FIG. 64). Practically, it is desired that the X-ray beams are transmitted between bones of the cervical spine CS as much as possible, before entering the tooth rows. In this respect, an angle of a space between bones is considered. For this purpose, positioning of the X-ray tube to the tooth rows and aperture control of the collimator are performed to allow the X-ray beam paths from the X-ray tube to be slightly upward. This is pictorially shown in FIG. 64.

Accordingly, when being shifted to the CT imaging, a simple rotation of approx. 90 degrees of the detector 32A will cause a displacement between the rotation center O and the tooth rows in the body axis direction Z. With consideration this, when the CT imaging is performed, the pair of the X-ray tube 31 and the detector 32A is positionally raised by a predetermined distance H1 (e.g. 5 cm) in the body axis direction Z, that is, the pair is shifted toward the head side by the distance H1. As a result, the heights of the tooth rows TH and the rotation center O are made to substantially agree with each other in the body axis direction Z.

In the CT imaging, the detector 32A is brought down (rotated) by approx. 90 degrees around the rotary shaft 32*c* thereof, so that the longitudinal-lateral relationship will be opposite to each other. Only the detector 32A is then lowered by a predetermined distance H2 (e.g. 4.3 cm) in the body axis direction, thus being shifted by the distance H2 away from the head side. In this way, the initial position of the detector 32A is decided in the scan device 301 for the CT imaging.

In the CT imaging, it is additionally necessary to move the scan device 301 in the body axis direction Z and shift the scan device 301 rightward of leftward along a plane perpendicular to the body axis direction Z. These movements are categorized as positional fine adjustments effective for imaging partial areas of the tooth rows of a patient P. In this embodiment, there are prepared, as CT imaging modes of partial areas of the tooth rows, an anterior-tooth imaging mode, a left molar-area imaging mode, and a right molar-area imaging mode. In the anterior tooth imaging mode, the scan device 301 itself is moved by a predetermined distance (e.g. 3 cm) toward the head side in the body axis direction Z. In the left molar-area imaging mode, the scan device 301 itself is translated leftward by a predetermined distance H4 (e.g. 3 cm) when viewing from the patient P. In contrast, in the right molar-area imaging mode, the scan device 301 itself is translated rightward by a predetermined distance H4 (e.g. 3 cm) when viewing the patient P. Accordingly, in the left and right molar-area imaging modes, although being along the same plane, the rotation center O is positionally translated leftward or rightward by the distance H4.

Incidentally, in order to move the scan device 301, as literally means, the scan device 301 supported by the main cabinet 302 is structured to be movable. Alternatively, only the first and second arms 311, 312 supported by the support member 320 may be configured to be moved.

Rotation movement mechanisms are used to move the scan device 301 in the body axis direction Z and along the plane perpendicular thereto, move the X-ray tube 31 and the detector 32A in the body axis direction Z, rotate the detector 32A around the rotary shaft 32b, and move the detector 32A in the body axis direction Z. The rotation movement mechanisms include a mechanism M1 which can move the support member 320 in the up and down directions and the longitudinal and lateral directions along a horizontal plane, and a mechanism M2 which can rotate the first and second arms 311 and 312 around the central axis CA independently of each other in the support member 320. Moreover, the rotation movement mechanisms include a mechanism M3, in the first arm 311, which can rotate the X-ray tube unit 31U in the direction of the central axis CA and enable the X-ray tube unit to rotate on an axis parallel to the central axis CA, and a mechanism M4, in the second arm 312, can move the detector unit 32U in the direction of the central axis CA and enable the detector unit to rotate on an axis parallel to the central axis CA. These mechanisms M1 to M4 are driven under control of the controller 55, which is performed via not-shown drivers.

Figure 65:
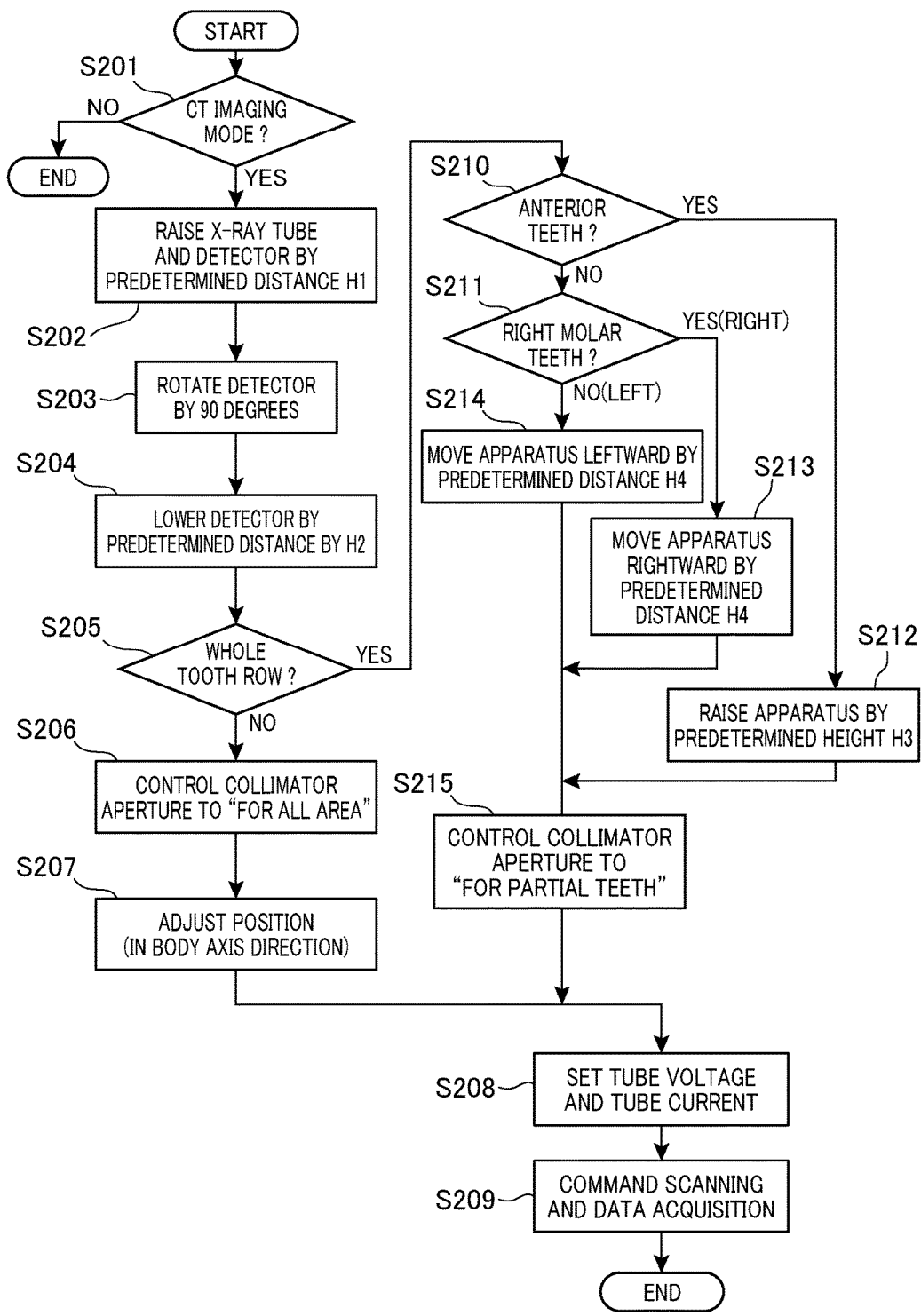
FIG. 65 is a flowchart for explaining control of a shift from the panoramic imaging mode to the CT imaging mode executed by a controller in the second embodiment.
Figure 66:
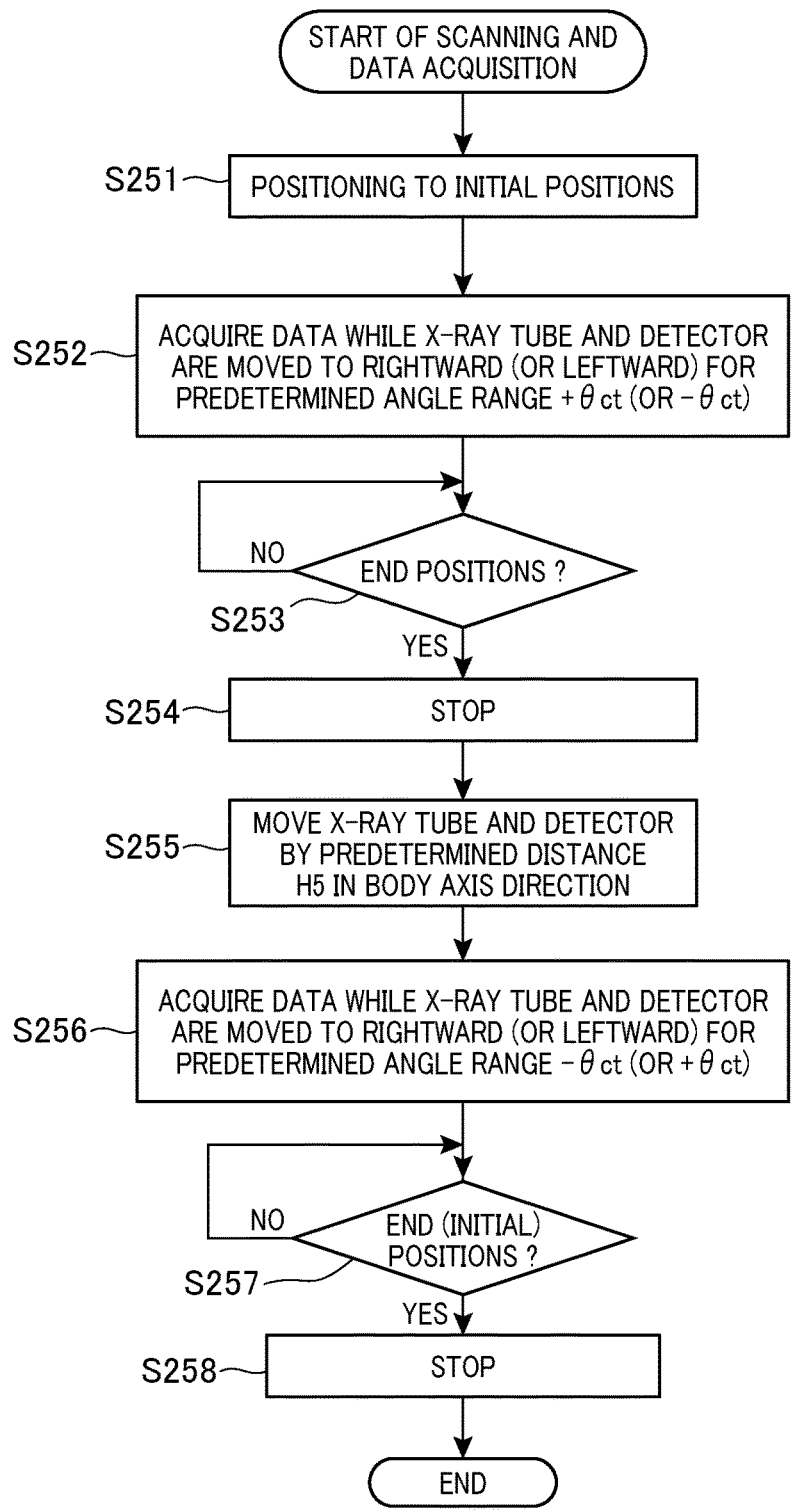
FIG. 66 is a flowchart explaining a scan and data acquisition executed by the controller in the second embodiment.

With reference to FIGS. 65 and 66, processes for shifting from the panoramic imaging to the CT imaging, which are executed by the controller 55, will now be described.

These processes are for shifting from the panoramic imaging state to the CT imaging in response to an operator's command. The X-ray tomographic imaging apparatus 300 has both functions for the panoramic and CT imaging, but is basically designed for the panoramic imaging function to which the CT imaging function is added. Hence, it is suitable to explain the processes for shifting from the panoramic imaging to the CT imaging. However, the apparatus may be designed to have both panoramic and CT imaging functions on an equal basis and to allow any one imaging mode to be selected when the apparatus 300 is activated by a user. In the case of returning from the CT imaging mode to the panoramic image mode, the opposite procedures to those shown in FIG. 65 are employed by the controller 55 such that the X-ray tube 31 and the detector 32A return to their initial positions for the panoramic imaging.

At step S201 in FIG. 65, the controller 55 responds to an operator's command sent via the operation device 61, to determine if or not the CT imaging is instructed. A determination of YES means that any one of a whole tooth-row CT imaging mode or a partial tooth-row CT imaging mode, thus common steps of steps S202 to S204 are executed in advance.

Figure 64:
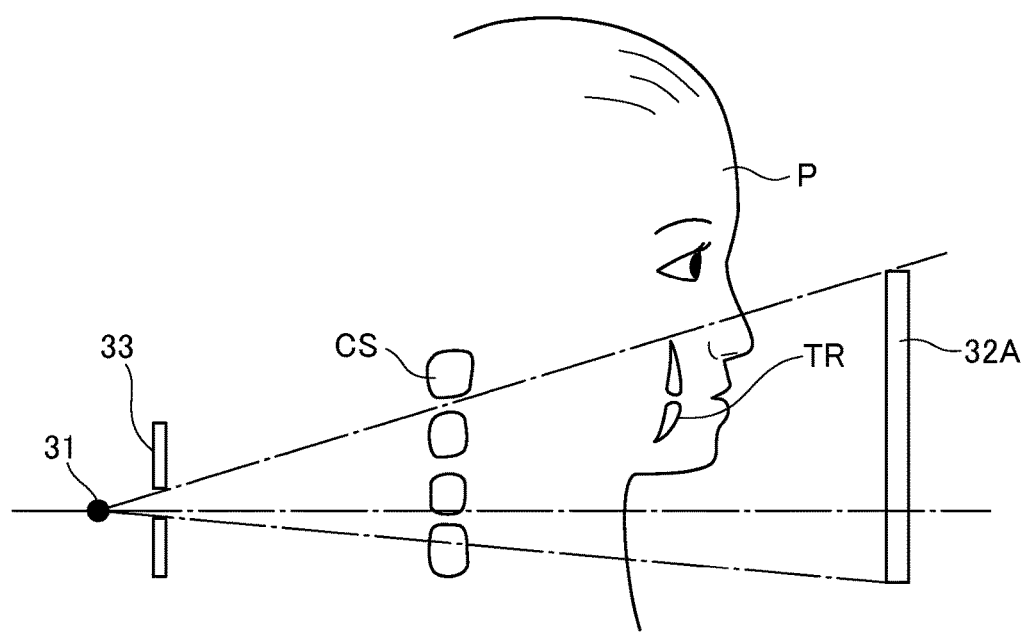
FIG. 64 is view explaining the X-ray tube and its radiation angles in the panoramic imaging.

First, the controller 55 operates such that the pair of the X-ray tube 31 and the detector 32A are moved by the predetermined distance H1 (e.g. 5 cm) toward the head side in the body axis direction Z (step S202). The controller 55 then makes the detector 32A rotate by 90 degrees to be brought down sideways (step S203). Then the detector 32A is lowered by the predetermined distance H2 (e.g. 4.3 cm) in the body axis direction Z (step S204). Incidentally imaginary lines in FIG. 64 show the state in FIG. 66(d).

The controller 55 then determines, at step S205, whether or not the CT imaging mode is the whole tooth-row CT imaging mode based on an operator's operational information. When this determination is YES, i.e., the whole tooth-row CT imaging mode is instructed, the processing proceeds to step S206, where the aperture of the collimator 33 is adjusted to make the X-ray radiation field equal to the effective field of view $F_{ct-f}$ on the X-ray detection section of the detector 32A. The controller then proceeds to step S206, where it receives the operator's operational information to finely adjust the position of the scan device 301 in the body axis direction Z, whereby the imaging position is finally set. This fine adjustment may be conducted by hand or in an automatic way.

Further, at step S208, the tube voltage and tube current to the X-ray tube 31 are decided, before proceeding to step S209 where the scan is commanded to acquire data. The process at step S209 will be detailed later.

When it is determined NO at step S205, it is understood the partial tooth-row CT imaging mode is instructed. The controller 55 then receives operator's operational information to determine that the anterior-tooth CT imaging mode has been instructed (step S210), the right molar-area CT imaging mode has been instructed (YES at step S211), or the left molar-area CT imaging mode has been instructed (NO at step S211).

If the anterior-tooth CT imaging mode is instructed, step S212 enables the scan device 301 to move by the predetermined distance (e.g. 3 cm) toward the head side in the body axis direction Z. The right molar-area CT imaging mode is instructed, step S213 enables the scan device 301 itself to translate rightward by the predetermined distance H4 (e.g. 3 cm) when viewing from the patient P. In contrast, the left molar-area CT imaging mode is instructed, step S214 allows the scan device 301 itself to move leftward by the predetermined distance H4 (e.g. 3 cm) when viewing from the patient P.

When the positional fine adjustment of the scan device 301 has been completed for the partial CT imaging, the processing proceeds to step S215, where the aperture of the collimator 33 is adjusted to make the X-ray radiation field equal to the partial effective field of view $F_{ct-p}$ imaginarily set on the X-ray detection section of the detector 32A. The foregoing steps S208, S209 are then executed.

Of the foregoing steps, the processes identical in contents to steps S202, S203, S204, S212, S213 and S214 may be instructed though operator' manual operations.

In addition, the foregoing distances H1, H2, H3 and H4 are finely adjusted amounts which are decided based of patients' frames, especially statistical sizes of the patients' jaws (including the tooth rows). These amounts can be adjusted by an operator with consideration of a patient's frame to be examined for each of the examinations.

With reference to FIG. 66, data acquisition in the CT imaging mode will now be described. At step S251, the controller 55 first positions the pair of the X-ray tube 31 and the detector 32A at their initial positions so that these are mutually directly opposed to each other. On completion of this positioning, through processes at steps S252 and S253, the controller makes the first and second arms 311, 312 start to rotate around the central axis CA clockwise (or counterclockwise) by, for example, a predetermined angle range θct (+210 degrees or −210 degrees), during which rotation frame data of transmitted X-ray beams detected by the detector 32A are acquired at predetermined intervals. The acquired frame data are temporarily stored in the buffer memory 52.

When the first and second arms 311, 312 arrive at their end positions of the predetermined angle range θct, the controller 55 performs at step S254 to stop their rotations. Then, at step S255, the pair of the X-ray tube 31 and the detector 32A, i.e., the first and second arms 311, 312 are moved toward the chest side by the predetermined distance H5 (e.g. 19 mm) in the body axis direction Z.

After this, through processes at steps S256 and S257, the controller makes the first and second arms 311, 312 start to rotate around the central axis CA clockwise (or counter-clockwise) by, for example, the predetermined angle range θct (+210 degrees or −210 degrees) from the foregoing end positions to the initial positions, during which rotation frame data of transmitted X-ray beams detected by the detector 32A are acquired at predetermined intervals. The acquired frame data are temporarily stored in the buffer memory 52.

In this way, the outward scan for the predetermined angle θct, the movement of the scan device by the predetermined distance H5 in the body axis direction, and the return scan for the predetermined angle θct are performed in series. When this series of actions are ended, the first and second arms 311 and 312 are ordered to stop (step S258).

The foregoing data acquisition allows the whole tooth-row CT imaging mode to secure an image region given by a preset volume B1 (e.g. 85 mmφ×height of 38 mm) which covers the whole tooth rows around the rotation center O, as shown in FIGS. 67(a),(b). While, for the partial tooth-row CT imaging mode, as shown in FIGS. 68(a),(b), a preset volume B2 covering at least the anterior teeth, the left molar teeth, or the right molar teeth can be secured as a imaging region.

Since the scanning enables acquisition of transmitted data for any one of these three-dimensional volume B1 or B2, the image processor 54 applies a desired algorithm to the acquired data to reconstruct three-dimensional CT data. By processing the reconstructed three-dimensional data with an appropriate mufti-planar reconstruction method, tomographic images of sections along a whole tooth row and tomographic images of sections along a partial tooth row can be cut out from the reconstructed data.

Components other than the above are constructed in the same way or similarly as or to those described in the first embodiment.

In this way, the X-ray extraoral imaging apparatus according to the present embodiment makes it possible to easily perform not only the panoramic imaging but also the X-ray CT imaging using the same apparatus. It is not required to change scan devices, thus providing higher usability and higher versatility. In addition, the operations and effects obtained in the first embodiment can be also enjoyed.

As a further modification, the X-ray tomographic imaging apparatus according to the second embodiment may be adopted as a CT scanner for mammography. Practically, a patient is laid on a patient bed in a prone posture so that patient' breasts are suspended through holes of the bed. The breasts are pinched by breast pressing plates with a pressing force weaker than that adopted in the conventional mammography, thus fixedly positioning the breasts. Incidentally, in the conventional mammography, the breasts are also pinched by breast pressing plates with less X-ray absorption. In the same as the forgoing, the first and second arms 311, 312 of the foregoing scan device 301, that is, the X-ray tube 31 and the detector 32A, are rotated around the positionally fixed breasts for a predetermined angle range (outward), moved in the body axis direction, and rotated again for the predetermined angle range (return). This scanning provides X-ray transmission data to the breast tomosynthesis processing or X-ray CT imaging, thus being able to produce tomographic images for mammography.

Alternatively, with a patient is seated on a chair, the patient's breasts are positioned, instead of the head explained in the foregoing. The positioned breasts are then pinched by breast pressing plates with a weaker force, as described above. In this state, the breasts are scanned as above, providing the mammography described above.

In such mammography, a plurality of detectors is arranged. For example, three detectors are arranged discreetly. Alternatively, part of a flat detector is used. These detector configurations widen a projection angle in which data are acquired for tomosynthesis. In addition, definition of tomographic images can be improved, with less X-ray exposure. In this way, the number of detectors provided in the X-ray tomographic imaging apparatus is not always limited to one, but plural detectors or a flat detector equivalent to plural detectors are also adopted as the detector according to the present invention.

Further, in the detector used for mammography, a distance between a detector field view and a detector edge on a breast side is made as small as a few millimeters. This structure enlarges the detection area as much as possible, which is important in both tomosynthesis and CT tomographic imaging.

Accordingly, this kind of apparatus can enjoy the advantages explained in the second embodiment.

INDUSTRIAL APPLICABILITY

According to the X-ray tomographic imaging apparatus of the present invention, the apparatus can be applied to a dental panoramic imaging apparatus as one of applications. In this case, the radiation controlled area is limited a space occupied by a scan device or a scanner, whereby the apparatus can be made compact. In addition, with a patient seated (or laid) on a treatment chair, panoramic images can be obtained during a treatment of the patient, which provides excellent usability. It is also possible to provide higher-resolution panoramic images which can be used as an alternative to image from the X-ray intraoral imaging apparatus. Additionally, panoramic imaging and CT imaging can be performed selectively, providing dual imaging functions by a single apparatus, leading to higher versatility in medical fronts. Furthermore, this X-ray tomographic imaging apparatus is not limited to applications for dental use, but may be applied to other medial modalities and nondestructive use, still providing the foregoing advantages.

DESCRIPTION OF REFERENCE NUMBERS

1 X-ray extraoral imaging apparatus (X-ray tomographic imaging apparatus)
10, 301 scan device
11 computer
21 ring member
31 X-ray tube
31U X-ray tube unit
32, 32A detector unit
33 collimator
54 image processor
55 controller (CPU)
300 X-ray tomographic imaging apparatus
302 main cabinet
311 first arm
312 second arm
320 support section P object being imaged
OB, OB1, OB2 trajectory
TR tooth row
IS imaging space
O rotation center
CA central axis

What is claimed is:
1. An X-ray tomographic imaging apparatus, comprising:
a data acquiring device comprising:
an X-ray tube radiating X-rays whose intensities are dependent on an amount of current to be supplied thereto;
a detector provided with a detection section in which a plurality of pixels are arranged two-dimensionally, the pixels detecting the incoming X-rays and outputting, frame by frame, digital electric data;
a support member producing a curved orbit and supporting the X-ray tube and the detector such that the X-ray tube and the detector are movable along the orbit independently of each other,
a moving unit moving the X-ray tube and the detector along the orbit independently of each other such that the X-rays are transmitted through an object being imaged, at desired angles and at respective positions in a scanning direction of a desired tomographic plane of the object, wherein the object is located inside the orbit provided by the data acquiring device;
a panoramic image procuring unit performing tomosynthesis imaging with the data acquired by the data acquiring device to produce a panoramic image of the tomographic plane based on the data; and
a tomographic image producing unit producing a tomographic image based on the data acquired by the data acquiring device and the panoramic image produced by the panoramic image procuring unit, structural components existing in the object being optimally focused in the tomographic image and distortions due to differences in angles of paths of the X-rays being suppressed in the tomographic image,
wherein the X-ray tomographic imaging apparatus comprises a CT (Computed Tomography) image reconstructing unit reconstructing tomographic images, based on a CT reconstruction method, from the frame data acquired by the detector,
the moving unit is configured to move, along the orbit, the X-ray tube and the detector which are directly opposed to each other, and
a switching unit switching an attitude of the detector when CT imaging is desired to be performed instead of the tomosynthesis imaging.

2. The apparatus of claim 1, further comprising
an X-ray amount adjusting unit adjusting amounts of the X-rays such that the amounts of the X-rays radiated per unit time become uniform at the respective positions during a period of time during which the X-ray tube and the detector are moved by the moving unit.

3. The apparatus of claim 2, wherein the X-ray amount adjusting unit is composed of one or more units designated among a tube current adjusting unit adjusting a value of the current to the X-ray tube depending on the respective positions, a tube voltage adjusting unit adjusting a value of a tube voltage applied to the X-ray tube depending on the respective positions, and an acquisition time adjusting unit adjusting an acquisition time necessary for the detector to acquire the data, the acquisition time being dependent on the respective positions.

4. The apparatus of claim 3, wherein
the object is a tooth row of a patient's jaw, and
the tube current adjusting unit increases the value of the current for X-ray scanning of the tooth row along paths passing through a cervical spine acting as an obstacle shade, more than the value of the current for X-ray scanning of the tooth row along paths other than the paths passing through the cervical spine.

5. The apparatus of claim 3, wherein
the object is a tooth row of a patient's jaw, and
the acquisition time adjusting unit widens the acquisition time for X-ray scanning of the tooth row along paths passing through a cervical spine acting as an obstacle shade, more than the acquisition time for X-ray scanning of the tooth row along paths other than the paths passing through the cervical spine.

6. The apparatus of claim 1, further comprising
an enlargement factor correcting unit correcting distortions in a height direction of the panoramic image produced by the panoramic image procuring unit, based on irregularities of an enlargement factor among the respective positions in the scanning direction, the enlargement factor showing enlargement of an image produced by the X-rays onto the tomographic plane in the height direction perpendicular to the scanning direction.

7. The apparatus of claim 1, wherein
the data acquiring device is equipped with a collimator collimating the X-rays from the X-ray tube, the collimator being movable independently of the X-ray tube, and
the moving unit is provided with a unit moving the collimator relatively to the X-ray tube depending on angles of the X-rays transmitted across the tomographic plane at respective positions in the scanning direction.

8. The apparatus of claim 7, wherein the collimator is equipped to be movable in a direction perpendicular to radiation directions of the X-rays or rotatable in the radiation directions.

9. The apparatus of claim 1, wherein the orbit is a circular orbit or an elliptical orbit.

10. The apparatus of claim 1, wherein the orbit is a circular orbit in which the object of a patient is allowed to be located.

11. The apparatus of claim 10, wherein the support member produces the circular orbit with part of which is opened.

12. The apparatus of claim 1, wherein the X-ray tube has an X-ray focal point of which diameter is 0.3 mm or less, and
the support member is configured to support the X-ray tube and the detector to hold a distance between the focal point of the X-ray tube and the detection section of the detector at 40 cm or less.

13. The apparatus of claim 12, wherein the data acquiring unit is equipped with an X-ray shielding unit for shielding an outer side of the support member against the X-rays, at least, while acquiring the data.

14. The apparatus of claim 1, wherein
the tomographic image producing unit comprises
a referential-plane image reconstructing unit for reconstructing, as a referential-plane image, a projection image of a desired tomographic plane of the object based on the data acquired by the data acquiring device, and
an optimally-focused image producing unit for producing a three-dimensional optimally focused image based on data of the referential-plane image and the frame data.

15. The apparatus of claim 14, wherein
the desired tomographic plane is a three-dimensional (3D) referential tomographic plane which is curved and rectangular in a space between the X-ray tube and the detector,
the object is a tooth row of a patient, and
the referential-plane image reconstructing unit is configured to reconstruct a panoramic image of the tooth row.

16. The apparatus of claim 15, wherein
the tomographic image producing unit comprises
a tomographic plane setting unit for setting a plurality of tomographic planes along the 3D referential tomographic plane in a direction opposed to the 3D referential tomographic plane,
a pixel value calculating unit for calculating pixel values of each of the plurality of tomographic planes,
a position identifying unit for identifying optimally focused sampling points of the portion being imaged based on image data of both the 3D referential tomographic plane and the plurality of tomographic planes to which the pixel value calculating unit provides the pixel values,
a pixel value providing unit for providing the sampling points identified by the position identifying unit, with pixel values based on the pixel values at the sampling points corresponding to the panoramic image and being present in a viewing direction from the X-ray tube to the detector via the respective sampling points,
a tooth row deciding unit for deciding the tooth row by recognizing the 3D referential tomographic plane provided at the sampling points to which the pixel values are provided by the pixel value providing unit and a characteristic pattern shown by pixel values of the plurality of tomographic planes, and
a noise removing unit for removing noise from the sampling points of the tooth row decided by the tooth row deciding unit.

17. The apparatus of claim 16, wherein
the noise removing unit comprises
a classification unit for classifying substances, every characteristic shown by the same type of substance based on the frequency characteristic at the respective sampling points, and
a smoothing unit for smoothly connecting each substance classified by the classification unit.

18. The apparatus of claim 1, wherein
the switching unit comprises
a position changing unit for positionally moving the X-ray tube and the detector toward a patient's head in a body axis direction thereof by a predetermined distance, and
an angle changing unit for changing an angle of the detector such that a first attitude of the detector which is for performing the tomosynthesis imaging with a patient's jaw serving as the object is changed to a second attitude of the detector which is for performing the CT imaging with the patient's jaw.

19. The apparatus of claim 18, wherein
the detection section of the detector has first sides and second sides, the first and second sides being perpendicular to each other, the pixels mapped in a direction of the first sides being less in number than the pixels mapped in a direction of the second sides, and
the angle changing unit is configured to change the angle of the detector such that the first attitude in which the first sides are directed laterally, which is for performance of the tomosynthesis imaging of the patient's jaw, is changed to the second attitude in which the second sides are directed laterally, which is for performance of the CT imaging with the patient's jaw.

20. The apparatus of claim 19, further comprising
a CT imaging mode deciding unit for deciding, interactively with an operator, whether the CT imaging is performed with a whole area of tooth rows of the jaw or a partial area of the tooth rows of the jaw, and
a second aperture controlling unit for controlling the area of the aperture of the collimator depending on a CT imaging mode decided by the CT imaging mode deciding unit.

21. The apparatus of claim 18, wherein
the data acquiring device comprises
a collimator having an aperture changeable in area for changing an X-ray incident region of the detection section of the detector, and
a first aperture controlling unit for controlling the area of the aperture of the collimator in accordance with the first and second attitudes.

22. The apparatus of claim 1, wherein
the orbit includes a first orbit having a predetermined radius from a rotation center provided when the X-ray tube and the detector are rotated around a patient's jaw and a second orbit having a radius longer than the radius of the first orbit, and
the support member comprises a first arm movably supporting the X-ray tube along the second orbit, and a second arm movably supporting the detector along the first orbit.

23. The apparatus of claim 22, wherein
the first arm is configured to movably support the X-ray tube along the second orbit so that the X-ray tube is directly opposed to the detector, and
the second arm is configured to movably support the detector along the first orbit so that the detector is directly opposed to the X-ray tube.

* * * * *